United States Patent
Kates et al.

(10) Patent No.: US 12,280,038 B2
(45) Date of Patent: Apr. 22, 2025

(54) L-PAG DERIVATIVES FOR TREATMENT OF SLEEP DISORDERED BREATHING (SDB)

(71) Applicants: The University of Chicago, Chicago, IL (US); IIT Research Institute, Chicago, IL (US)

(72) Inventors: Michael J. Kates, Philadelphia, PA (US); Nanduri R. Prabhakar, Chicago, IL (US); David L. McCormick, Chicago, IL (US); Miguel Muzzio, Chicago, IL (US)

(73) Assignees: The University of Chicago, Chicago, IL (US); IIT Research Institute, Chicago, IL (US)

( * ) Notice: Subject to any disclaimer, the term of this patent is extended or adjusted under 35 U.S.C. 154(b) by 71 days.

(21) Appl. No.: 17/808,645

(22) Filed: Jun. 24, 2022

(65) Prior Publication Data

US 2022/0323415 A1 Oct. 13, 2022

Related U.S. Application Data

(63) Continuation of application No. 15/929,512, filed on May 6, 2020, now abandoned, which is a continuation of application No. 16/470,445, filed as application No. PCT/US2017/067689 on Dec. 20, 2017, now abandoned.

(60) Provisional application No. 62/436,942, filed on Dec. 20, 2016.

(51) Int. Cl.
| | | |
|---|---|---|
| *A61K 31/4164* | (2006.01) | |
| *A61K 31/197* | (2006.01) | |
| *A61K 31/198* | (2006.01) | |
| *A61K 31/216* | (2006.01) | |
| *A61K 31/221* | (2006.01) | |
| *A61K 31/275* | (2006.01) | |
| *A61K 31/381* | (2006.01) | |
| *A61K 45/06* | (2006.01) | |
| *A61P 11/00* | (2006.01) | |
| *C07C 229/30* | (2006.01) | |
| *C07C 255/07* | (2006.01) | |
| *C07D 277/30* | (2006.01) | |
| *C07D 333/24* | (2006.01) | |

(52) U.S. Cl.
CPC ........ *A61K 31/4164* (2013.01); *A61K 31/197* (2013.01); *A61K 31/198* (2013.01); *A61K 31/216* (2013.01); *A61K 31/221* (2013.01); *A61K 31/275* (2013.01); *A61K 31/381* (2013.01); *A61K 45/06* (2013.01); *A61P 11/00* (2018.01); *C07C 229/30* (2013.01); *C07C 255/07* (2013.01); *C07D 277/30* (2013.01); *C07D 333/24* (2013.01)

(58) Field of Classification Search
CPC ................................................. A61K 31/4164
See application file for complete search history.

(56) References Cited

U.S. PATENT DOCUMENTS

| | | | |
|---|---|---|---|
| 4,423,064 A | 12/1983 | Wheeler | |
| 7,785,825 B2 | 8/2010 | van der Donk et al. | |
| 10,227,314 B2 | 3/2019 | Duron et al. | |
| 10,688,096 B2* | 6/2020 | Snyder | A61K 31/409 |
| 2013/0131028 A1* | 5/2013 | Snyder | A61K 31/198 |
| | | | 514/363 |
| 2015/0272934 A1 | 10/2015 | Stein et al. | |

FOREIGN PATENT DOCUMENTS

| | | |
|---|---|---|
| CN | 101132777 | 2/2008 |
| CN | 101636154 | 1/2010 |
| WO | WO 2006/100479 | 9/2006 |
| WO | WO 2011/130181 | 10/2011 |
| WO | WO 2014/018569 | 1/2014 |
| WO | WO 2014/018571 | 1/2014 |

OTHER PUBLICATIONS

Synder et al. CAS: 167:263283, 2016.*
"(2S,3R)-2-Amino-3-methyl-4-pentynoic acid." PubChem, https://pubchem.ncbi.nlm.nih.gov/compound/101255887#section=Top. Accessed Feb. 6, 2018, 7 pages.
"(2S,3S)-2-Amino-3-Methylpent-4-Ynoic Acid." PubChem, https://pubchem.ncbi.nim.nih.gov/compound/10261097#section=Top. Accessed Feb. 5, 2018, 8 pages.
"(S)-2-Aminohex-4-ynoic acid." PubChem, https://pubchem.ncbi.nlm.nih.gov/compound/10654237#section=Top. Accessed Feb. 5, 2018, 8 pages.
Alonso et al., "Improved preparation of β-hydroxy-α-amino acids: direct formation of sulfates by sulfuryl chloride" Tetrahedron: Asymmetry 2005, 16, 3908-3912.
International Search Report and Written Opinion issued in corresponding PCT Application No. PCT/US2017/67689, dated Mar. 29, 2018.
Office Action and Search Report Issued in corresponding Chinese Application No. 201780086951.7, dated Apr. 19, 2022 (English Translation provided).
"(2S,3R)-2-Amino-3-methyl-4-pentynoic acid." PubChem, Dec. 18, 2015, pp. 1-7 [online]. https://pubchem.ncbi.nlm.nih.gov/compound/101255887#section=Top. Accessed Feb. 6, 2018, 7 pages.
"(2S,3S)-2-Amino-3-Methylpent-4-Ynoic Acid." PubChem, Oct. 25, 2006, pp. 1-8 [online]. https://pubchem.ncbi.nlm.nih.gov/compound/10261097#section=Top. Accessed Feb. 5, 2018, 8 pages.
"(S)-2-Aminohex-4-ynoic acid." PubChem, Oct. 25, 2006, pp. 1-8 [online]. https://pubchem.ncbi.nlm.nih.gov/compound/10654237#section=Top. Accessed Feb. 5, 2018, 8 pages.

(Continued)

*Primary Examiner* — Rei Tsang Shiao
(74) *Attorney, Agent, or Firm* — Norton Rose Fulbright US LLP

(57) ABSTRACT

Described herein are novel γ- and δ-propargyl carboxylic acids and esters. The novel compositions are antagonists of CSE and may be used to modulate of the activity of the carotid body, therefore providing therapeutic benefits for sleep-related breathing disorders and related conditions.

25 Claims, 16 Drawing Sheets

(56) References Cited

OTHER PUBLICATIONS

Inoue, et al., "Clinical Efficacy and indication of acetazolamide treatment on sleep apnea syndrome", Psychiatry and Clinical Neurosciences, 53(2), pp. 321-322, 1999.
Supplementary Partial European Search Report in corresponding European Application No. EP 17884341, dated Jun. 17, 2020.

* cited by examiner

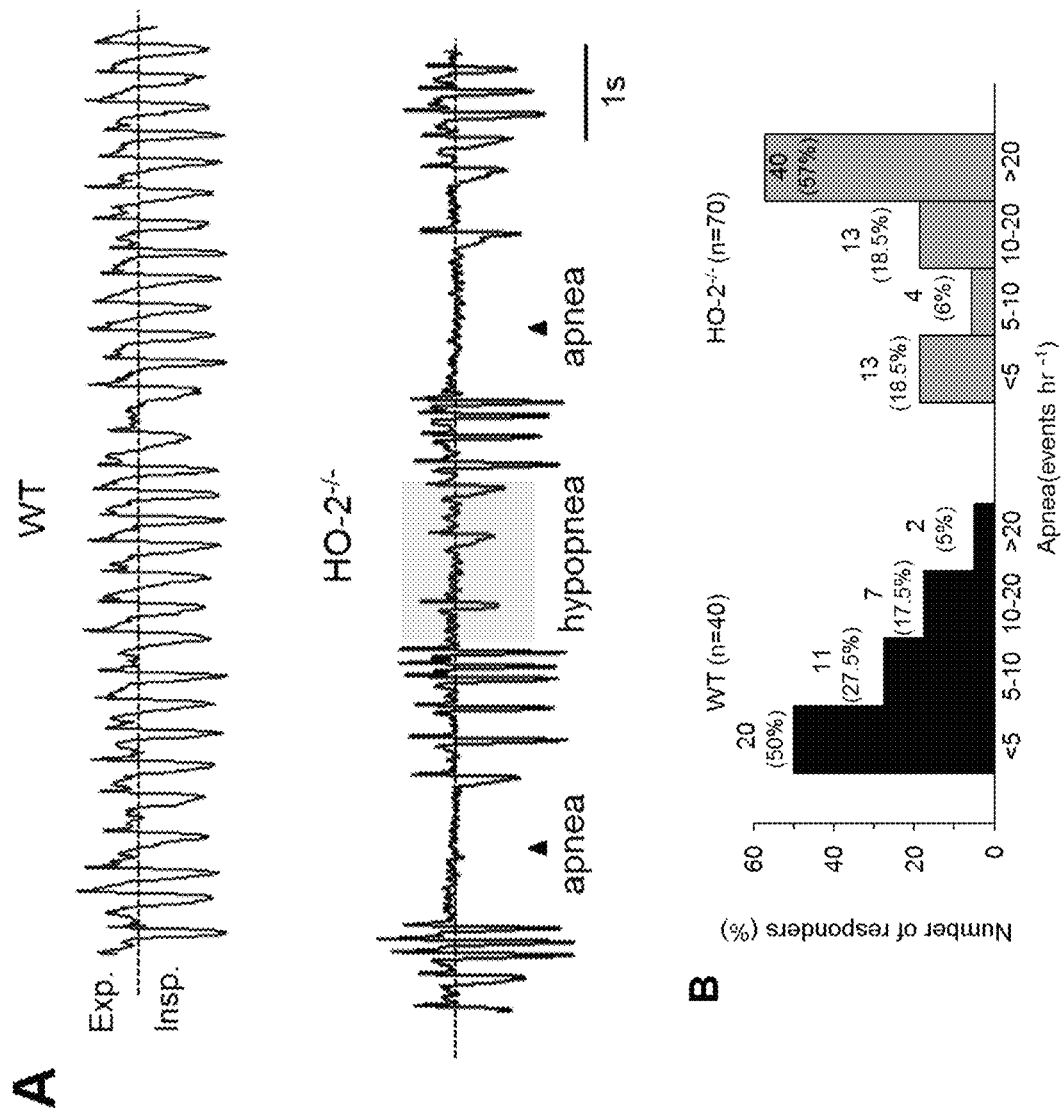
FIG. 1A-B

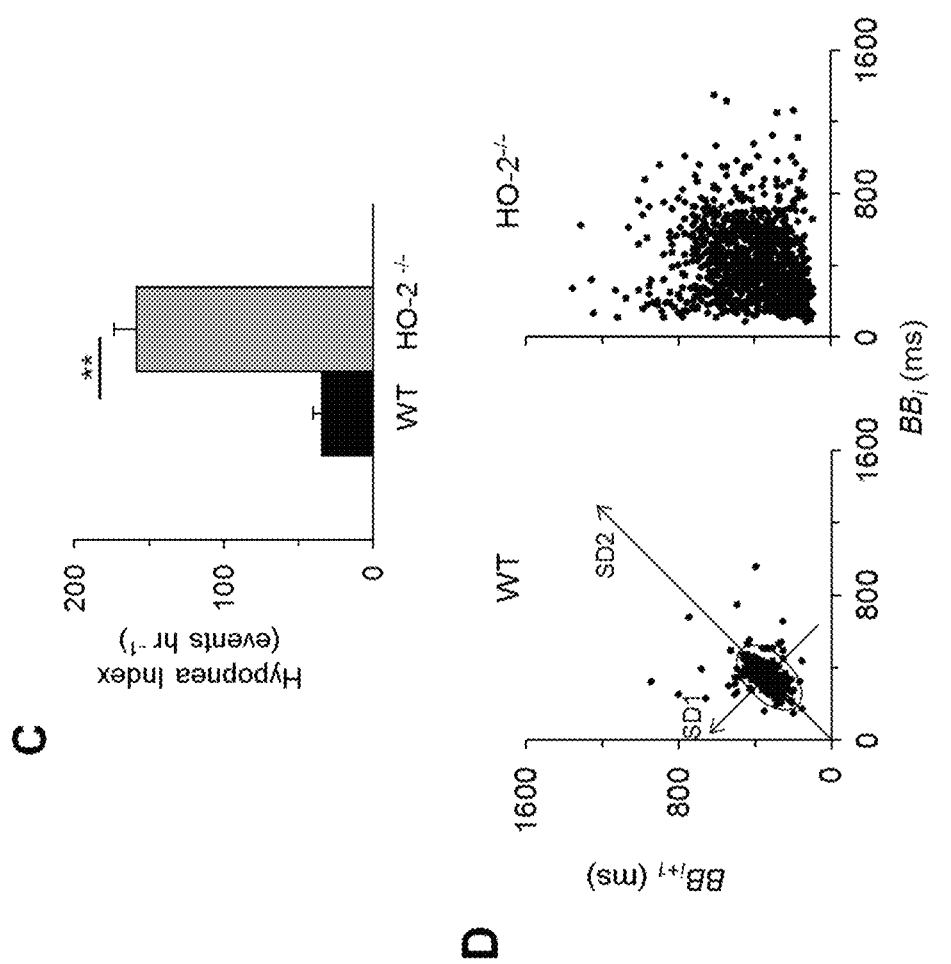
FIG. 1C-D

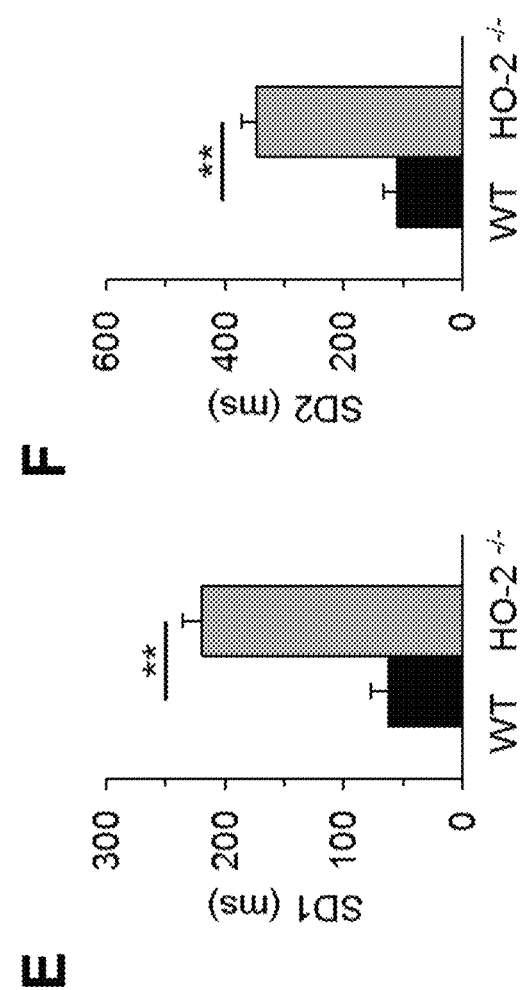
FIG. 1E-F

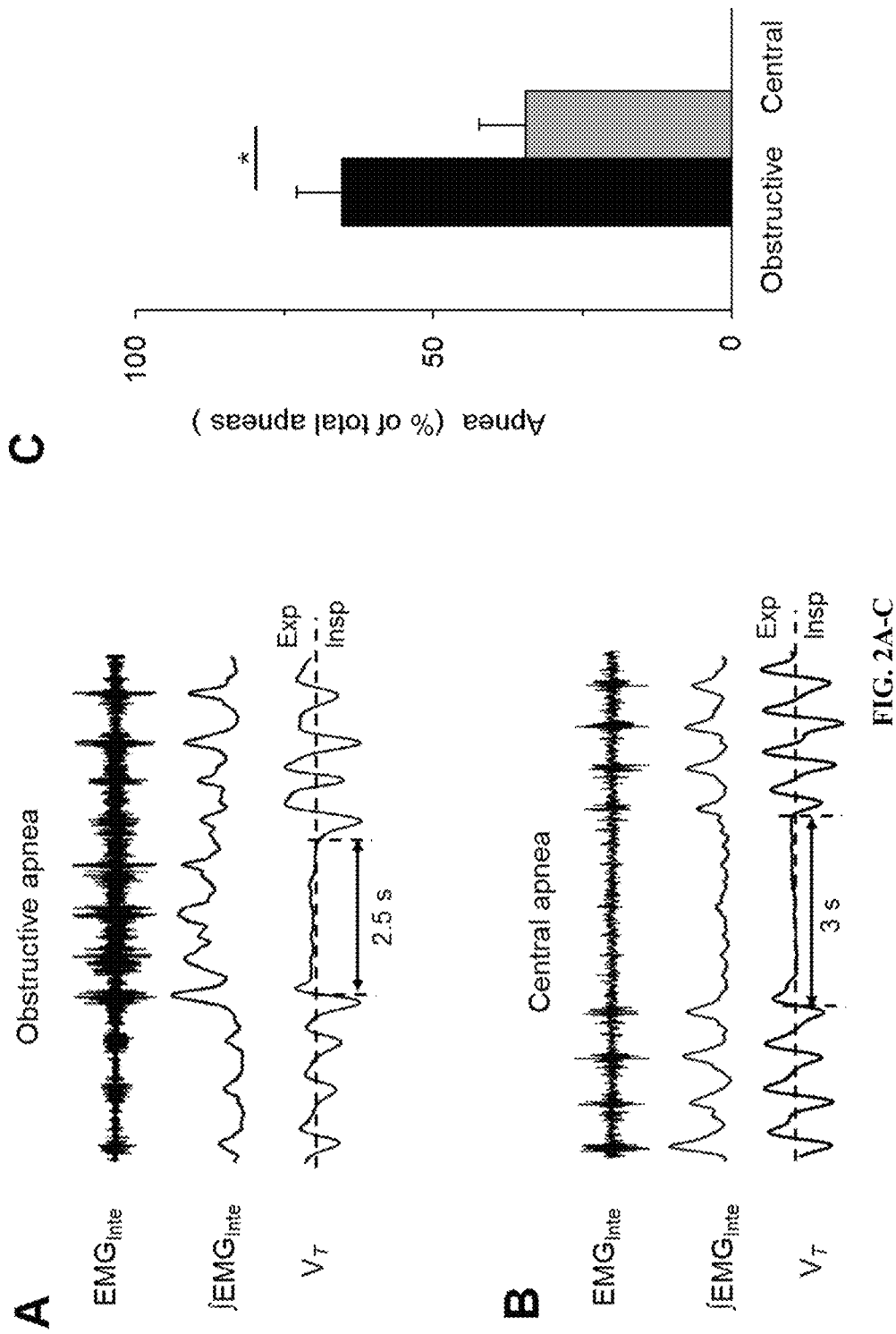
FIG. 2A-C

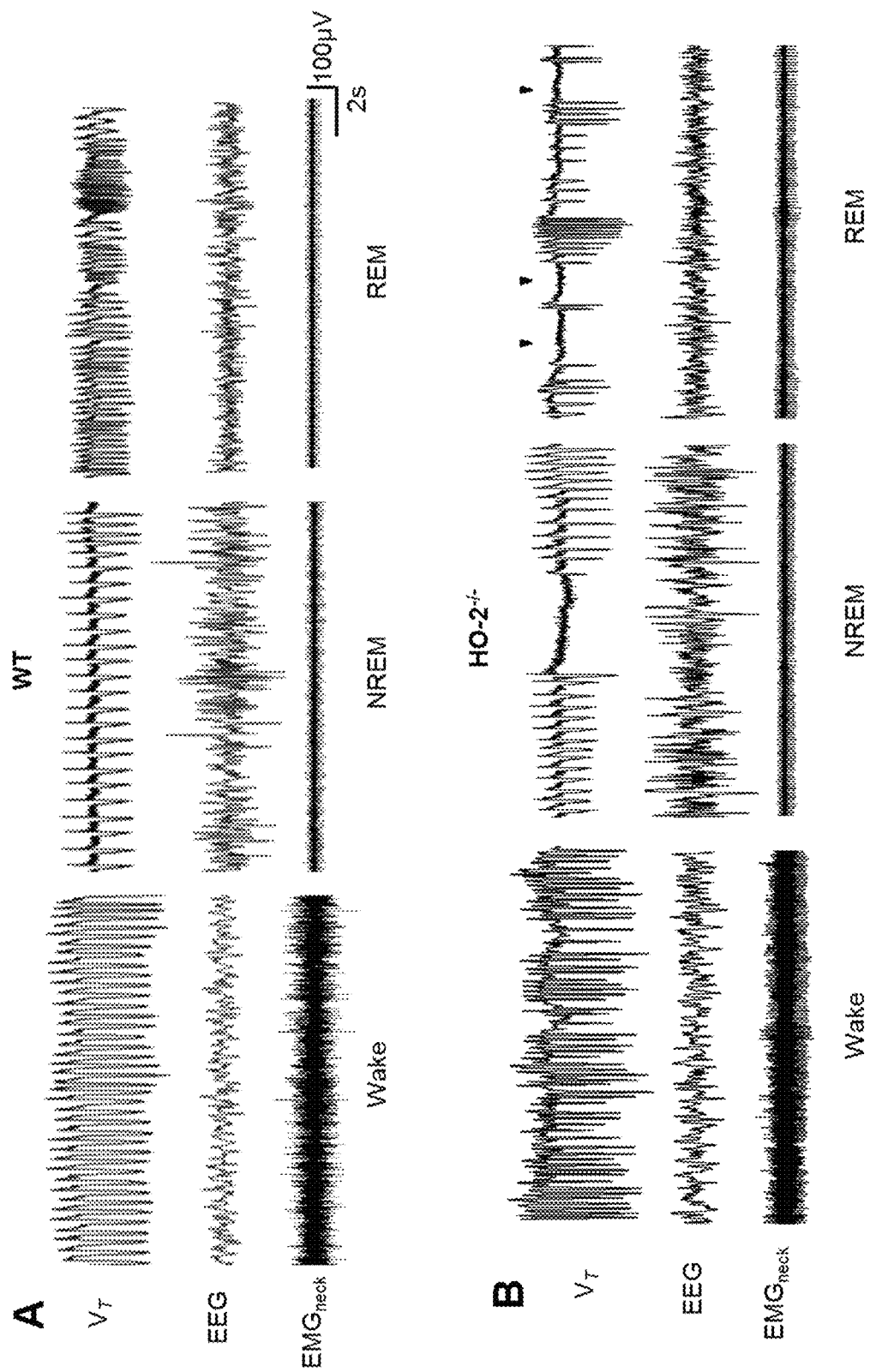
FIG. 3A-B

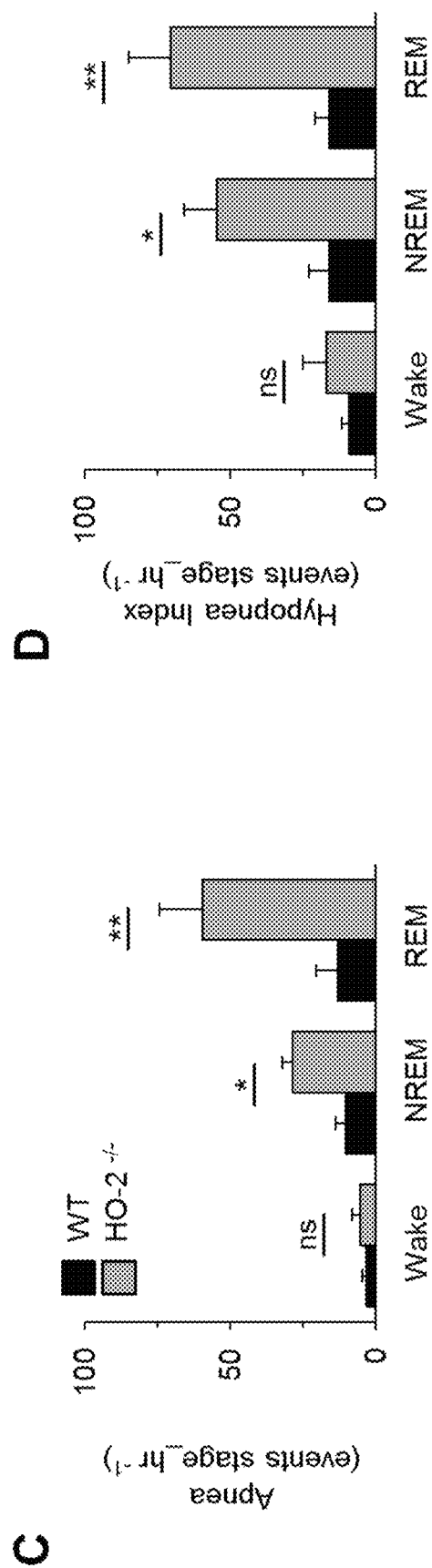
FIG. 3C-D

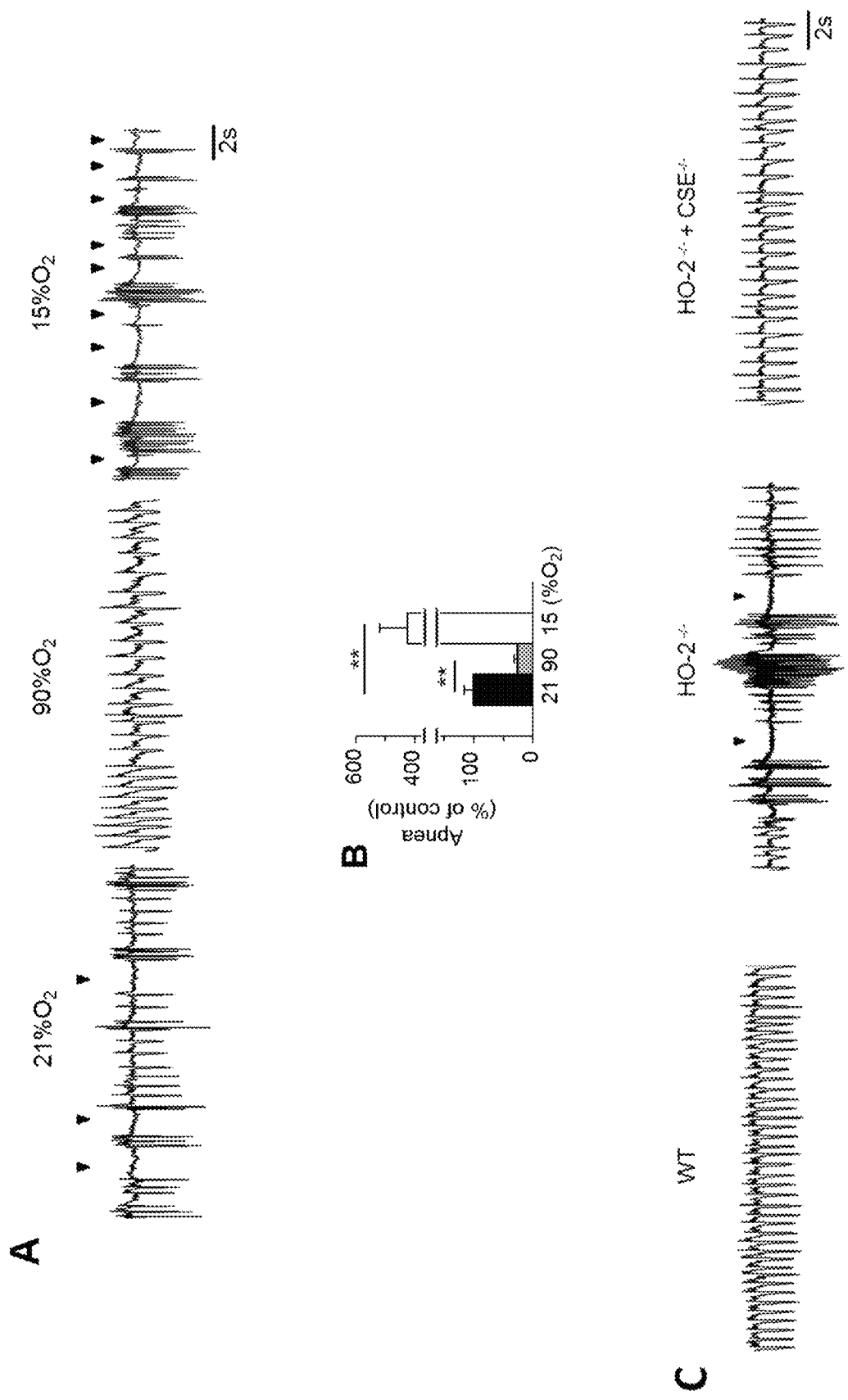
FIG. 4A-C

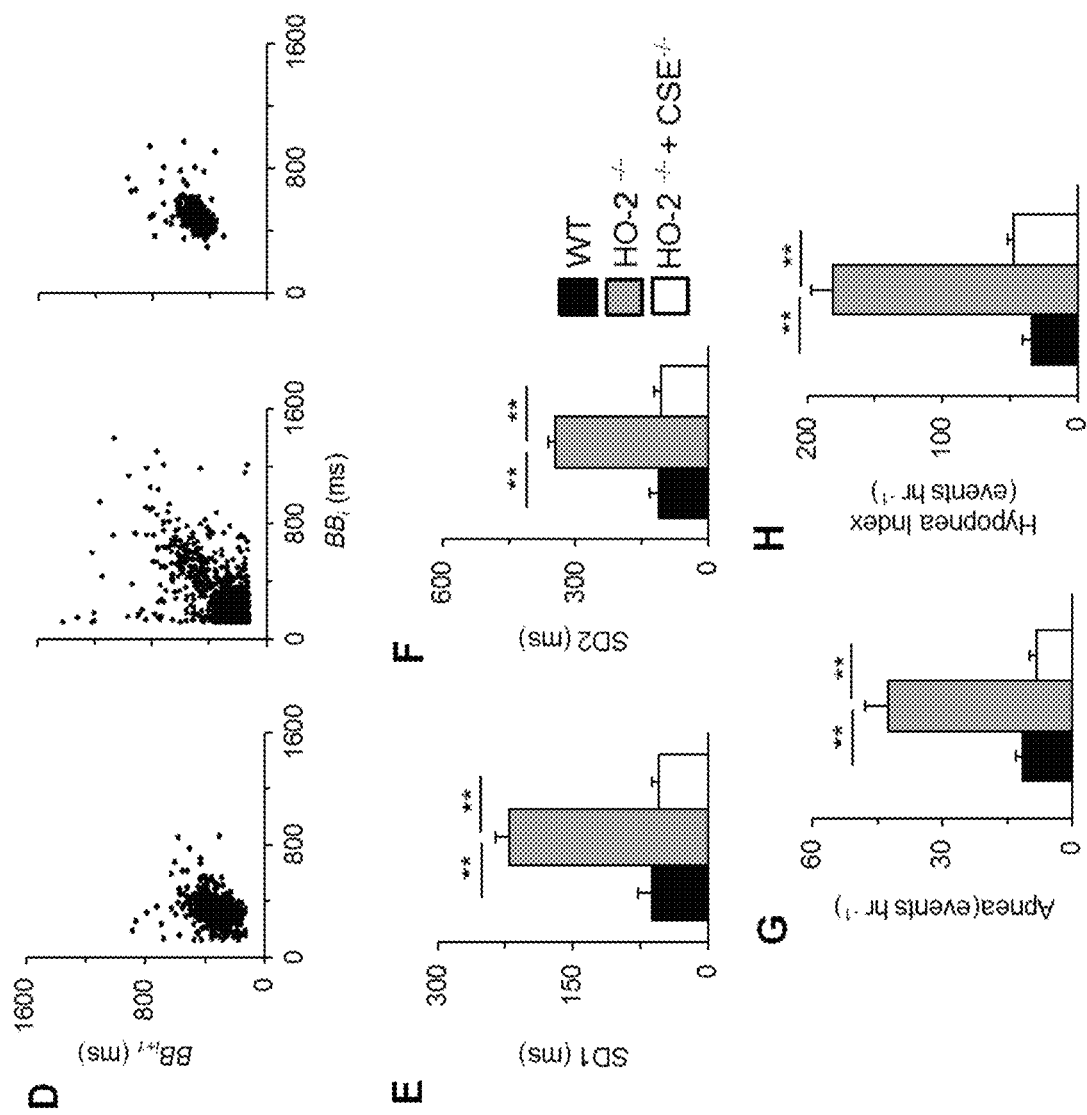
FIG. 4D-H

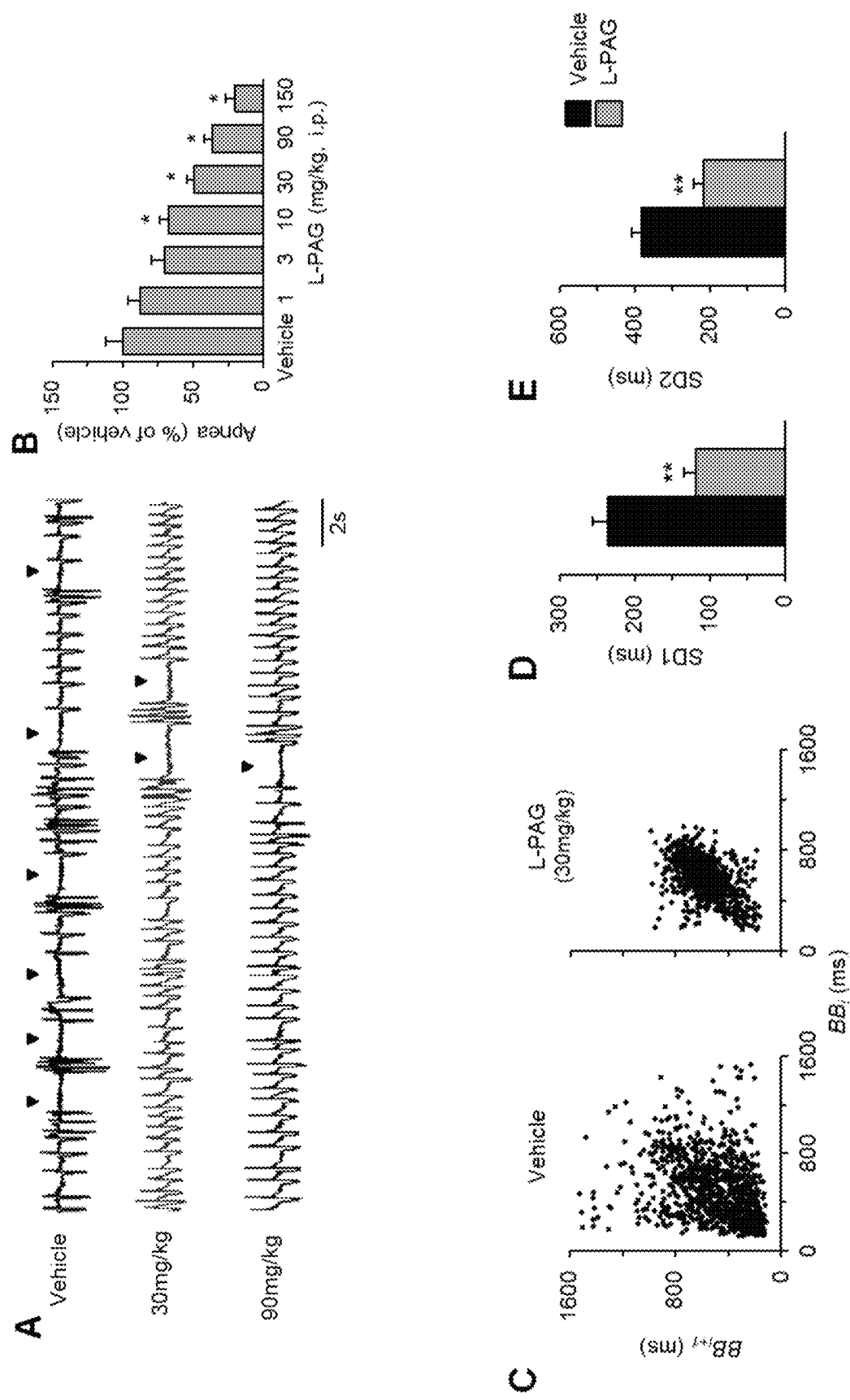
FIG. 5A-E

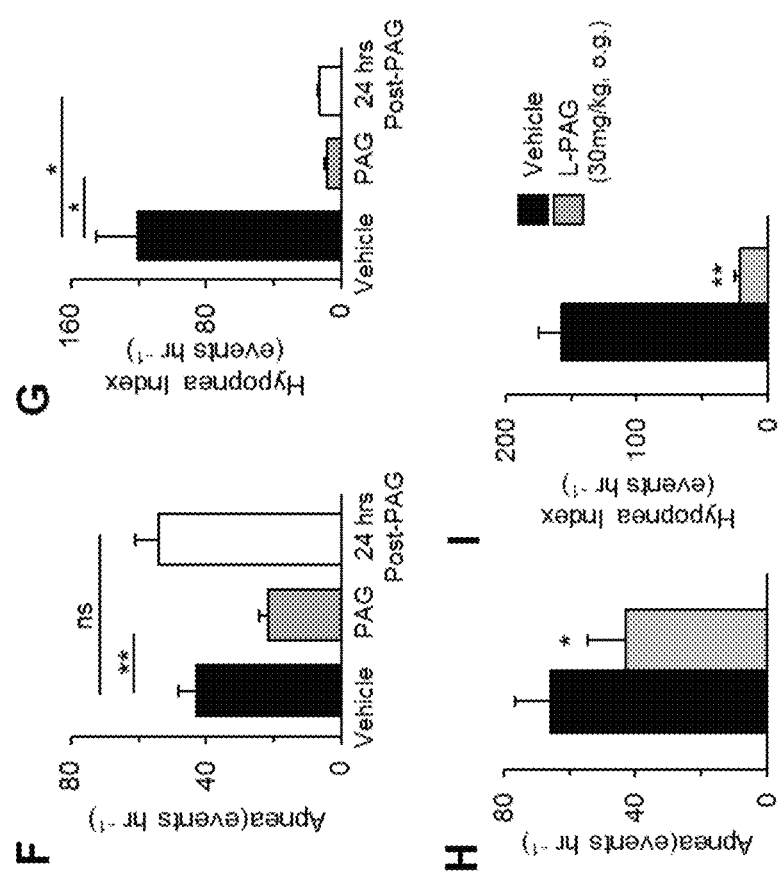
FIG. 5F-I

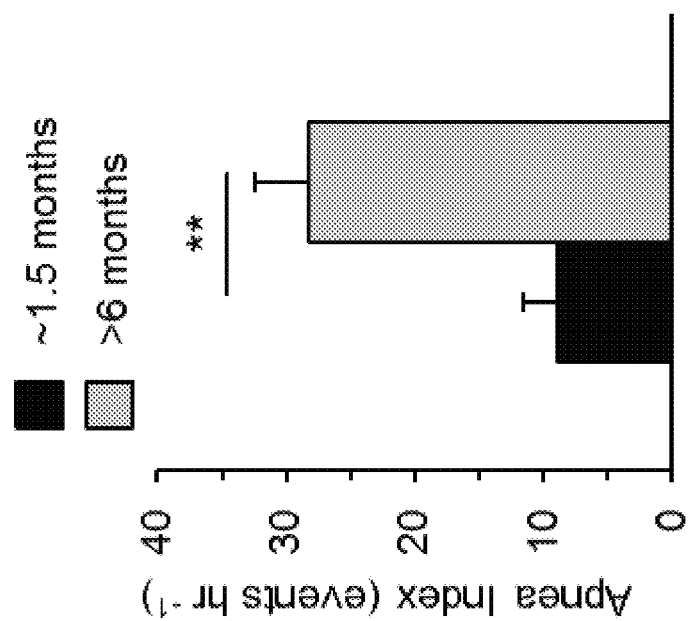
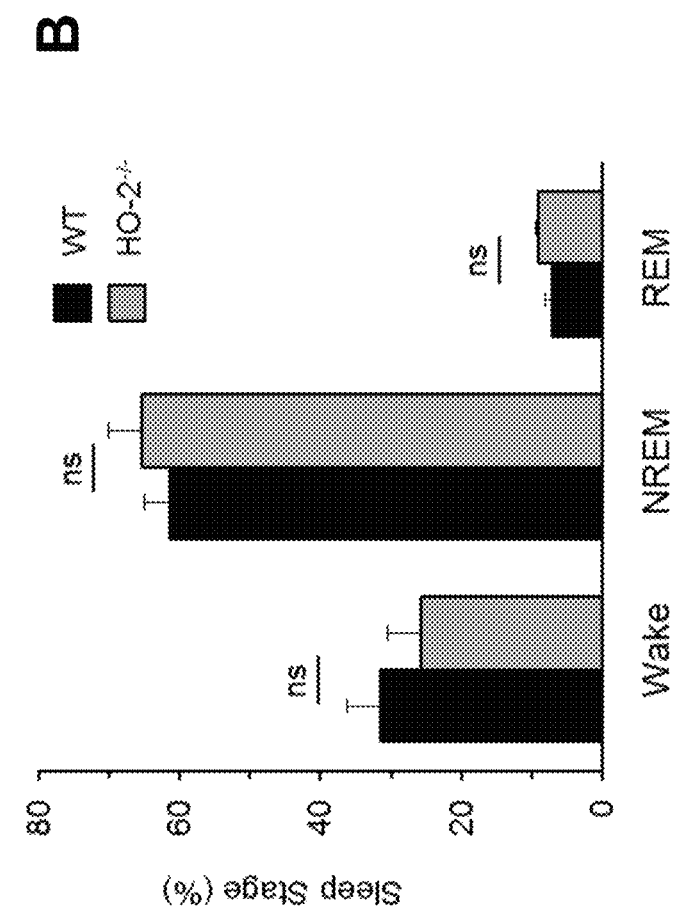
FIG. 6A-B

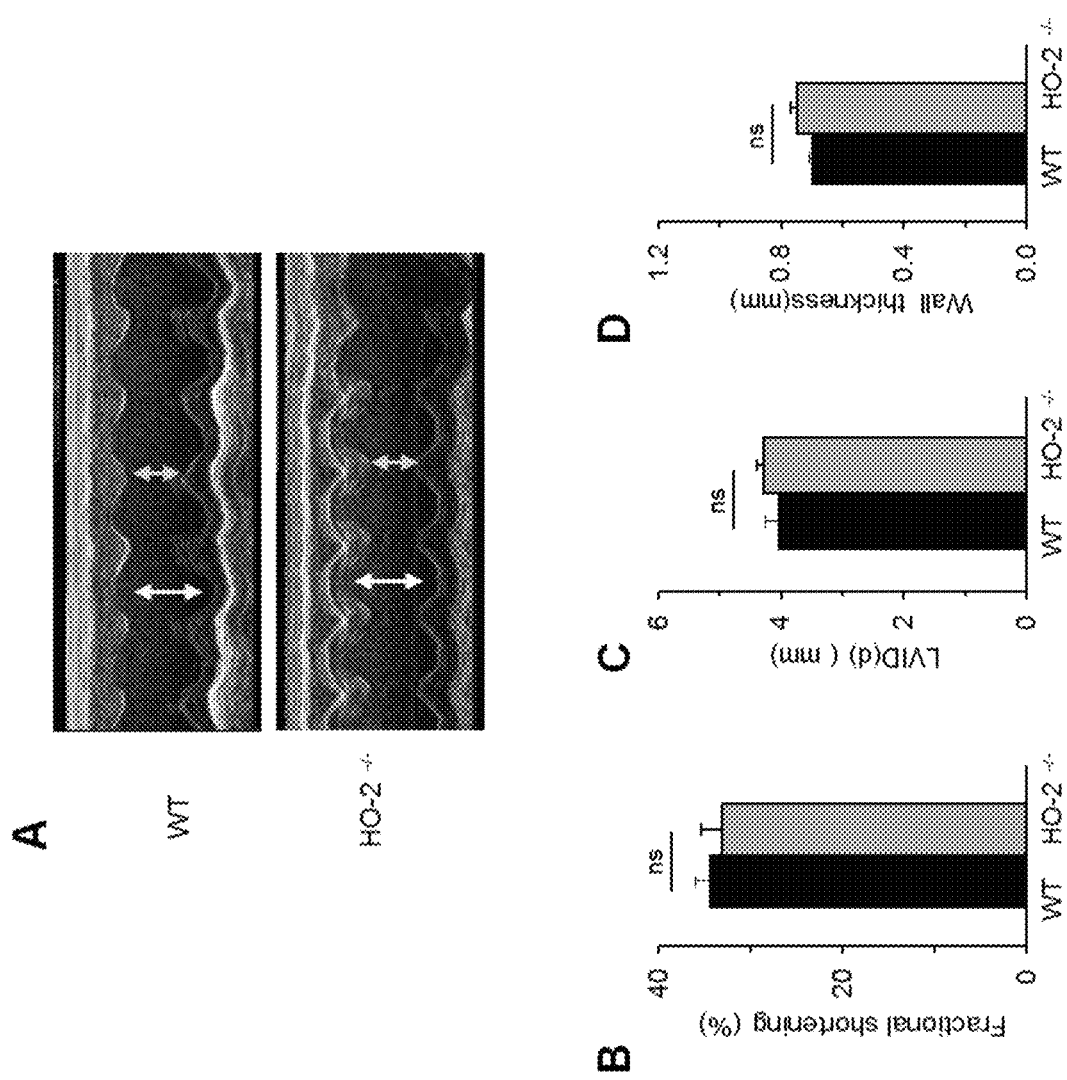
FIG. 7A-D

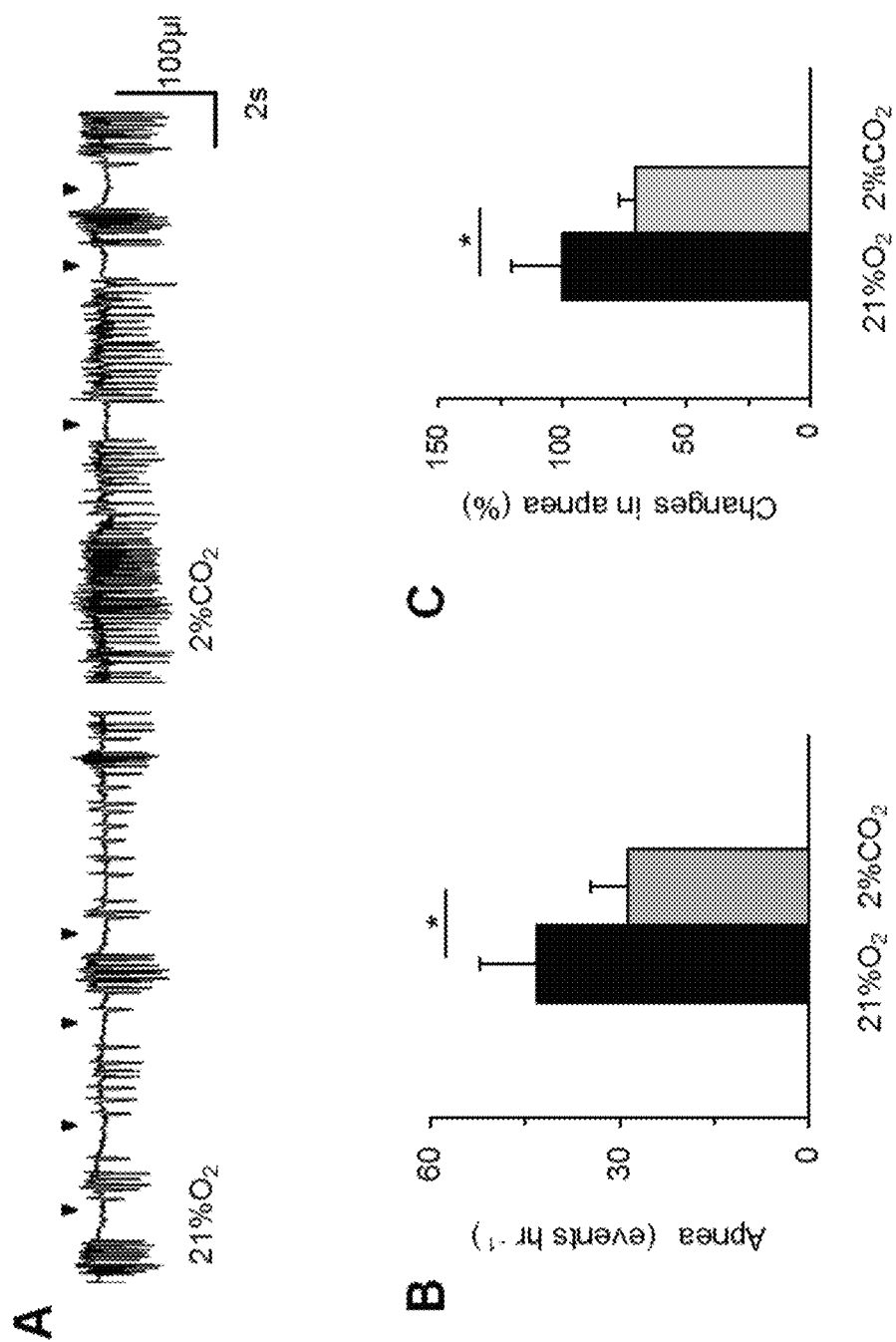
FIG. 8A-C

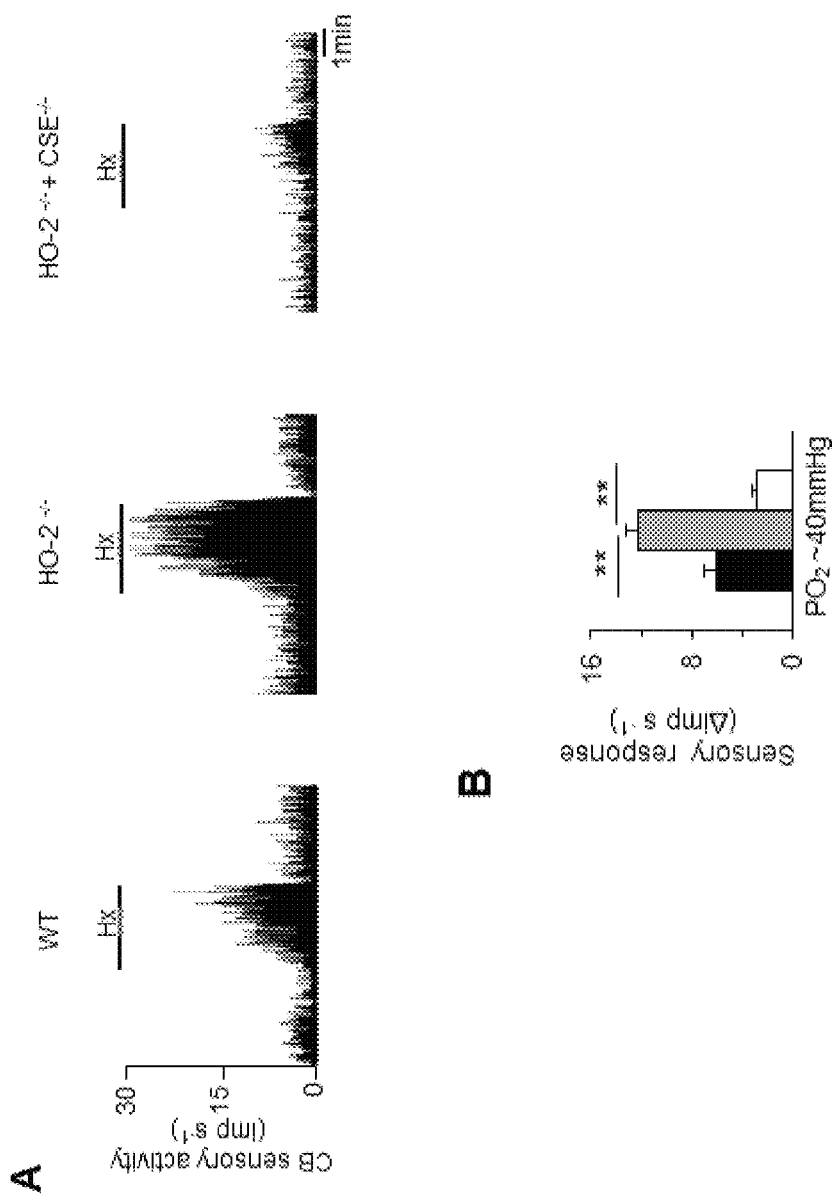
FIG. 9A-B

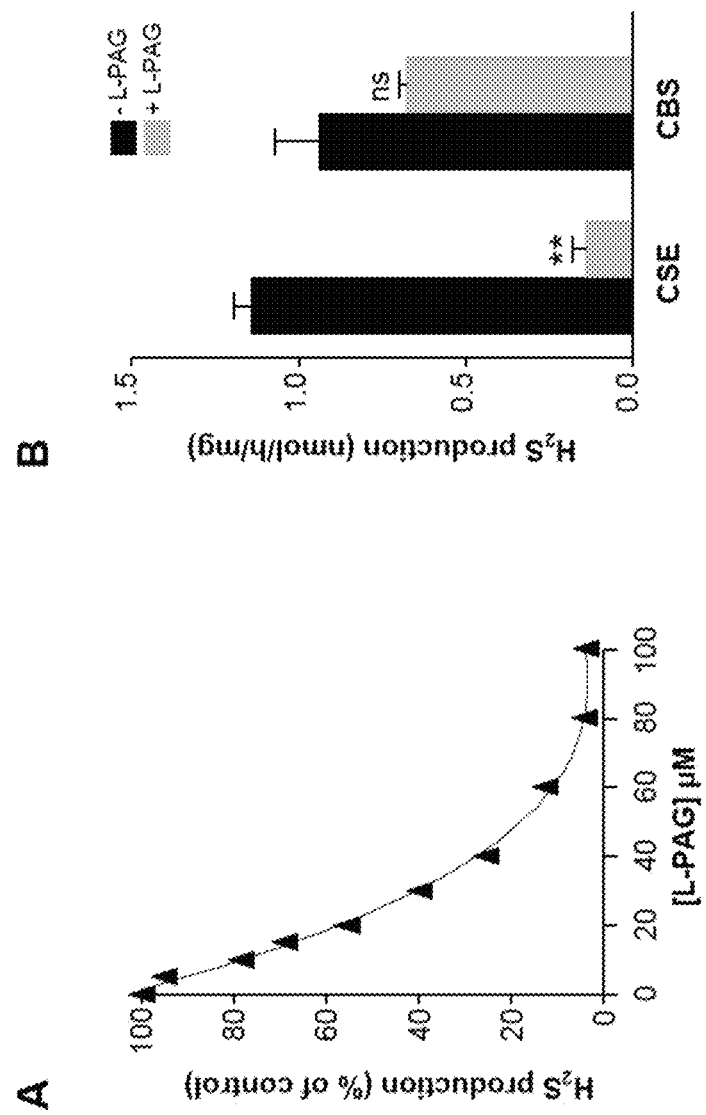
FIG. 10A-B

L-PAG DERIVATIVES FOR TREATMENT OF SLEEP DISORDERED BREATHING (SDB)

CROSS-REFERENCE TO RELATED APPLICATIONS

This application is a continuation of U.S. patent application Ser. No. 15/929,512 filed May 6, 2020, which is a continuation of U.S. patent application Ser. No. 16/470,445 filed Jun. 17, 2019, which is a national phase application under 35 U.S.C. § 371 of International Application No. PCT/US2017/067689 filed Dec. 20, 2017, which claims the benefit of priority of U.S. Provisional Patent Application No. 62/436,942 filed Dec. 20, 2016, all of which are hereby incorporated by reference in their entirety.

STATEMENT OF GOVERNMENTAL SUPPORT

The invention was made with government support under Grant No. 4UH3 HL123610-03 awarded by the National Institutes of Health. The government has certain rights in the invention.

FIELD OF THE INVENTION

The invention relates to the field of medicine, pharmacology, and synthetic organic chemistry. More specifically, it concerns methods and compositions involving a cystathionine-γ-lyase (CSE) antagonist for preventing, treating, and/or reducing symptoms of sleep-related disorders and conditions.

BACKGROUND

Sleep apnea is a respiratory disorder characterized by periodic cessation of breathing (apnea) during sleep. Sleep apnea is caused by obstruction of the upper airway (obstructive sleep apnea or OSA) or disrupted respiratory rhythm generation by the central nervous system (central sleep apnea or CSA). OSA can be caused by deposition of adipose tissue in the upper airway or changes in the characteristics of the hyoid bone, soft palate, nasopharynx and oropharynx. Development of sleep apnea has been observed in both obese and non-obese individuals and can be diagnosed by methods including but not limited to polysomnography. In CSA, the brain stem is less sensitive to changes in the carbon dioxide level. As a consequence, people who have CSA breathe less deeply and more slowly than normal. Using an opioid, being at high altitude or the presence of a brain tumor, though rare, can be a cause of CSA. Unlike OSA, central sleep apnea is not associated with obesity. In one form of CSA, called Ondine's curse, which usually occurs in newborns, people may breathe inadequately or not at all except when they are fully awake. Sleep apnea is a highly prevalent disorder that affects an estimated 10% of the adult human population (Peppard, 2013). Patients with sleep apnea exhibit a wide spectrum of pathologies including hypertension, stroke, neurocognitive and metabolic dysfunctions and disrupted sleep.

The carotid body is a sensory organ that detects acute changes in arterial blood oxygen ($O_2$) levels and reflexively mediates systemic cardiac, vascular, and respiratory responses to hypoxia. Although the mechanisms of carotid body sensing are not known, studies show that hydrogen sulfide ($H_2S$) acts as a carotid gasotransmitter, enhancing its sensory response to hypoxia. Clinical studies suggest that enhanced carotid body chemoreflex contributes in part to the genesis of apnea and the downstream pathologies caused by intermittent deficiency in the amount of oxygen reaching the tissues (hypoxia). Exaggerated carotid body response to hypoxia is observed in mice lacking hemeoxygenase-2 (HO-2), an enzyme responsible for the generation of endogenous carbon monoxide (CO). This effect is mediated by augmented cystathionine-γ-lyase (CSE) derived hydrogen sulfide ($H_2S$) signaling in the carotid body.

Continuous positive airway pressure (CPAP) is the present treatment of choice for OSA and adaptive servo-ventilation is considered beneficial for CSA patients. However, a substantial number of OSA patients do not respond to CPAP therapy (McEvoy, 2016). Adaptive ventilation in heart failure patients exhibiting CSA showed 30% mortality with no demonstrable benefits for CSA (Cowie, 2015). The estimated cost burden in unmanaged sleep apnea patients is extremely high; estimates range from approximately $65-165 billion per year in the U.S. Thus, available evidence suggest that current therapies are not effective in preventing co-morbidities associated with either OSA or CSA and highlight the need for alternative strategies for preventing sleep apnea and associated pathologies. There exists a need for therapeutic agents that attenuate carotid body chemoreflex for treatment of sleep-related breathing disorders such as OSA and CSA.

SUMMARY OF THE INVENTION

Disclosed herein are methods and composition involving antagonists of cystathionine γ-lyase (CSE), including propargyl (2-propynyl) and homopropargyl (3-butynyl) substituted amino acids and esters. Propargyl-substituted and homo-propargyl-substituted amino acids and esters reduce CSE-catalyzed synthesis of hydrogen sulfide ($H_2S$). The CSE antagonists disclosed herein may be used to treat, prevent, or reduce sleep-related breathing disorders.

In some embodiments, methods and compositions concern a CSE antagonist that causes one or more physiological effects. In some embodiments it reduces or attenuates CSE-catalyzed synthesis of $H_2S$. In some aspects, reduced synthesis of $H_2S$ results in attenuation of carotid body chemoreflex. In further aspects, a CSE antagonist reduces chemosensitivity of the carotid body to arterial blood oxygen and/or arterial blood carbon dioxide. Reduced carotid body chemosensitivity reduces loop gain of the ventilator drive control system, blunts hypoventilation, lowers blood pressure, and/or dampens carotid sinus nerve activity, in some aspects. In some embodiments, a CSE antagonist bolsters the carotid body's response to hypoxia. In further embodiments, the CSE antagonist had an anti-apneic effect within or after 10, 20, 30, 40, 50, 60, 70, 80, 90, 100, 110, 120, 130, 140, 150 minutes (or any range derivable therein) of administration. In some embodiments, the effects of ED 50 dose was fully reversed after at least or at most 12, 13, 14, 15, 16, 17, 18, 19, 20, 21, 22, 23, 24, 25, 26, 27, 28, 29, or 30 hours (or any range derivable therein). Furthermore, in additional embodiments, there was an absence of any visible toxicity due to the administered drug.

In some embodiments, a method of treating, preventing, or reducing a sleep-related breathing disorder in an individual in need thereof comprising administering a therapeutically effective amount of a cystathionine-γ-lyase (CSE) antagonist, wherein the CSE antagonist is a compound of formula (I):

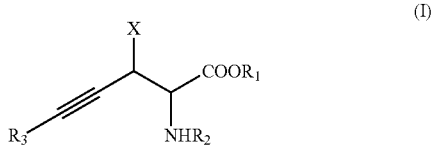

(I)

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, and X is a hydrogen, a halide, nitrile, substituted or unsubstituted alkyl, substituted or unsubstituted aryl, substituted or unsubstituted heteroaryl, a substituted or unsubstituted heterocycle. In additional embodiments, one or more of these species may be excluded. In some embodiments, a CSE antagonist is a pharmaceutically acceptable salt, enantiomer, diastereomer, or prodrug of a compound represented by formula (I).

In some embodiments, a method of treating, preventing, or reducing a sleep-related breathing disorder in an individual in need thereof comprising administering a therapeutically effective amount of a cystathionine-γ-lyase (CSE) antagonist, wherein the CSE antagonist is a compound of formula (II):

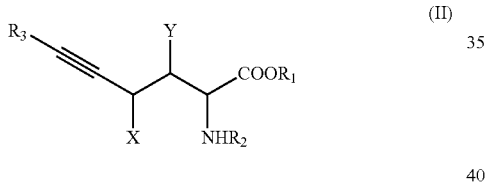

(II)

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycleX is hydrogen, a halide, nitrile, substituted or unsubstituted alkyl, substituted or unsubstituted aryl, substituted or unsubstituted heteroaryl, a substituted or unsubstituted heterocycle, and Y is hydrogen, substituted or unsubstituted alkyl, substituted or unsubstituted aryl, substituted or unsubstituted heteroaryl, substituted or unsubstituted heterocycle, or an electron-donating group. In additional embodiments, one or more of these species may be excluded. In some embodiments, a CSE antagonist is a pharmaceutically acceptable salt, enantiomer, diastereomer, or prodrug of a compound represented by formula (II).

In some embodiments, a method of treating, preventing, or reducing a sleep-related breathing disorder in an individual in need thereof comprising administering a therapeutically effective amount of a cystathionine-γ-lyase (CSE) antagonist, wherein the CSE antagonist is a compound of formula (III):

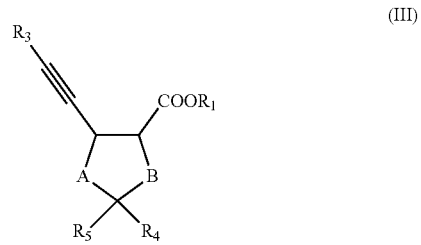

(III)

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_4$ and $R_5$ are each independently hydrogen, substituted or unsubstituted alkyl, substituted or unsubstituted aryl, or join to form a 3- to 6-membered substituted or unsubstituted cycloalkyl or heterocycle, and A and B are each independently O, NH, $SO_2$, or $CH_2$. In additional embodiments, one or more of these species may be excluded. In some embodiments, a CSE antagonist is a pharmaceutically acceptable salt, enantiomer, diastereomer, or prodrug of a compound represented by formula (III).

In some embodiments, a method of treating, preventing, or reducing a sleep-related breathing disorder in an individual in need thereof comprising administration of a therapeutically effective amount of a cystathionine-γ-lyase (CSE) antagonist, wherein the CSE antagonist is a compound of formula (IV):

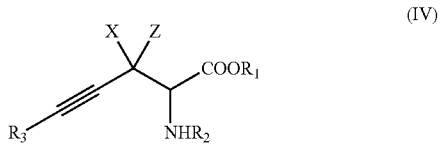

(IV)

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, and X and Z are each independently hydrogen, a halide, nitrile, substituted or unsubstituted alkyl, substituted or unsubstituted aryl, substituted or unsubstituted heteroaryl, or a substituted or unsubstituted heterocycle. In additional embodiments, one or more of these species may be excluded. In some embodiments, a CSE antagonist is a pharmaceutically acceptable salt, enantiomer, diastereomer, or prodrug of a compound represented by formula (IV).

In certain embodiments, a method of treating, preventing, or reducing a sleep-related breathing disorder in an individual in need thereof comprising administration of a therapeutically effective amount of a cystathionine-γ-lyase (CSE) antagonist, wherein the CSE antagonist is a compound of formula (V):

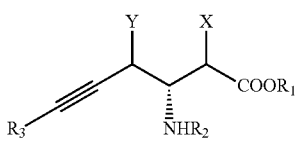

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, X is hydrogen, a halide, nitrile, substituted or unsubstituted alkyl, substituted or unsubstituted aryl, substituted or unsubstituted heteroaryl, a substituted or unsubstituted heterocycle, and Y is hydrogen, halide, nitrile, substituted or unsubstituted alkyl, substituted or unsubstituted aryl, substituted or unsubstituted heteroaryl, substituted or unsubstituted heterocycle, or an electron-donating group. In additional embodiments, one or more of these species may be excluded. In some embodiments, the compound is a salt, enantiomer, or diastereomer of the compound represented by formula (V).

In some aspects, a CSE antagonist may be administered to an individual that is suffering from or suspected to be suffering from a sleep-related breathing disorder, which include the following disorders: central sleep apnea (CSA), Cheyne-Stokes breathing-central sleep apnea (CSB-CSA), obesity hypoventilation syndrome (OHS), congenital central hypoventilation syndrome (CCHS), obstructive sleep apnea (OSA), idiopathic central sleep apnea (ICSA), narcotic-induced CSA, high altitude periodic breathing, chronic mountain sickness, impaired respiratory motor control associated with stroke, upper airway resistance syndrome (UARS), or impaired respiratory motor control associated with a neurologic disorder. In some embodiments, a CSE antagonist is administered orally, subcutaneously, topically, intramuscularly, or intravenously.

It is specifically contemplated that compounds having any of formulas (I), (II), (III), or (IV) may have one or more species discussed herein excluded as an embodiment of the invention.

Certain embodiments are directed to compounds of formula (I)

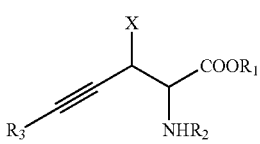

(I)

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$, is hydrogen, acyl, substituted or unsubstituted alkyl, substituted or unsubstituted aryl, substituted or unsubstituted heteroaryl, or a substituted or unsubstituted heterocycle, and X is hydrogen, a halide, nitrile, substituted or unsubstituted alkyl, substituted or unsubstituted aryl, substituted or unsubstituted heteroaryl, or a substituted or unsubstituted heterocycle. In additional embodiments, one or more of these species may be excluded. In some embodiments, the compound is a salt, enantiomer, or diastereomer of the compound represented by formula (I).

In some aspects, the stereochemistry at the α-carbon may be (R) or (S). In further aspects, the stereochemistry at the β-carbon may be (R) or (S). The stereochemistries of the α- and β-carbons may be the same, or may be different. In a particular aspect, $R_1$, $R_2$, and $R_3$ are each hydrogen.

In particular aspects, a compound of formula (I) is at least or at most one of the following:

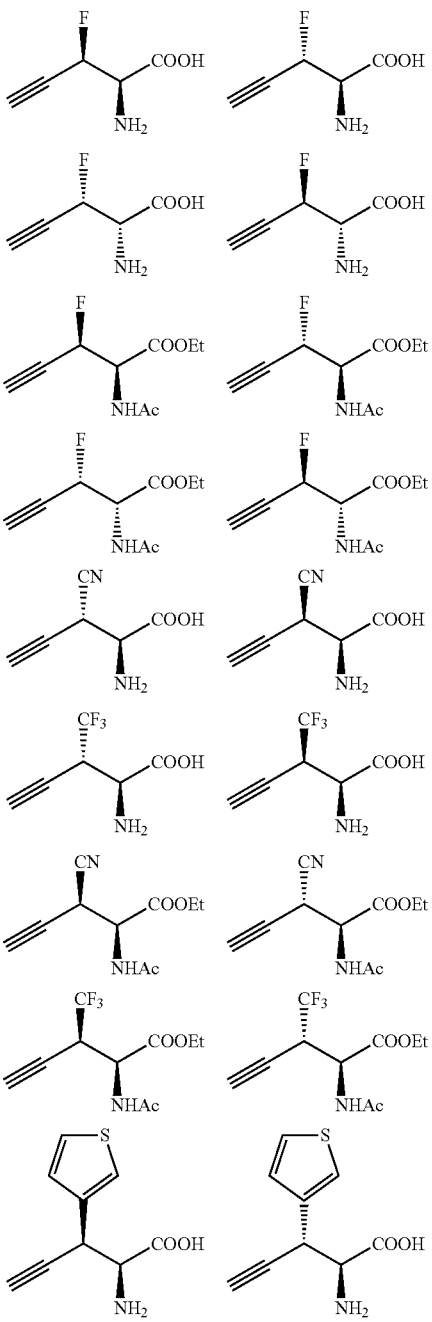

-continued
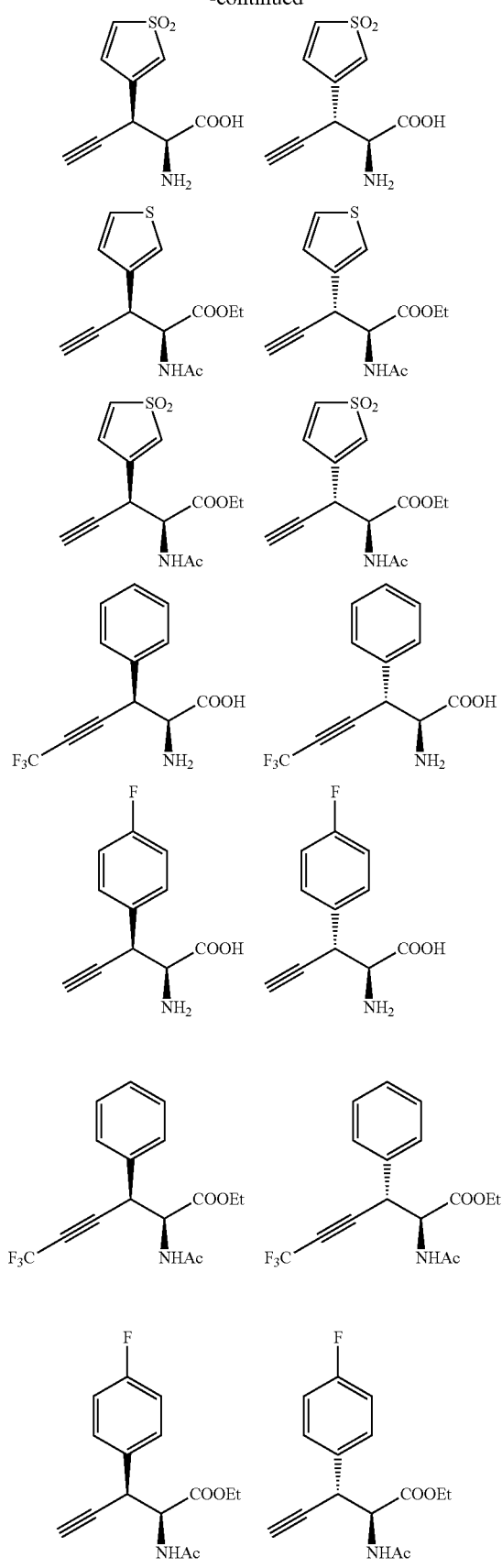
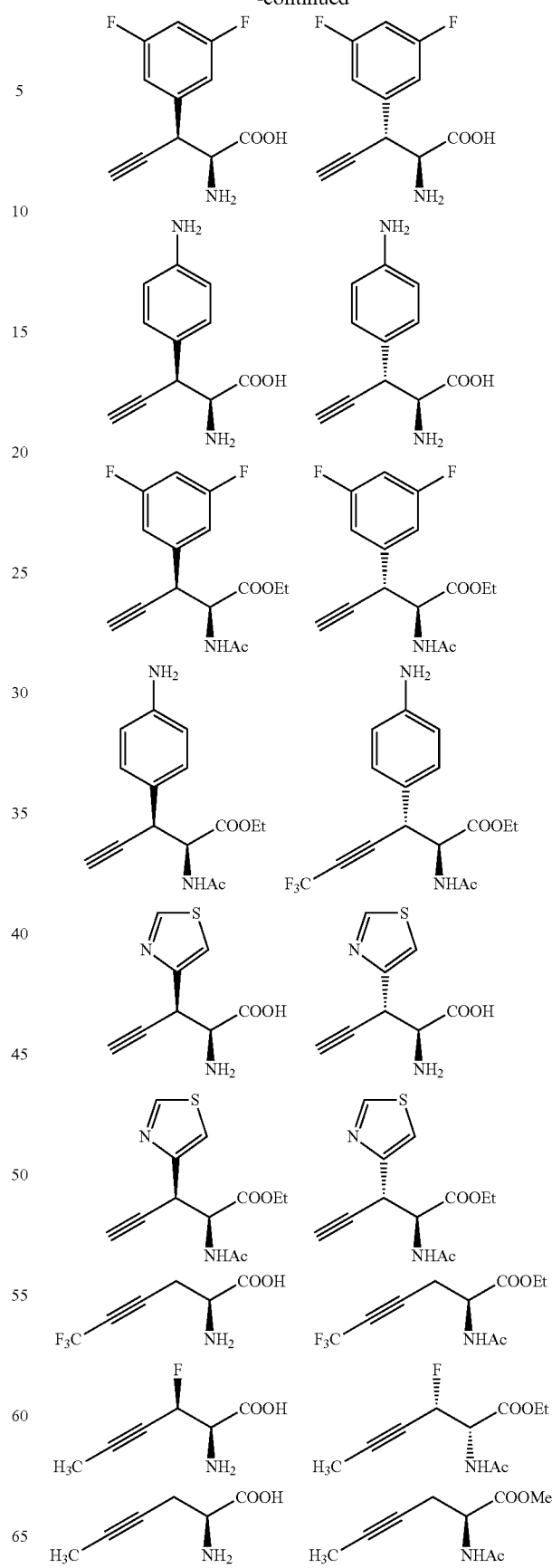

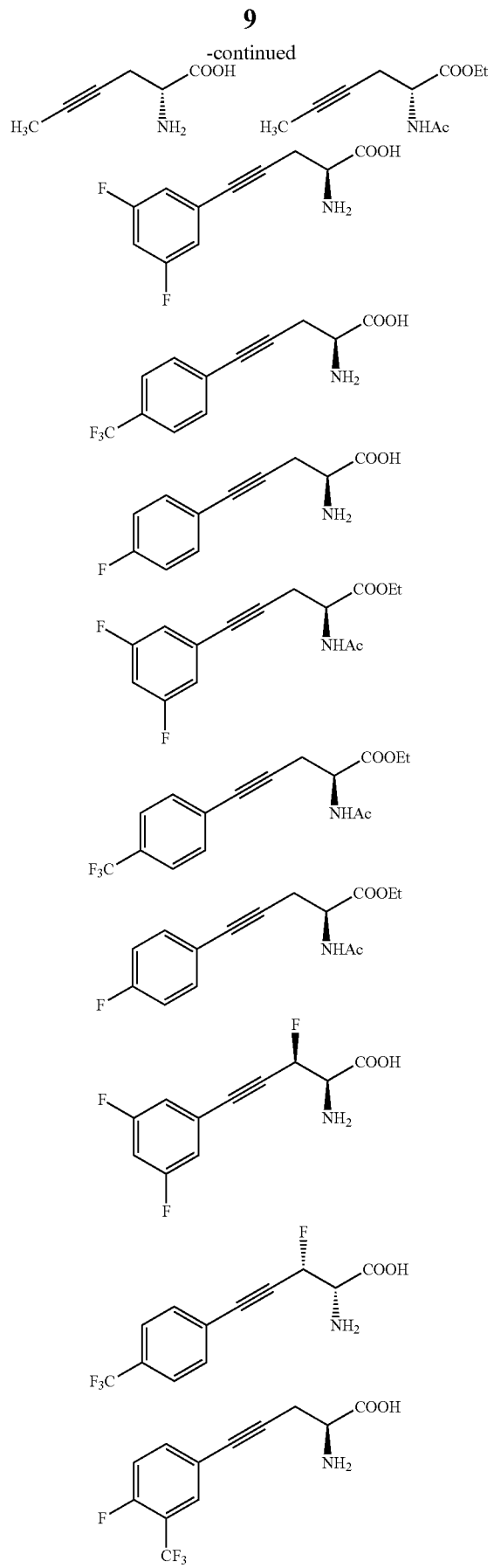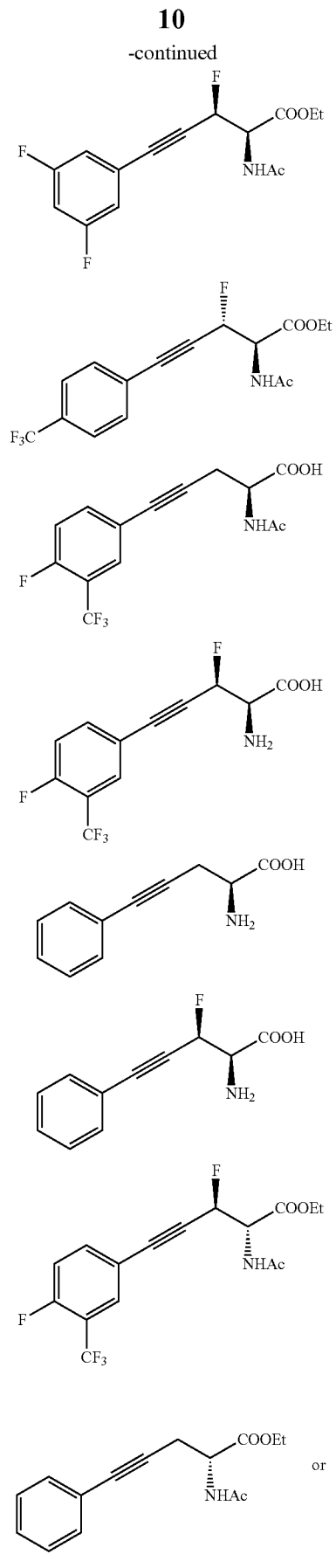

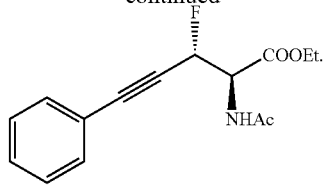

In other embodiments, one or more of these compounds may be excluded as an embodiment.

Certain embodiments are directed to compounds of formula (II)

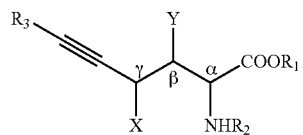

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, X is hydrogen, a halide, nitrile, substituted or unsubstituted alkyl, substituted or unsubstituted aryl, substituted or unsubstituted heteroaryl, a substituted or unsubstituted heterocycle, and Y is hydrogen, substituted or unsubstituted alkyl, substituted or unsubstituted aryl, substituted or unsubstituted heteroaryl, substituted or unsubstituted heterocycle, or an electron-donating group. In additional embodiments, one or more of these species may be excluded. In some embodiments, the compound is a salt, enantiomer, or diastereomer of the compound represented by formula (II).

The stereochemistry of each of the α-, β-, and γ-carbons may each independently be (R) or (S). In some embodiments, the stereochemistries of two of the α- and β- and γ-carbons are different from the stereochemistry of the third chiral carbon. Examples (α, β, γ) include (S, R, S), (R, S, R), (S, S, R), (R, R, S), (S, R, R), and (R, S, S). In other embodiments, the stereochemistries of the α- and β- and γ-carbons are the same, e.g., (R, R, R) and (S, S, S).

In particular aspects, a compound of formula (II) is at least or at most one of the following:

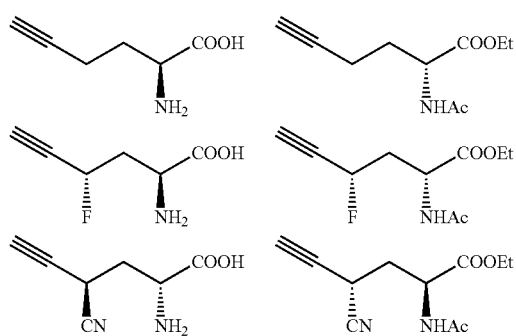

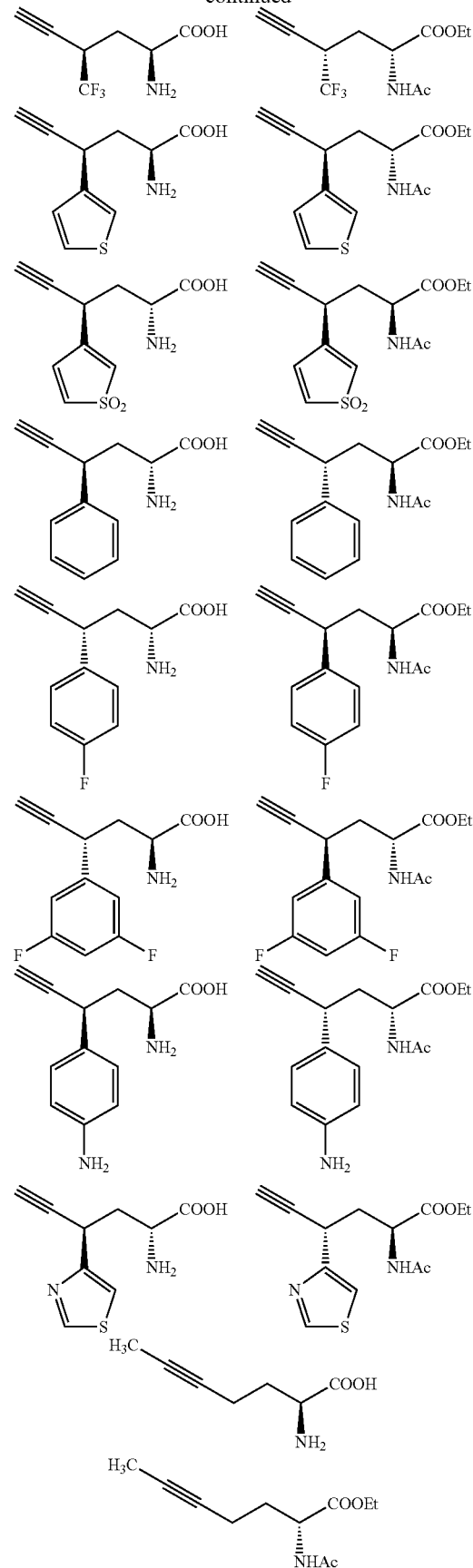

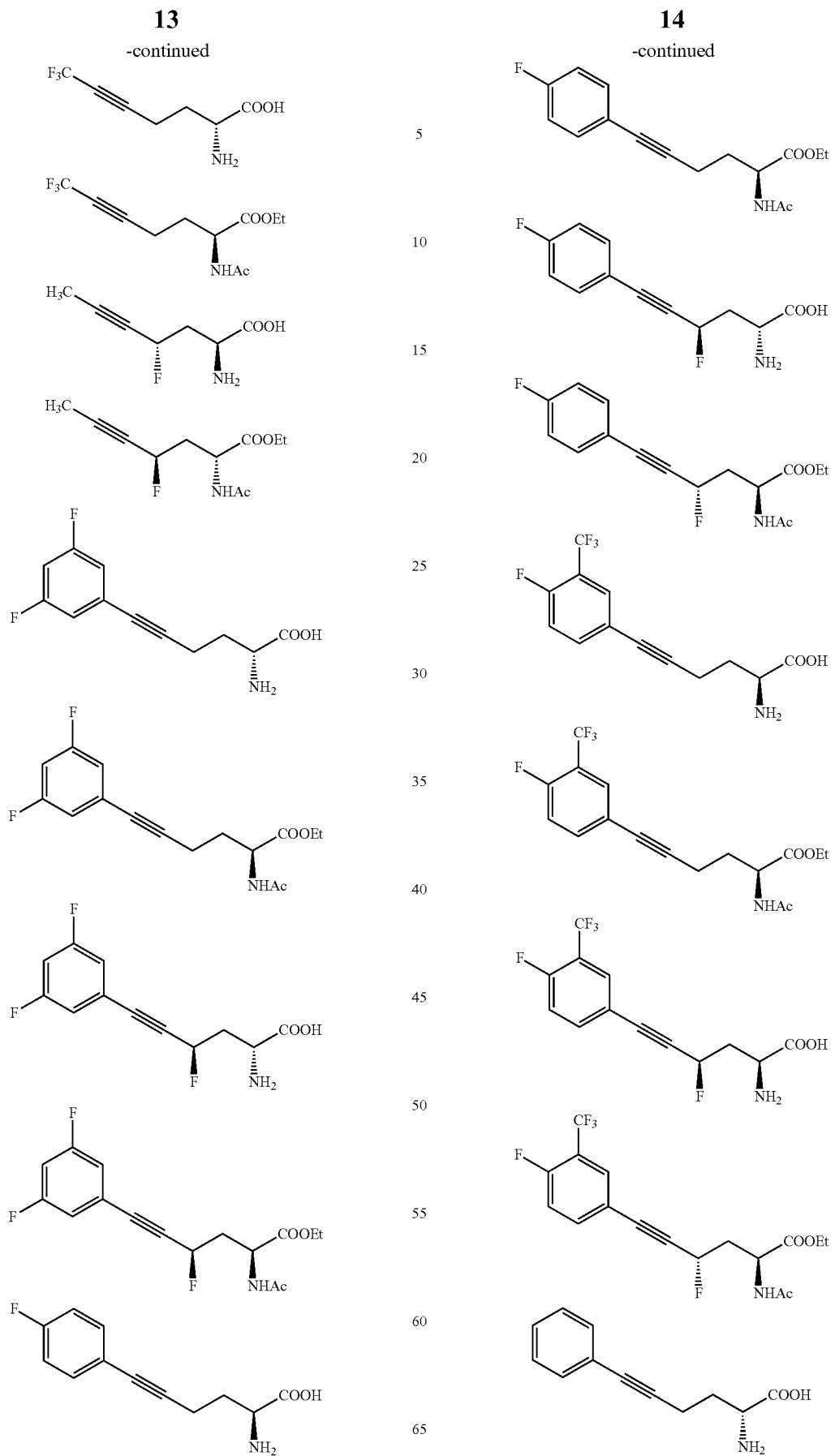

-continued

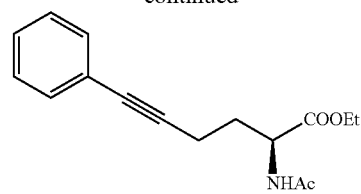

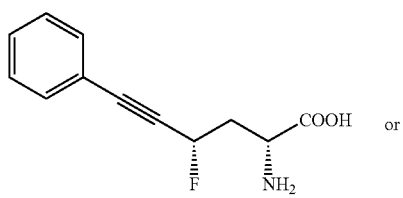

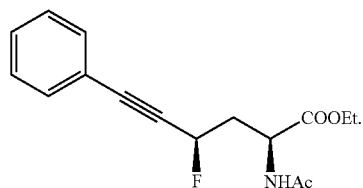

Certain embodiments are directed to compounds of formula (III):

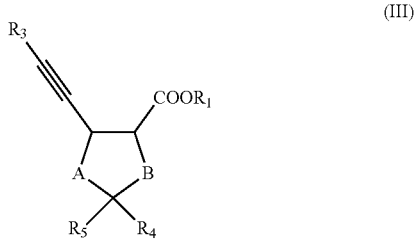

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_4$ and $R_5$ are each independently hydrogen, substituted or unsubstituted alkyl, substituted or unsubstituted aryl, or join to form a 3- to 6-membered substituted or unsubstituted cycloalkyl or heterocycle, and A and B are each independently O, NH, $SO_2$, or $CH_2$. In additional embodiments, one or more of these species may be excluded. In some embodiments, the compound is a salt, enantiomer, or diastereomer of a compound represented by formula (III).

In some embodiments, $R_1$ is hydrogen. In further embodiments, $R_3$ is hydrogen. In a particular embodiment, A is NH and B is $SO_2$. In some aspects, $R_4$ and $R_5$ are each methyl or phenyl. In some embodiments, $R_4$ and $R_5$ together form a cyclopentyl ring. In particular aspects, a compound of formula (III) is at least (or at most) one of the following:

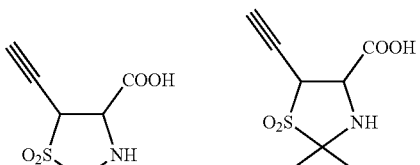

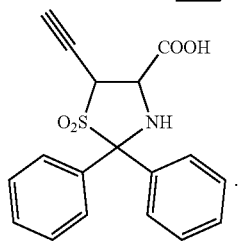

Certain embodiments are directed to compounds of formula (IV):

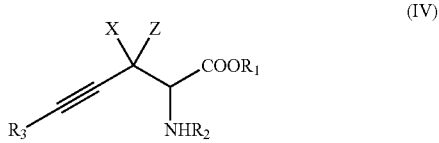

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, and X and Z are each independently hydrogen, a halide, CN, substituted or unsubstituted alkyl, substituted or unsubstituted aryl, substituted or unsubstituted heteroaryl, or a substituted or unsubstituted heterocycle. In additional embodiments, one or more of these species may be excluded. In some embodiments, the compound is a salt, enantiomer, or diastereomer of the compound represented by formula (IV).

In a specific embodiment, a compound of formula (IV) is:

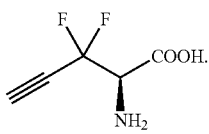

Certain embodiments are directed to compounds of formula (V):

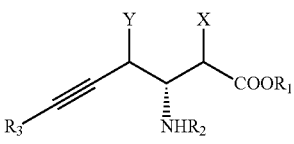

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, R₂ is hydrogen, acyl, substituted or unsubstituted alkyl, substituted or unsubstituted aryl, substituted or unsubstituted heteroaryl, or a substituted or unsubstituted heterocycle, X is hydrogen, a halide, nitrile, substituted or unsubstituted alkyl, substituted or unsubstituted aryl, substituted or unsubstituted heteroaryl, a substituted or unsubstituted heterocycle, and Y is hydrogen, a halide, nitrile, substituted or unsubstituted alkyl, substituted or unsubstituted aryl, substituted or unsubstituted heteroaryl, substituted or unsubstituted heterocycle, or an electron-donating group. In additional embodiments, one or more of these species may be excluded. In some embodiments, the compound is a salt, enantiomer, or diastereomer of the compound represented by formula (V).

In particular aspects, a compound of formula (V) is at least (or at most) one of the following:

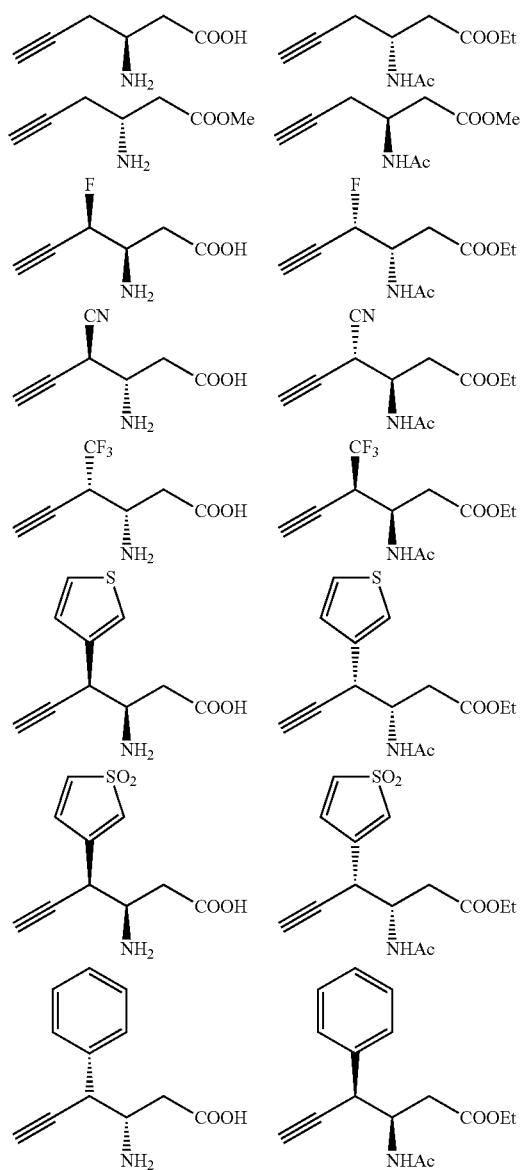

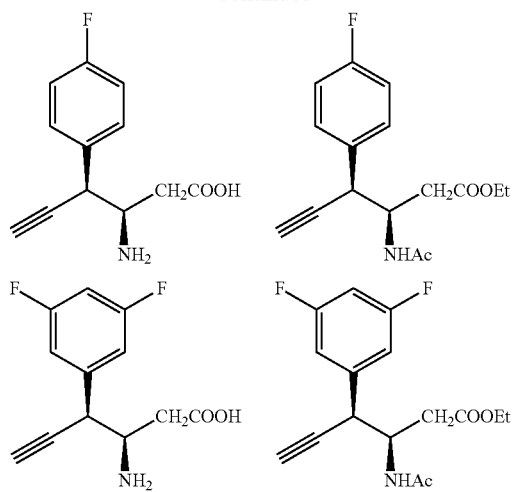

-continued

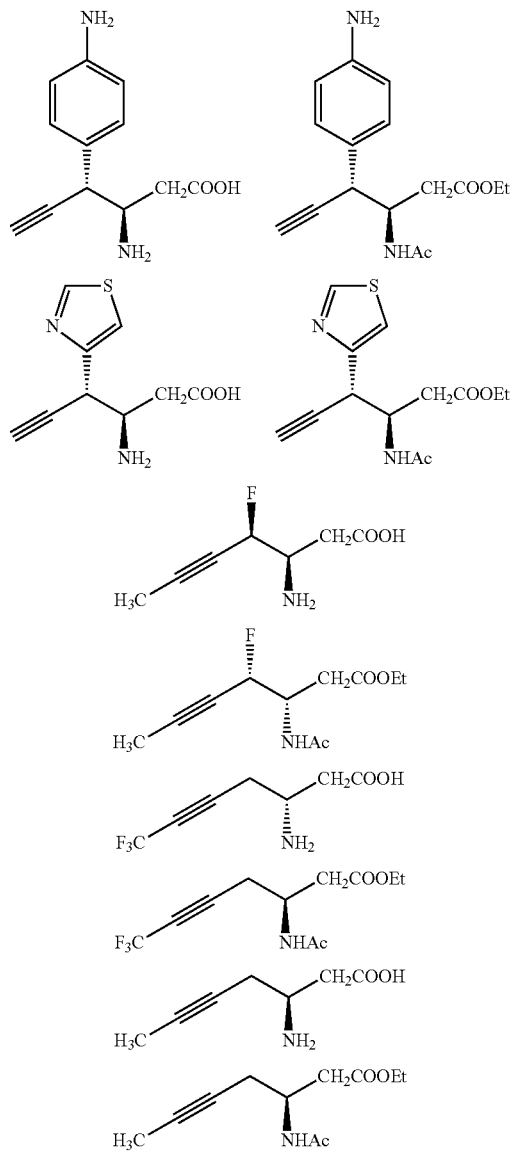

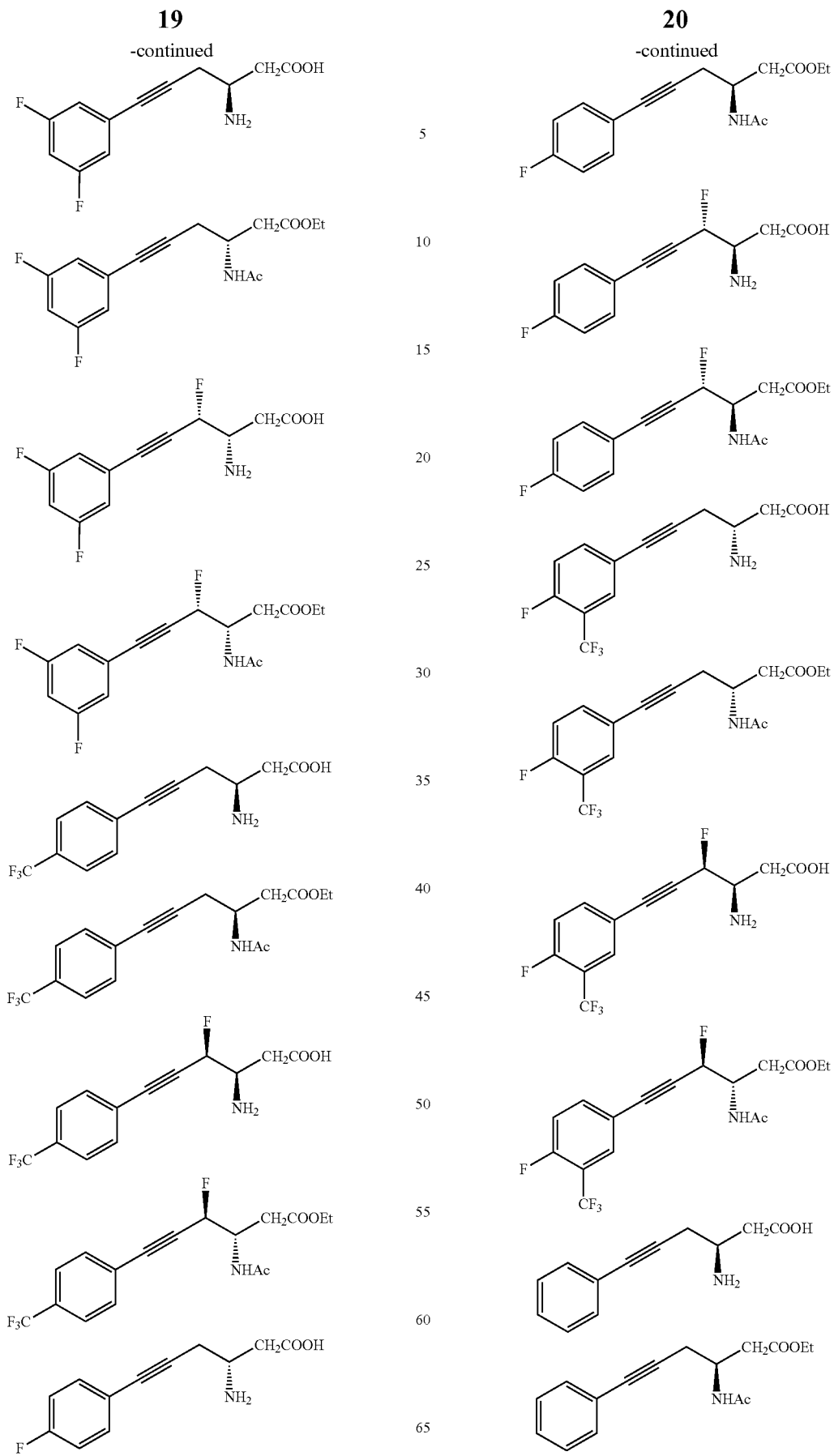

-continued

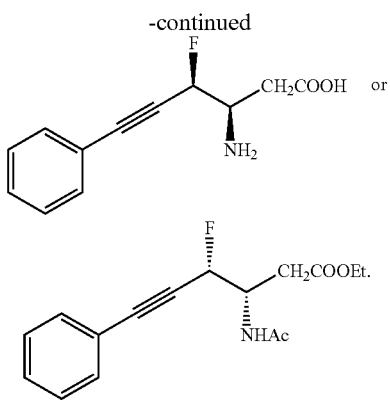

In some embodiments, a method of treating, preventing, or reducing a sleep-related breathing disorder in an individual in need thereof further comprises administering one or more additional therapeutic agents. A second therapeutic agent may be selected from carbonic anhydrase inhibitors, cholinesterase inhibitors, adenosine inhibitors, progestational agents, opioid antagonists, central nervous system stimulants, selective serotonin reuptake inhibitors (SSRis), antidepressants, antihypertensives, calcium channel antagonists, ACE inhibitors, respiratory stimulants, alpha-2 adrenergic agonists, gamma aminobutyric acid agonists, and glutamate antagonists. In yet further embodiments, an additional therapeutic agent may be at least one therapeutic agent selected from acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, and sabeluzole.

A second and/or additional, i.e., third, therapeutic agent can be administered in the same composition or in separate compositions. In some embodiments, the first inhibitor or treatment is administered, and a second inhibitor or treatment is administered. In some embodiments, the second therapeutic agent is administered within 3 days of the CSE antagonist. In some embodiments, the second therapeutic agent is administered within 24 hours of the CSE antagonist. In some embodiments, the second therapeutic agent is administered within 3 hours of the CSE antagonist. In further embodiments, an additional therapeutic agent may be used in conjunction with the CSE inhibitor, or with the combination of the CSE inhibitor and second therapeutic agent.

The compositions may be administered in any appropriate manner. In some embodiments, the composition is administered orally, intraadiposally, intraarterially, intraarticularly, intracranially, intradermally, intralesionally, intramuscularly, intranasally, intraocularally, intrapericardially, intraperitoneally, intrapleurally, intraprostaticaly, intrarectally, intrathecally, intratracheally, intratumorally, intraumbilically, intravaginally, intravenously, intravesicularlly, intravitreally, liposomally, locally, mucosally, orally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, via localized perfusion, bathing target cells directly, or any combination thereof.

Methods may involve administering a composition containing about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of a CSE antagonist, or any range derivable therein.

Alternatively, embodiments may involve providing or administering to the patient or to cells or tissue of the patient about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 nanograms (ng), micrograms (mcg), milligrams (mg), or grams of a CSE antagonist, or any range derivable therein, in one dose or collectively in multiple doses. In some embodiments, the composition comprises between about 0.1 ng and about 2.0 g of a CSE antagonist.

Alternatively, the composition may have a concentration of a CSE antagonist that is about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 mg or micrograms/ml or mg/ml, or any range derivable therein.

If a liquid, gel, or semi-solid composition, the volume of the composition that is administered to the patient may be about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 microliters (µl) or milliliters (ml), or any range derivable therein. In certain embodiments, the patient is administered up to about 10 ml of the composition.

The amount of CSE antagonist that is administered or taken by the patient may be based on the patient's weight (in kilograms). Therefore, in some embodiments, the patient is administered or takes a dose or multiple doses amounting to about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 micrograms/kilogram (kg) or mg/kg, or any range derivable therein.

The composition may be administered to (or taken by) the patient 1, 2, 3, 4, 5, 6, 7, 8, 9, 10, 11, 12, 13, 14, 15, 16, 17, 18, 19, 20 or more times, or any range derivable therein, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range derivable therein. It is specifically contemplated that the composition may be administered once daily, twice daily, three times daily, four times daily, five times daily, or six times daily (or any range derivable therein) and/or as needed to the patient. Alternatively, the composition may be administered every 2, 4, 6, 8, 12 or 24 hours (or any range derivable therein) to or by the patient. In some embodiments, the patient is administered the composition for a certain period of time or with a certain number of doses after experiencing symptoms of a sleep-related breathing disorder.

The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, the methods and systems of the present invention that "comprises," "has," "includes" or "contains" one or more elements possesses those one or more elements, but is not limited to possessing only those one or more elements. Likewise, an element of a method or system of the present invention that "comprises," "has," "includes" or "contains" one or more features possesses those one or more features, but is not limited to possessing only those one or more features.

Any method or system disclosed herein can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Throughout this application, the term "about" is used to indicate that a value includes the standard deviation of error for the device and/or method being employed to determine the value.

The term "substantially" is defined as being largely but not necessarily wholly what is specified (and include wholly what is specified) as understood by one of ordinary skill in the art. In any disclosed embodiment, the term "substantially" may be substituted with "within [a percentage] of" what is specified, where the percentage includes 0.1, 1, 5, and 10 percent.

As used herein, in the specification, "a" or "an" may mean one or more, unless clearly indicated otherwise. As used herein, in the claim(s), when used in conjunction with the word "comprising," the words "a" or "an" may mean one or more than one. As used herein "another" may mean at least a second or more.

Other objects, features and advantages disclosed herein will become apparent from the following detailed description. It should be understood, however, that the detailed description and the specific examples, while indicating preferred embodiments, are given by way of illustration only, since various changes and modifications within the spirit and scope of the invention will become apparent to those skilled in the art from this detailed description.

BRIEF DESCRIPTION OF THE DRAWINGS

FIGS. 1A-1F HO-2 null mice exhibit irregular breathing with apnea and hypoapnea. FIG. 1A depicts breathing monitored by plethysmography in un-sedated six month old, female wild-type (WT) mice and age and gender matched HO-2$^{-/-}$ mice (top). Plethysmography (bottom) includes arrows that indicate apnea (complete cessation of breathing for >2 breaths duration) and a shaded area that represents hypoapnea (≥30 reduction in tidal volume). FIG. 1C is a graph depicting the average of hypoapnea index (number of hypoapnea events per hour) in wild-type (WT) and HO-2$^{-/-}$ mice. FIG. 1D includes Poincaré plots of breath to breath ($BB_i$) versus next BB interval ($BB_{i+1}$) for 500 breaths in a single six month old, female, wild-type (left) mouse and an age and gender matched HO-2$^{-/-}$ mouse (right). FIG. 1E is a graph depicting standard deviation 1 of breath-to-breath intervals of HO-2 null mice as compared with wild-type mice. FIG. 1F is a graph depicting standard deviation 2 of breath-to-breath intervals in HO-2 null as compared with wild-type mice.

FIGS. 2A-2C HO-2 null mice exhibit both obstructive and central apnea. HO-2 null mice were chronically implanted electrodes in the inspiratory intercostal muscle. Inspiratory intercostal electromyographic activity (I-EMG), integrated I-EMG were recorded along with breathing by plethysmography were continuously monitored for six hours in unsedated HO-2 null mice. FIG. 2A is an example of breathing in an HO-2 null mouse showing apnea with increased I-EMG activity (obstructive apnea). FIG. 2B is an example of breathing in an HO-2 null mouse showing apnea with total absence of I-EMG activity (central apnea). FIG. 2C is a graph depicting average (mean±SEM) of obstructive and central apneas during six hours of recording in HO-2 null mice. * Denotes P<0.05.

FIG. 3A-3D Increased incidence of apnea during sleep in HO-2 null mice. Electrodes were implanted under surgical anesthesia for monitoring electroencephalographic (EEG) and electromyographic activity of neck muscles ($EMG_{neck}$) in wild-type and HO-2 null mice. After recovery from surgery, EEG, $EMG_{neck}$ were recorded along with breathing by plethysmography ($V_T$) in unsedated mice for six hours. Wake, non-rapid eye movement (NREM) and rapid eye movement (REM) sleep were identified as outlined in methods and results. FIG. 3A is an example of breathing ($V_T$), EEG, $EMG_{neck}$ under wake, NREM, and REM sleep in a wild-type mouse. FIG. 3B is an example of breathing ($V_T$), EEG, $EMG_{neck}$ under wake, NREM, and REM sleep in a HO-2-/- mouse. FIG. 3C is a graph depicting the average (mean±SEM) data of the number of apnea (events/hour) in wild-type and HO-2$^{-/-}$ mice under wake, NREM and REM sleep. FIG. 3D is a graph depicting the average (mean±SEM) data of the number of hypoapnea index (number of events with ≥30 reduction in tidal volume per hour) in wild-type and HO-2$^{-/-}$ mice under wake, NREM and REM sleep. * and ** Denote P<0.05 and <0.01, respectively.

FIGS. 4A-4H Carotid chemo reflex contributes to apnea in HO-2 null mice. FIG. 4A depicts examples of breathing responses of HO-2 null mice to normoxia (21% $O_2$), hyperoxia (90% $O_2$), and mild hypoxia (15% $O_2$). FIG. 4B is a graph depicting the average (mean±SEM) data of number of apnea per hour presented as percent of control normoxia (21% $O_2$) from HO-2 null mice exposed to 15 minutes of hyperoxia (90% $O_2$) and mild hypoxia (15% $O_2$). FIG. 4C depicts examples of breathing monitored by plethysmography in an unsedated wild-type (WT) mouse, and age and gender matched HO-2$^{-/-}$ and HO-2$^{-/-}$+Cse$^{-/-}$ mice. Arrows indicate apnea (complete cessation of breathing for >2 breaths duration). FIG. 4D includes three sets of Poincaré plots of breath to breath ($BB_i$) versus next BB interval ($BB_{i+1}$) for 500 breaths in a single WT mouse, and age and gender matched HO-2$^{-/-}$ and HO-2$^{-/-}$+Cse$^{-/-}$ mice. FIG. 4E is a graph depicting the analysis of the standard deviation 1 (SD1) of breath-to-breath (BB) intervals. FIG. 4F is a graph depicting the analysis of the standard deviation 2 (SD2) of breath-to-breath (BB) intervals. FIG. 4G is a graph depicting the average of the number of apnea (events/hr) in WT and HO-2$^{-/-}$ and HO-2$^{-/-}$+Cse$^{-/-}$ mice. FIG. 4H is a graph depicting the average of the hypoapnea index (number of events with ≥30 reduction in tidal volume per hour in WT and HO-2$^{-/-}$ and HO-2$^{-/-}$+Cse$^{-/-}$ mice. ** Denote P<0.01.

FIGS. 5A-5I L-propargylglycine (L-PAG), a CSE inhibitor normalizes breathing in HO-2 null mice. FIG. 5A includes examples of breathing monitored by plethysmography in an unsedated HO-2$^{-/-}$ mouse treated with intraperitoneal administration of vehicle (saline) or 30 and 90 mg/Kg of L-PAG. Arrows indicate apnea (complete cessation of breathing for >2 breaths duration). FIG. 5B is a graph depicting the average data (mean±SEM) of dose-response of L-PAG on number apnea per hour presented as percent of vehicle treated controls in HO-2 null mice. FIG. 5C includes Poincaré plots of breath to breath ($BB_i$) versus next BB interval ($BB_{i+1}$) for 500 breaths in a single HO-2$^{-/-}$ mouse treated with vehicle or L-PAG (30 mg/kg). FIG. 5D is a graph depicting average data (mean±SEM) of the analysis of the standard deviation 1 (SD1) of breath-to-breath (BB) intervals. FIG. 5E is a graph depicting average data (mean±SEM) of the analysis of the standard deviation 2 (SD2) of breath-to-breath (BB) intervals. FIG. 5F is a graph depicting average data (mean±SEM) of number of apneas per hour in HO-2 null mice treated with intra-peritoneal administration of either vehicle or L-PAG (30 mg/Kg) and after 24 hours post-L-PAG administration. FIG. 5G is a graph depicting average data (mean±SEM) of hypoapnea index in HO-2 null mice treated with intra-peritoneal administration of either vehicle or L-PAG (30 mg/Kg) and after 24 hours post-L-PAG administration. FIG. 5H is a graph depicting the average data (mean±SEM) of the effects of oral administration of either vehicle or 30 mg/kg of L-PAG on number of apneas per hour (H) in HO-2 null mice. FIG. 5I is a graph depicting the average data (mean±SEM) of the effects of oral administration of either vehicle or 30 mg/kg of L-PAG on hypoapnea index (number of events with 30% reduction in tidal volume per hour). * and ** Denote P<0.05 and 0.01, respectively.

FIG. 6A is a graph depicting the percentage of population of mice in wake, NREM, or REM sleep stages for WT and HO-2$^{-/-}$ mice. FIG. 6B is a graph depicting the difference in apnea index (events/hr) between mice of ages 5 months and >6 months.

FIGS. 7A-7D Echocardiography & quantitative data in wild-type and HO-2 null mice. FIG. 7A includes echocardiograms of WT and HO-2$^{-/-}$ mice. FIG. 7B is a graph depicting fractional shortening for WT and HO-2$^{-/-}$ mice. FIG. 7C is a graph depicting left ventricular inner diameter (LVID, mm) for WT and HO-2$^{-/-}$ mice. FIG. 7D is a graph depicting ventricular wall thickness for WT and HO-2$^{-/-}$ mice.

FIGS. 8A-8C Effect of breathing 2% $CO_2$ on apneas in HO-2 null mice. FIG. 8A is a plethysmography of an HO-2 null mouse during normoxic conditions followed by a 2% $CO_2$ challenge. FIG. 8B is a graph depicting the change in number of apnea events/hr upon challenging HO-2 null mice with 2% $CO_2$. FIG. 8C is a graph depicting a 25% reduction in the number of apneas, which was primarily due to reduced central apnea.

FIGS. 9A-9B Carotid body response to hypoxia. FIG. 9A includes measurements of carotid body response to hypoxia in wild-type, HO-2 null and HO-2-CSE double knock out mice. HO-2 null mice showed an augmented carotid body response to hypoxia as compared with wild-type mice, and this effect was absent in HO-2-CSE double knockout mice. FIG. 9B is a graph depicting sensory response (Δimp/s) for wild-type, HO-2 null and HO-2-CSE double knock out mice in response to hypoxia.

FIGS. 10A-10B Effect of CSE inhibitor on $H_2S$ production. FIG. 10A depicts a dose-response of L-propargylglycine (L-PAG) on $H_2S$ production in an in vitro assay using mouse liver homogenates. FIG. 10B depicts the effect of L-PAG (30 μM) on $H_2S$ generation by CSE and CBS in mouse liver homogenates. Data are presented as mean±SEM from 4 independent experiments. **P<0.01; n.s., not significant.

DETAILED DESCRIPTION

Figure 11:
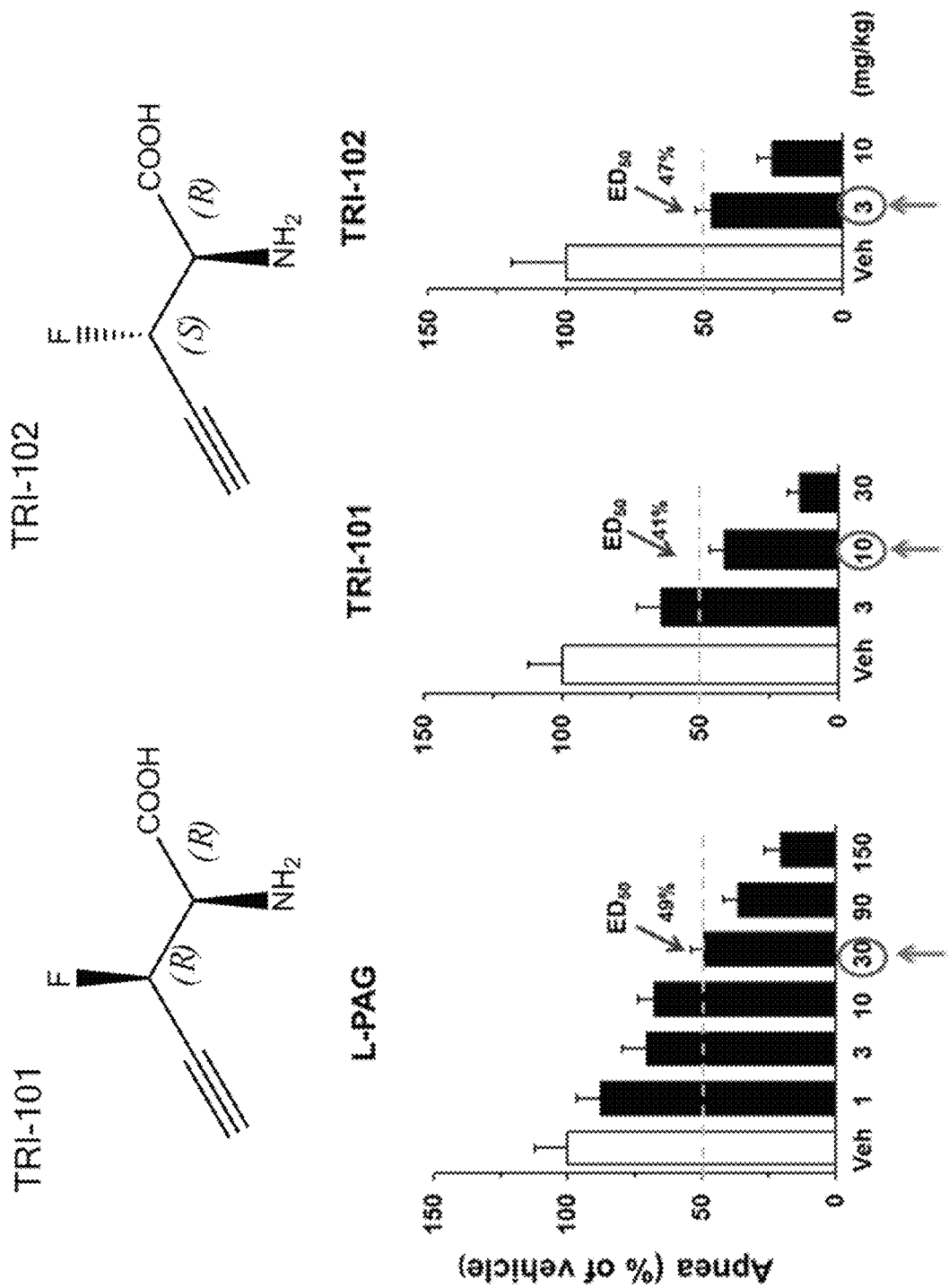
FIG. 11 includes comparative dose-response graphs for systemic administration of L-PAG and two CSE inhibitors TRI-101 and TRI-102. The $ED_{50}$ for L-PAG is ~30 mg/kg, while the $ED_{50}$ for TRI-101 is ~10 mg/kg (3-fold more potent than L-PAG) and the $ED_{50}$ for TRI-102 is ~3 mg/kg (10-fold more potent than L-PAG).

Sleep apnea is a highly prevalent respiratory disorder often associated with either OSA or CSA or a combination of both. Patients with sleep apnea exhibit a wide spectrum of co-morbidties including hypertension. Currently available therapies have limited efficacy in normalizing breathing in patients with OSA or CSA.

A recent study showed exaggerated carotid body response to hypoxia in mice lacking hemeoxygenase-2 (HO-2), an enzyme responsible for the generation of endogenous carbon monoxide (CO) and this effect is mediated by augmented cystathionine-γ-lyase (CSE)-derived hydrogen sulfide ($H_2S$) signaling in the carotid body. The results disclosed herein include experiments with HO-2 null mice as an experimental model of sleep apnea exhibiting both OSA and CSA phenotype. HO-2 null mice exhibit both OSA and CSA with higher incidence of apnea during sleep. The results disclosed herein demonstrate that correction of the carotid body chemoreflex by inhibiting CSE-derived $H_2S$ generation reversibly prevents apnea in HO-2 null mice. The tested compounds demonstrated that the onset of anti-apneic effect was rapid and was seen as quickly as two hours after the administration. Moreover, the effects of ED 50 dose were fully reversed after 24 hours. Furthermore, there was an absence of any mortality or gross toxicity within the dose range tested. The CSE inhibitors disclosed herein may be used as therapeutic agents for the treatment of sleep-related breathing disorders including but not limited to OSA and CSA.

A. THERAPEUTIC COMPOUNDS

A CSE antagonist is a compound that acts to inhibit, attenuate, or decrease the activity of the CSE protein. In certain embodiments, a CSE inhibitor is a compound of formula (I):

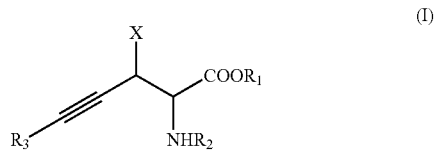

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, and X is hydrogen, a halide, CN, substituted or unsubstituted alkyl, substituted or unsubstituted aryl, substituted or unsubstituted heteroaryl, or a substituted or unsubstituted heterocycle. In some embodiments, the compound is a salt, enantiomer, or diastereomer of the compound represented by formula (I).

In some aspects, the stereochemistry at the α-carbon may be (R) or (S). In further aspects, the stereochemistry at the β-carbon may be (R) or (S). The stereochemistries of the α- and β-carbons may be the same, or may be different. In a particular aspect, $R_1$, $R_2$, and $R_3$ are each hydrogen.

In particular aspects, a compound of formula (I) is at least one of the following:

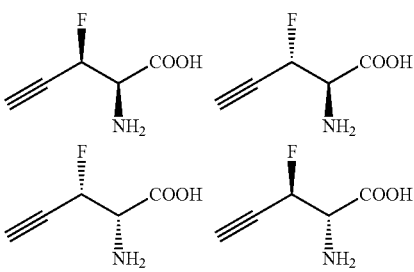

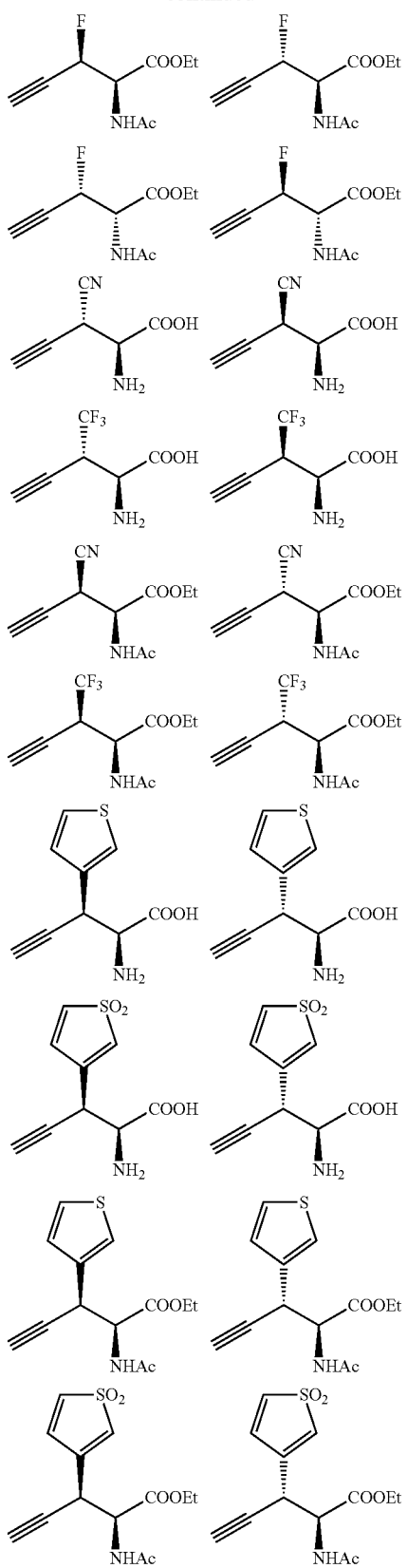
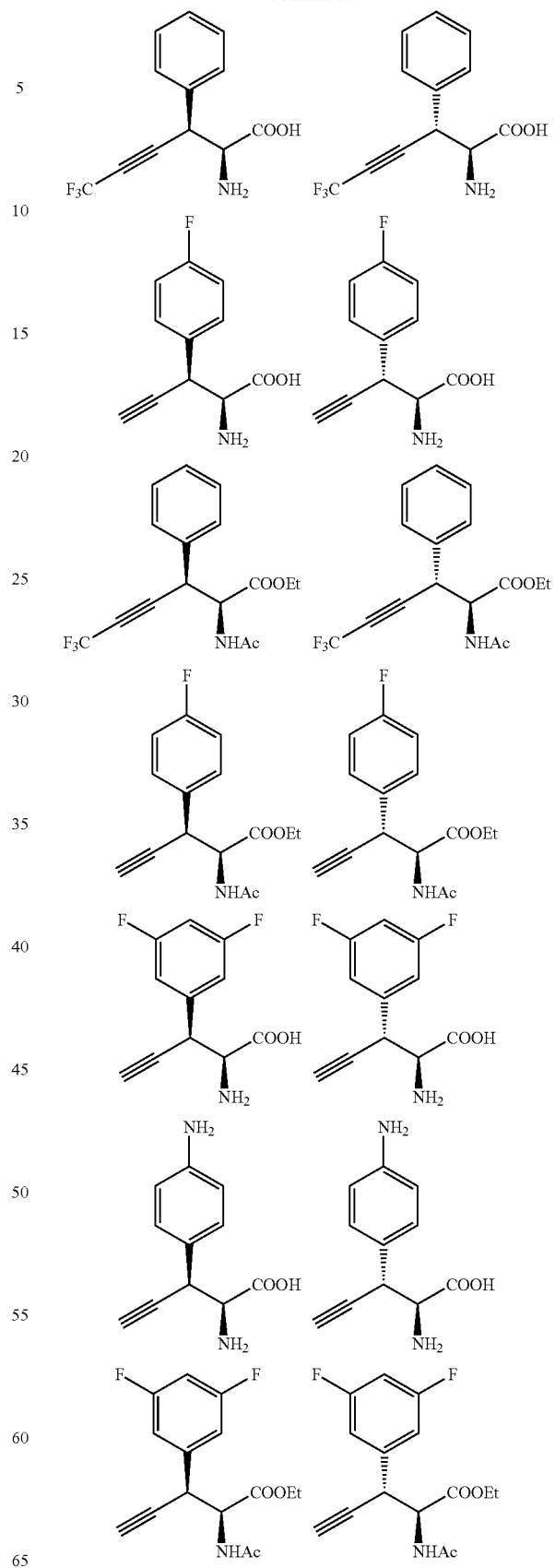

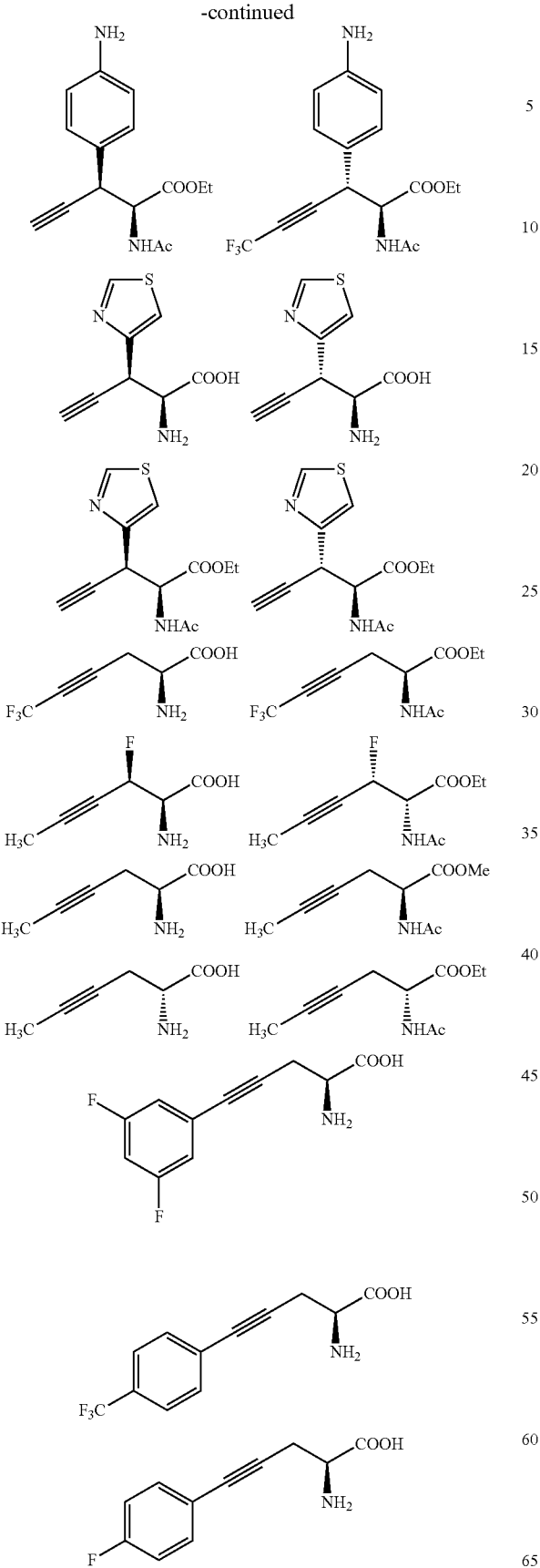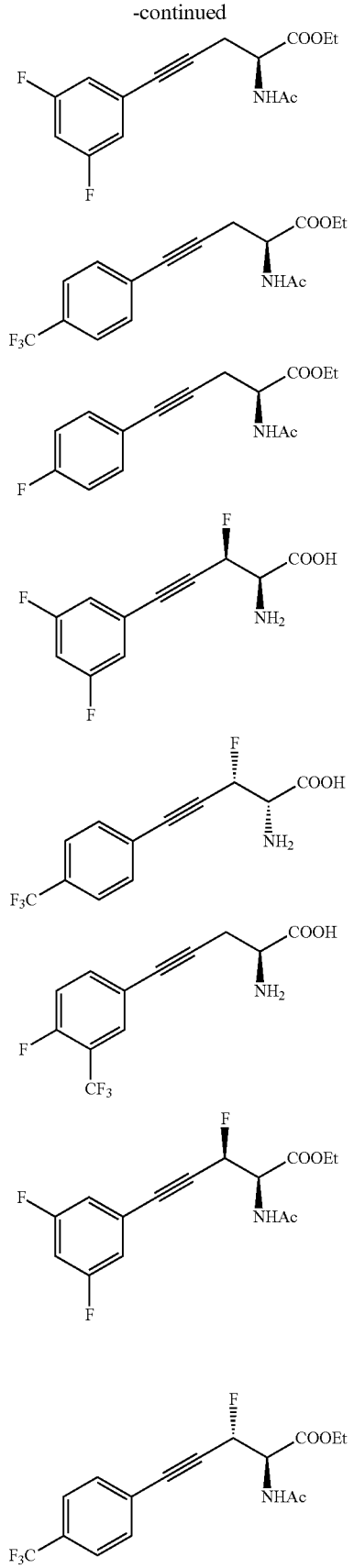

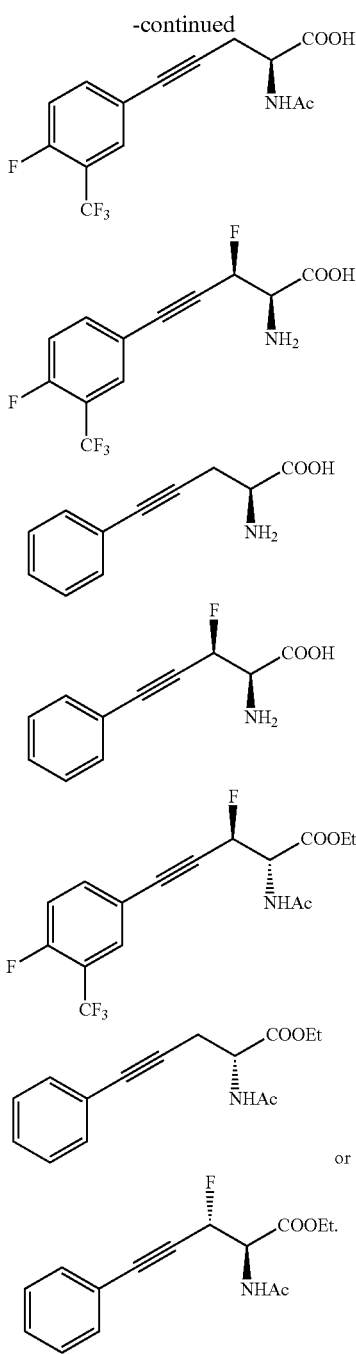

In some embodiments, a CSE inhibitor is a compound of formula (II):

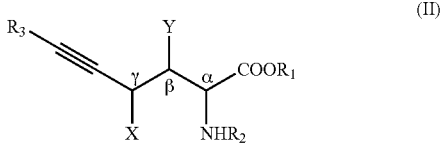

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, X is hydrogen, a halide, CN, substituted or unsubstituted alkyl, substituted or unsubstituted aryl, substituted or unsubstituted heteroaryl, a substituted or unsubstituted heterocycle, and Y is hydrogen, substituted or unsubstituted alkyl, substituted or unsubstituted aryl, substituted or unsubstituted heteroaryl, substituted or unsubstituted heterocycle, or an electron-donating group. In some embodiments, the compound is a salt, enantiomer, or diastereomer of the compound represented by formula (II).

The stereochemistry of each of the α-, β-, and γ-carbons may each independently be (R) or (S). In some embodiments, the stereochemistries of two of the α- and β- and γ-carbons are different from the stereochemistry of the third chiral carbon. Examples (α, β, γ) include (S, R, S), (R, S, R), (S, S, R), (R, R, S), (S, R, R), and (R, S, S). In other embodiments, the stereochemistries of the α- and β- and γ-carbons are the same, e.g., (R, R, R) and (S, S, S). In particular aspects, a compound of formula (II) is at least one of the following:

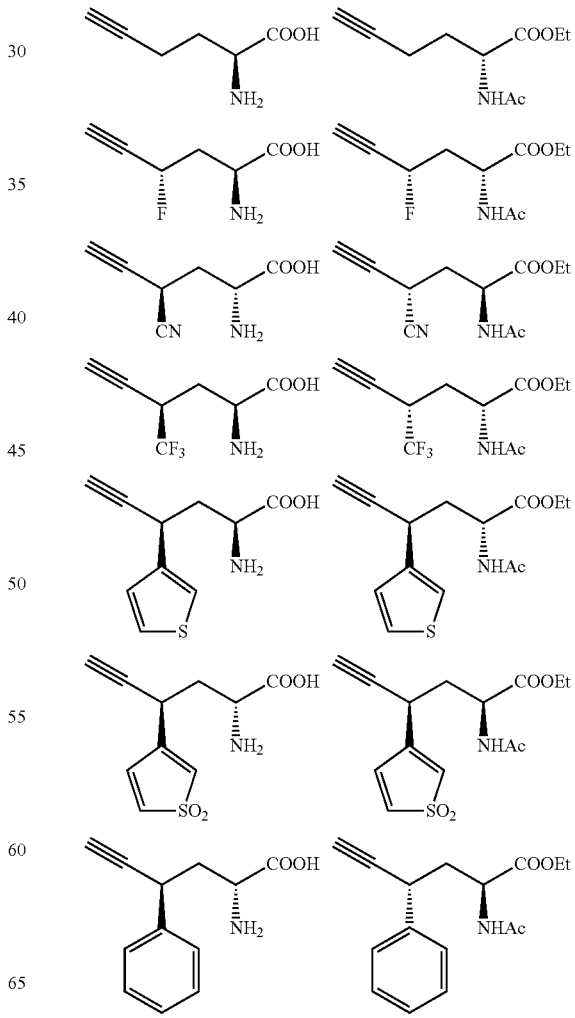

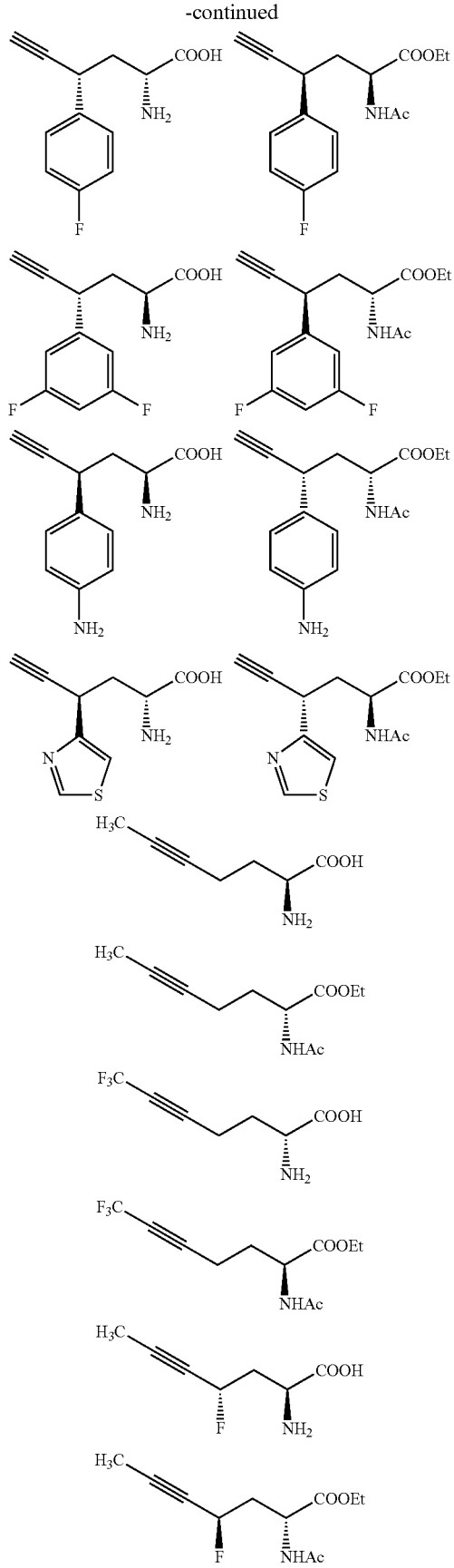
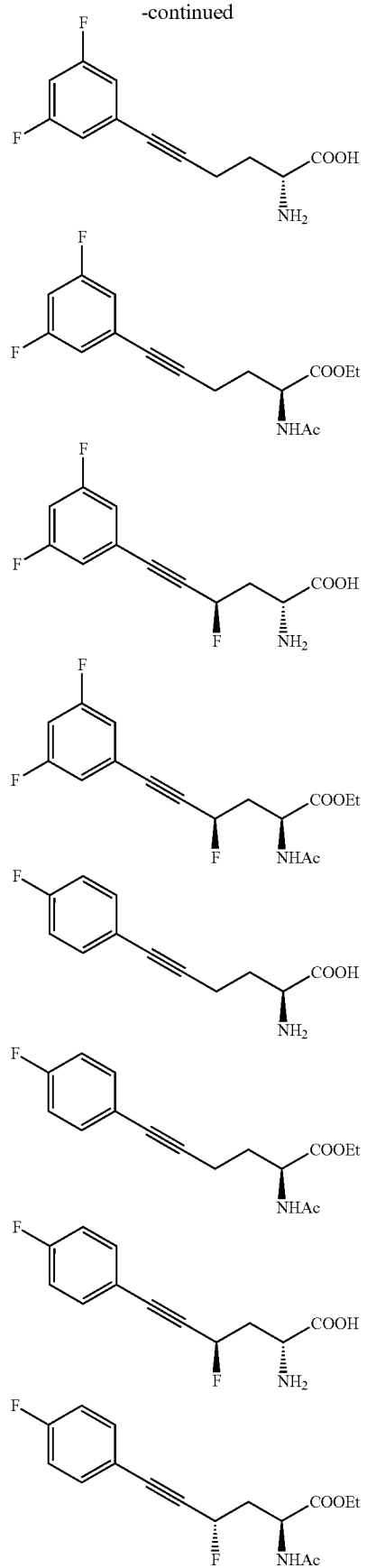

-continued

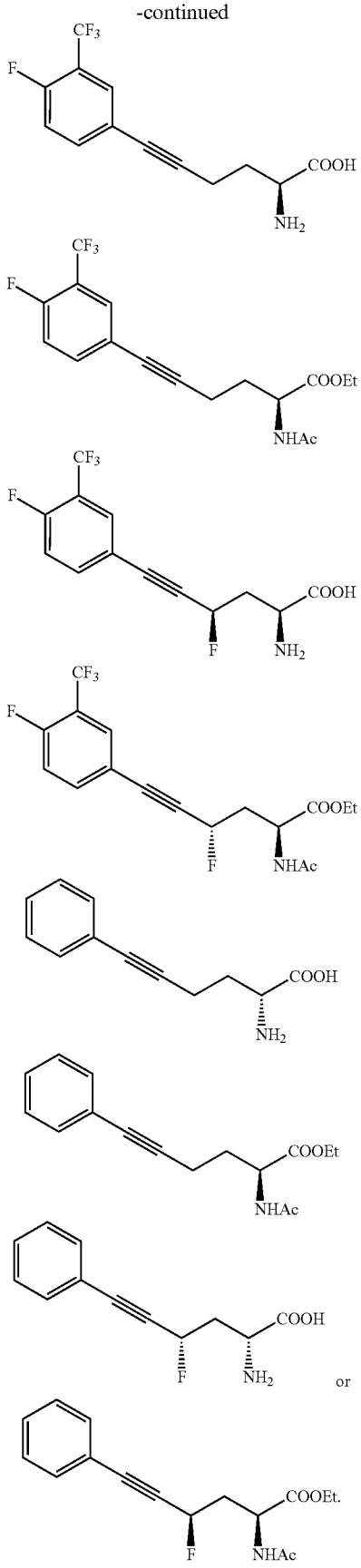

In some embodiments, a CSE inhibitor is a compound of formula (III):

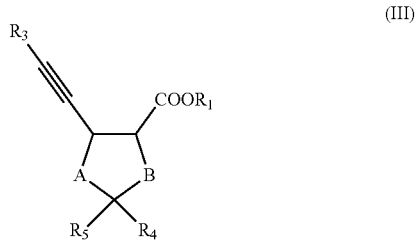

wherein $R_1$ and $R_3$ are each independently hydrogen, substituted or unsubstituted alkyl, substituted or unsubstituted aryl, substituted or unsubstituted heteroaryl, or a substituted or unsubstituted heterocycle, $R_4$ and $R_5$ are each independently hydrogen, substituted or unsubstituted alkyl, substituted or unsubstituted aryl, or join to form a 3- to 6-membered substituted or unsubstituted cycloalkyl or heterocycle, and A and B are each independently O, NH, $SO_2$, or $CH_2$. In some embodiments, the compound is a salt, enantiomer, or diastereomer of a compound represented by formula (III).

In some embodiments, $R_1$ is hydrogen. In further embodiments, $R_3$ is hydrogen. In a particular embodiment, A is NH and B is $SO_2$. In some aspects, $R_4$ and $R_5$ are each methyl or phenyl. In some embodiments, $R_4$ and $R_5$ together form a cyclopentyl ring.

In particular aspects, a compound of formula (III) is at least one of the following:

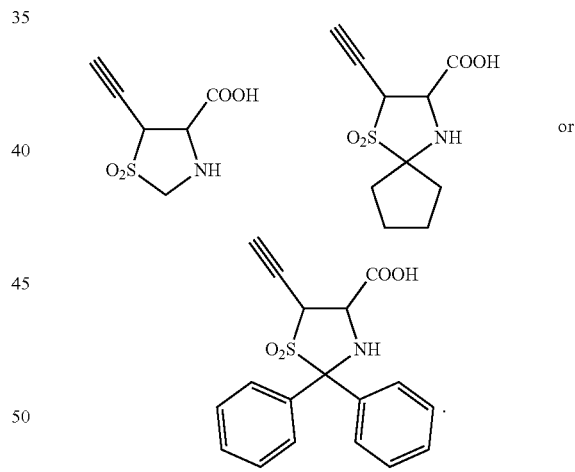

In certain embodiments, a CSE inhibitor is a compound of formula (IV):

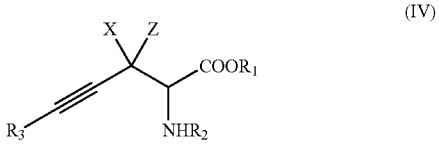

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, and X and Z are each independently hydrogen, a halide, CN, substituted or unsubstituted alkyl, substituted or unsubstituted aryl, substituted or unsubstituted heteroaryl, or a substituted or unsubstituted heterocycle. In some embodiments, the compound is a salt, enantiomer, or diastereomer of the compound represented by formula (IV). In a specific embodiment, the compound of formula (IV) is:

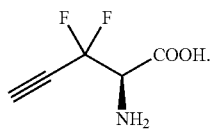

In certain embodiments, a CSE inhibitor is a compound of formula (V):

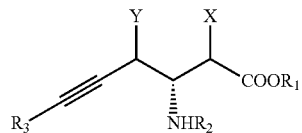

wherein $R_1$ and $R_3$ are independently hydrogen, substituted or unsubstituted alkyl, substituted or unsubstituted aryl, substituted or unsubstituted heteroaryl, or a substituted or unsubstituted heterocycle, $R_2$ is hydrogen, acyl, substituted or unsubstituted alkyl, substituted or unsubstituted aryl, substituted or unsubstituted heteroaryl, or a substituted or unsubstituted heterocycle, X is hydrogen, a halide, nitrile, substituted or unsubstituted alkyl, substituted or unsubstituted aryl, substituted or unsubstituted heteroaryl, a substituted or unsubstituted heterocycle, and Y is hydrogen, halide, nitrile, substituted or unsubstituted alkyl, substituted or unsubstituted aryl, substituted or unsubstituted heteroaryl, substituted or unsubstituted heterocycle, or an electron-donating group. In some embodiments, the compound is a salt, enantiomer, or diastereomer of the compound represented by formula (V). In particular aspects, a CSE inhibitor is at least (or at most) one of the following:

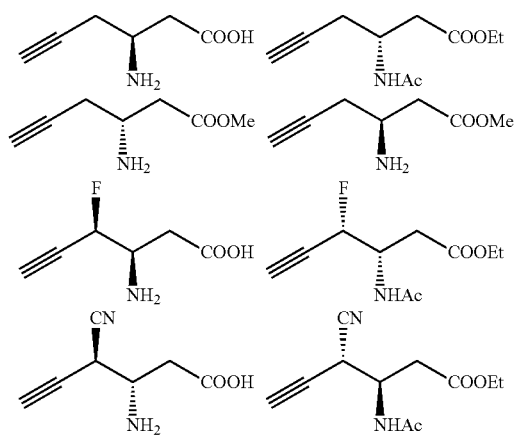

-continued

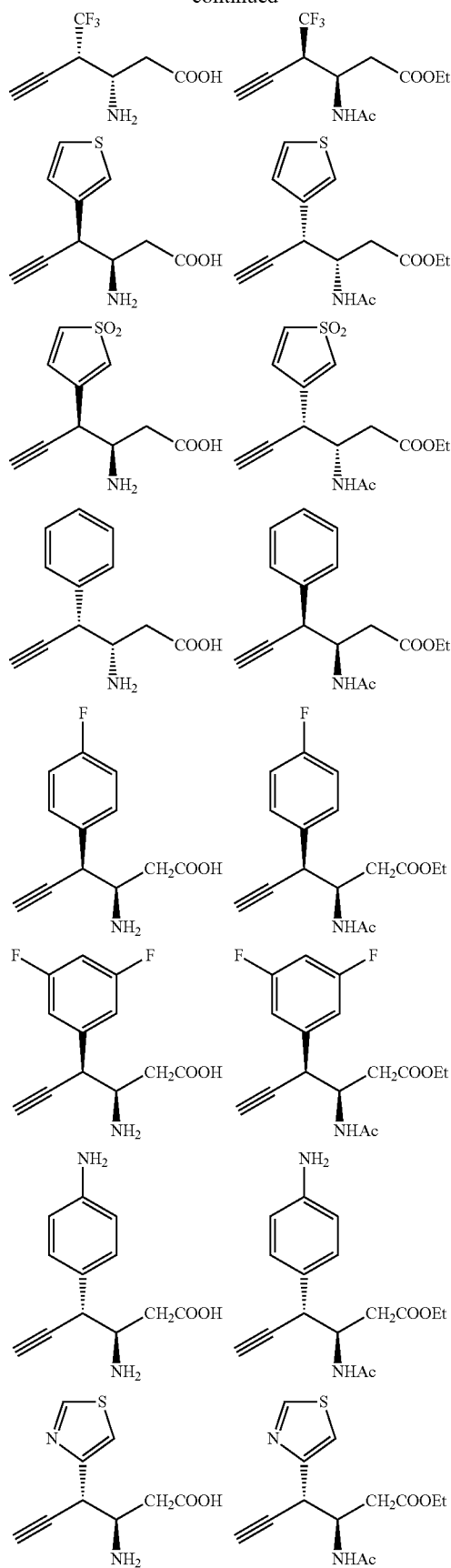

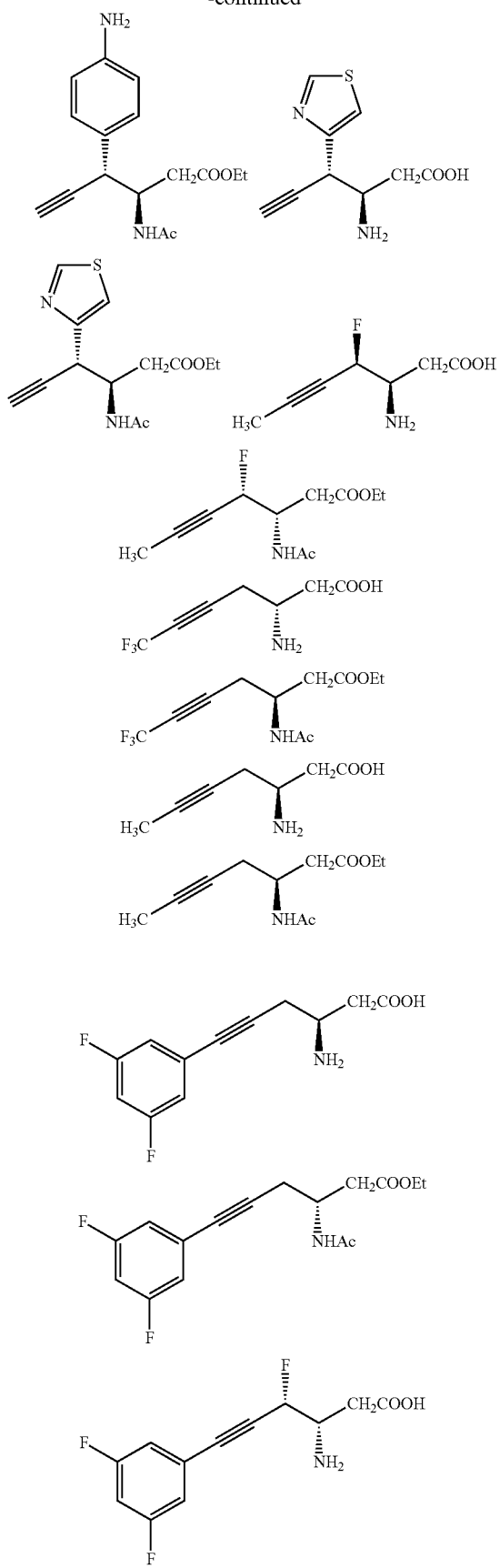

-continued

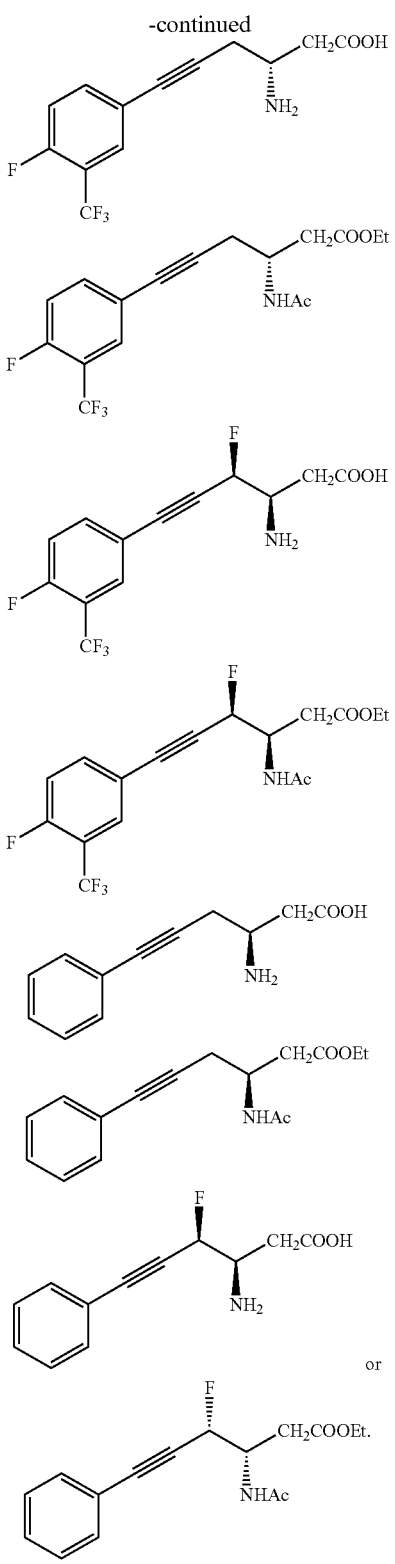

or

B. DEFINITIONS

When used in the context of a chemical group, "hydrogen" means —H; "hydroxy" means —OH; "oxo" means =O; "halo" means independently —F, —Cl, —Br or —I; "amino" means —NH2; "hydroxyamino" means —NHOH; "nitro" means —NO2; imino means =NH; "cyano" means —CN; "isocyanate" means —N=C=O; "azido" means —N3; in a monovalent context "phosphate" means —OP(O)(OH)2 or a deprotonated form thereof; in a divalent context "phosphate" means —OP(O)(OH)O— or a deprotonated form thereof; "mercapto" means —SH; "thio" means=S; "sulfonyl" means —S(O)2-; and "sulfinyl" means —S(O)—.

In the context of chemical formulas, the symbol "—" means a single bond, "=" means a double bond; and "≡" means triple bond. The symbol " ---- " represents an optional bond, which if present is either single or double. The symbol " ==== " represents a single bond or a double bond. Thus, for example, the structure

includes the structures

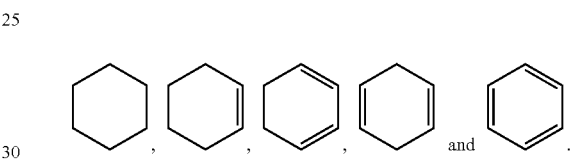

As will be understood by a person of skill in the art, no one such ring atom forms part of more than one double bond. The symbol " ⌇ ", when drawn perpendicularly across a bond indicates a point of attachment of the group. It is noted that the point of attachment is typically only identified in this manner for larger groups in order to assist the reader in rapidly and unambiguously identifying a point of attachment. The symbol " ◢ " means a single bond where the group attached to the thick end of the wedge is "out of the page." The symbol " ▙ " means a single bond where the group attached to the thick end of the wedge is "into the page". The symbol " ⌇ " means a single bond where the conformation (e.g., either R or S) or the geometry is undefined (e.g., either E or Z).

Any undefined valency on an atom of a structure shown in this application implicitly represents a hydrogen atom bonded to the atom. When a group "R" is depicted as a "floating group" on a ring system, for example, in the formula:

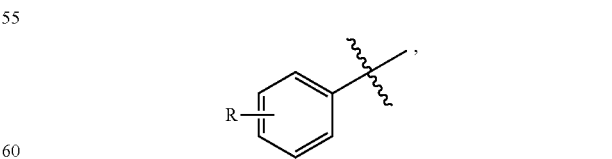

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

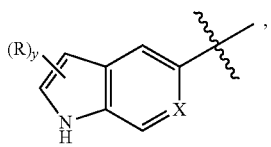

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C\leq 8)}$" or the class "alkene$_{(C\leq 8)}$" is two. For example, "alkoxy$_{(C\leq 10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OCH$_2$CH$_2$OH, —C(O)CH$_3$, —NC(O)CH$_3$, —N(CH$_3$)$_2$, —C(O)NH$_2$, —OC(O)CH$_3$, —S(O)$_2$NH$_2$, or imidazolidinone. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting examples of a haloalkyl. An "alkane" refers to the compound H—R, wherein R is alkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups. An "alkane" refers to the compound H—R, wherein R is alkyl.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen.

Non-limiting examples of alkenyl groups include: —CH=CH₂ (vinyl), —CH=CHCH₃, —CH=CHCH₂CH₃, —CH₂CH=CH₂ (allyl), —CH₂CH=CHCH₃, and —CH=CH—C₆H₅. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —CH=CHF, —CH=CHCl and —CH=CHBr, are non-limiting examples of substituted alkenyl groups. An "alkene" refers to the compound H—R, wherein R is alkenyl.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. When alkynyl is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "alkyne" refers to the compound H—R, wherein R is alkynyl.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

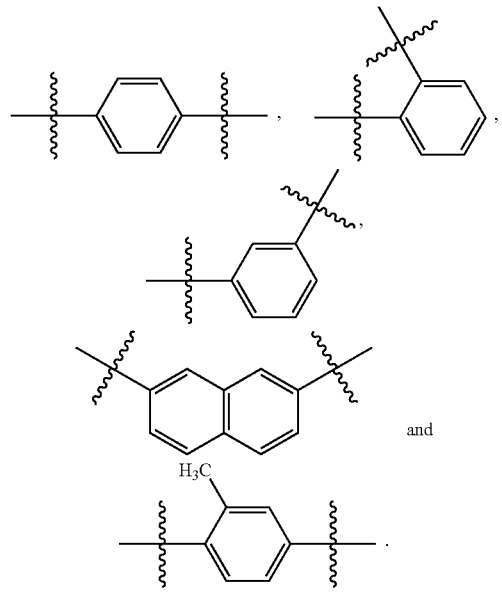

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "arene" refers to the compound H—R, wherein R is aryl.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

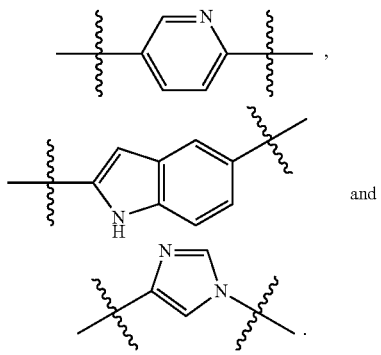

When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH₃ (methoxy), —OCH₂CH₃ (ethoxy), —OCH₂CH₂CH₃, —OCH(CH₃)₂ (isopropoxy), —OCH(CH₂)₂, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The term "alcohol" corresponds to an alkane, as defined above, wherein at least one of the hydrogen atoms has been replaced with a hydroxy group.

The term "alkylamino" when used without the "substituted" modifier refers to the group —NHR, in which R is an alkyl, as that term is defined above. Non-limiting examples of alkylamino groups include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂, —N(CH₃)(CH₂CH₃), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O) NH$_2$, —OC(O)CH$_3$, or —S(O)$_2$NH$_2$. The groups —NHC (O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "alkenylsulfonyl", "alkynylsulfonyl", "arylsulfonyl", "aralkylsulfonyl", and "heteroarylsulfonyl", are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

As used herein, a "chiral auxiliary" refers to a removable chiral group that is capable of influencing the stereoselectivity of a reaction. Persons of skill in the art are familiar with such compounds, and many are commercially available.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

The compositions may be administered one or more times. In some embodiments, the compositions are administered 1, 2, 3, 4, 5, 6, 7, 8, 9, or 10 times or more.

"Effective amount" or "therapeutically effective amount" or "pharmaceutically effective amount" means that amount which, when administered to a subject or patient for treating a disease, is sufficient to effect such treatment for the disease. In some embodiments, the subject is administered at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 20, 30, 40, 50, 60, 70, 80, 90, or 100 mg/kg (or any range derivable therein).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2] oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts: Properties, and Use (P. H. Stahl & C. G. Wermuth eds., *Verlag Helvetica Chimica Acta,* 2002).

A "disease" is defined as a pathological condition of a body part, an organ, or a system resulting from any cause, such as infection, genetic defect, or environmental stress. A "health-related condition" is defined herein to refer to a condition of a body part, an organ, or a system that may not be pathological, but for which treatment is sought. Examples include sleep-related breathing disorders. The disease can be any disease, and non-limiting examples include obstructive sleep apnea and central sleep apnea.

As used herein, the phrases "treating and/or preventing" or "treatment and/or prevention" includes the administration of the compositions, compounds or agents of the invention to prevent or delay the onset of the symptoms, complications, or biochemical indicia of a disease, alleviating or ameliorating the symptoms or arresting or inhibiting further development of the disease, condition, or disorder (e.g., obstructive sleep apnea). "Treating and/or preventing" further refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the phrase "treating and/or preventing" includes the administration of the therapeutic agents of the disclosure to prevent, to alleviate, or to reduce occurrence of sleep apnea and associated pathologies. In some embodiments, the patient may have sleep apnea that is not caused by being obese or because of excessive weight or the patient is not overweight or obese according to their body mass index. (People are generally considered obese when their body mass index (BMI), a measurement obtained by dividing a person's weight by the square of the person's height, is over 30 kg/m2, with the range 25-30 kg/m2 defined as overweight.)

A "therapeutically effective amount" of a substance/molecule may vary according to factors such as the disease state, age, sex, and weight of the individual, and the ability of the substance/molecule to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

An "individual" or "subject" is a mammal. Mammals include, but are not limited to, domesticated animals cows, sheep, cats, dogs, and horses), primates (e.g., humans and non-human primates such as monkeys), rabbits, and rodents (e.g., mice and rats). In certain embodiments, the individual or subject is a human.

By "reduce or inhibit" is meant the ability to cause an overall decrease of 20%, 30%, 40%, 50%, 60%. 70%, 75%, 80%, 85%, 90%, 95%, or greater. Reduce or inhibit can refer to the symptoms of the disorder being treated, the presence or size of metastases, or the size of the primary tumor.

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, genti sates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound. In some aspects, a prodrug may include at least one of an ester and amide functional group.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed 2n, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diasteromers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

C. PHARMACEUTICAL FORMULATIONS AND ROUTES OF ADMINISTRATION

For administration to a mammal in need of such treatment, the compounds in a therapeutically effective amount are ordinarily combined with one or more excipients appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and tableted or encapsulated for convenient administration. Alternatively, the compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

The pharmaceutical compositions useful in the present invention may be subjected to conventional pharmaceutical operations such as sterilization and/or may contain conventional pharmaceutical carriers and excipients such as preservatives, stabilizers, wetting agents, emulsifiers, buffers, etc.

The compounds of the present disclosure may be administered by a variety of methods, including but not limited to orally, sublingually, and by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound or compounds by other than parenteral administration, it may be necessary to coat the compound with, or co-administer the compound with, a material to prevent its inactivation. For example, a therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound or compounds may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

D. COMBINATION THERAPY

The compositions and related methods of the present invention, particularly administration of a CSE antagonist, may also be used in combination with the administration of a second therapeutic agent. In some embodiments, a CSE antagonist and second therapeutic agent are used in combination with an additional therapeutic agent.

Administration of the additional therapeutic agent(s) may precede or follow the CSE antagonist treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Effective combination therapy may be achieved with a single composition or pharmacological formulation that includes two or more therapeutic agents, or with two or more distinct compositions or formulations, administered at the same time, wherein one composition includes a CSE antagonist, and the other(s) includes an additional therapeutic agent or agents. Alternatively, the therapy may precede or follow the other agent treatment by intervals ranging from minutes to months.

Non-limiting examples of such combination therapy include combination of one or more compounds of the invention with a second therapeutic agent may be selected from carbonic anhydrase inhibitors, cholinesterase inhibitors, adenosine inhibitors, progestational agents, opioid antagonists, central nervous system stimulants, selective serotonin reuptake inhibitors (SSRis), antidepressants, antihypertensives, calcium channel antagonists, ACE inhibitors, respiratory stimulants, alpha-2 adrenergic agonists, gamma aminobutyric acid agonists, and glutamate antagonists. In yet further embodiments, an additional therapeutic agent may be at least one therapeutic agent selected from acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, and sabeluzole.

E. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Material And Methods

1. Preparation of Animals

Experiments were approved by the Institutional Animal Care and Use Committee of the University of Chicago and were performed on age-matched C57/BL6 wild type and HO-2$^{-/-}$ mice. At the end of the experiment, mice were euthanized by intra-cardiac injection (0.1 mL) of euthanasia solution (Beuthanasia-D Special, Schering-Plough).

2. Measurement of Breathing

Breathing was continuously monitored under room air from 10:00 AM to 4:00 PM by whole-body plethysmography (emka Technologies, Falls Church, VA) while ambient temperatures were maintained at 25±1° C. Breathing signals were collected and stored with a data acquisition system (emka Technologies, Falls Church, VA; or PowerLab 8/35, AD Instruments, Australia), and scored off-line with commercial software (RemLogic™, Natus). Apneas were scored when there was a complete pause of respiration for the duration of 3 or more breaths. Hypopneas were scored when there was a 30% reduction in tidal volume or signal amplitude, often with an abrupt return to hyperventilation breaths at the end of the event.

3. Echocardiographic Assessment of Left Ventricular Dimension and Function

Transthoracic echocardiography was performed in mice anesthetized with 1.5% isoflurane using an ultrasound imaging system (VisualSonics 770) equipped with a 35 MHz transducer. Left ventricular ejection fraction, end-systolic dimension (ESD), end-diastolic dimension (EDD), and wall thickness were assessed at different time points accordingly. Three cycles were measured for each assessment, and the average values were obtained. Fractional shortening (FS) were calculated from the equation: FS=(EDD−ESD)/EDD× 100.

4. Implantation of Electroencephalography (EEG) and Electromyography (EMG)

Electrodes for EEG and nuchal EMG were implanted in mice placed on a stereotaxic frame under anesthesia with ketamine/xylazine mixture (90/9 mg/kg; I.P.) or 2% isoflurane. Four stainless steel screws served as epidural electrodes were placed on both the left and right frontal and parietal cortex according to the stereotaxic coordinates: frontal, mediolateral 1.7 mm, anteroposterior 1.5 mm relative to bregma; parietal, mediolateral 1.7 mm, anteroposterior 1.0 mm relative to lambda. Each screw was attached with a stainless steel wire that was subsequently attached to an EEG/EMG headmount (Model 8431, Pinnacle Technology, Lawrence, KS). To monitor neck muscle activity, two stainless steel wires that were attached with the EEG/EMG headmount were inserted into the neck muscles. The head mount was secured on the skull with dental cement.

For experiments involving recording of intercostal EMG, two stainless steel wires were implanted into intercostal muscles. Wires were tunneled under the skin and attached to the headmount that was secured on the skull.

All incisions were sutured and buprenorphine was administrated every 12 hours post-surgery (0.05 mg/kg, S.C.) as an analgesic until no evidence of pain was observed. Mice were allowed 5 days to recover before EEG/EMG recoding.

5. Measurement of Breathing Pattern Along with EEG/EMG

On the day of experiment, the animal was placed in the plethysmograph chamber, and the recording cable was attached to the headmount through a header. EEG/EMG signals were pre-amplified and filtered (Model 8202, Pinnacle Technology Inc., Lawrence, KS). Along with breathing, the conditioned EEG/EMG signals were then collected with a data acquisition system (PowerLab 8/35, AD Instruments, Australia). EEG/EMG data were scored off-line with commercial software (RemLogic™) in a 10-second epoch. Non Rapid Eye Movement(NREM) sleep was scored when increased amplitude, low frequency (delta/theta range) electrocortical activity was combined with a low-level EMG. REM sleep was scored when the EEG showed theta activity and the nuchal EMG was low. Wake was manifested by high EMG tone, movement artifacts, and alpha rhythms.

6. Ex Vivo Carotid Body Recording

Sensory nerve activity was recorded from ex vivo carotid bodies harvested from anesthetized mice. Briefly, the carotid sinus nerve was treated with collagenase, and several nerve bundles were isolated. Action potentials from one of the nerve bundles were recorded using a suction electrode (~20-μm-diameter tip). In general, 2-3 action potentials of varying size and amplitude were seen in a given nerve bundle. Action potentials of similar height, duration, and shape ("single" unit) were selected using Spike histogram software (LabChart 7 Pro) for analysis of the sensory nerve activity. To obtain a stable baseline sensory nerve activity, carotid bodies were first superfused for 1 hour with normoxia-equilibrated medium. Subsequently, baseline sensory nerve activity under normoxia was recorded for 5 min. Sensory nerve responses to hypoxia were monitored for 3 min. The $PO_2$ in the medium was determined by a blood gas analyzer (ABL 5). Hypoxic response was measured as the difference between the sensory nerve activity under baseline and during hypoxia (Δimp/s).

7. Data Analysis and Statistics

All data are reported as mean±SEM unless otherwise stated in the figure legends. Statistical analysis was performed with either one-way or two-way analysis of variance (ANOVA) with repeated measures followed by post-hoc Tukey's test. Chi-square test was employed for analysis of distribution of apnea. For the analysis of normalized data, Mann-Whitney's test was applied. All p values<0.05 were considered significant.

Example I

HO-2 Null Mice Exhibit Irregular Breathing with Apnea and Hypoapnea

Breathing was monitored by plethysmography in unsedated adult (>6 months old) male and female wild-type and HO-2$^{-/-}$ mice. Wild-type mice showed relatively stable breathing, whereas HO-2 null mice exhibited irregular breathing with apnea (cessation of breathing for >2 breaths duration), and hypoapnea (≥30% reduction in tidal volume; FIG. 1A). The irregular breathing was quantified by analyzing breath-to-breath (BB) interval (BBn) versus the subsequent interval (BBn+1) for 500 breaths in a wild-type and adult HO-2 null mouse during room air breathing and presented as Poincaré plots (FIG. 1B). Analysis of the standard deviation (SD) of BB intervals showed that SD1 (representing the y axis) and SD2 (representing the x axis) were significantly greater in HO-2 null than wild-type mice (FIGS. 1C-D).

Analysis of the number of apneas showed that a majority of HO-2 null mice (40 out of 70 mice; 57%) showed greater than 20 apneas per hour (excluding post-sigh apneas; FIG. 1E). The incidence of apneas ranged between 20-120 apnea/ hour (mean±SEM). By contrast, few wild type mice (2 of the 40 mice; 5%) showed the severe apnea phenotype (FIG. 1E). Unlike adults, younger HO-2 null mice (age 6-8 weeks) showed less number of apneas (FIG. 6B), suggesting the incidence of apnea increases with age.

The hypoapnea index (number of hypoapnea events per hour) was higher in HO-2 null as compared with wild-type mice (FIG. 1F). Analysis of arterial blood gases showed reduced arterial blood $PO_2$, $O_2$ saturation and elevated $PCO_2$ in HO-2 null mice as compared with wild-type mice (Table 1). Systolic, diastolic and mean blood pressures were elevated in HO-2 null mice as compared with age matched wild-type mice (FIG. 8). These results demonstrate that adult HO-2 null mice exhibit irregular breathing with high incidence of apnea and hypoapnea as compared with wild-type mice.

TABLE 1

| Arterial blood gas values under normoxia in WT and HO-2 KO mice | | |
|---|---|---|
| | WT (n = 8) | HO-2 KO (n = 11) |
| PaO$_2$(mmHg) | 99 ± 7 | 89 ± 6 |
| PaCO$_2$(mmHg) | 37 ± 2.9 | 40 ± 3.5 |
| pH | 7.29 ± 0.03 | 7.24 ± 0.04 |
| SaO$_2$(%) | 95 ± 1.7 | 86 ± 5.3 |

Example 2

HO-2 Null Mice Exhibit Mixed Obstructive and Central Apnea

Obstructive apnea is characterized by cessation of airflow with concomitant increase in respiratory motor activity;

whereas both breathing movements and respiratory motor activity are absent in central apnea. In order to determine whether apneas are of obstructive, or central or of mixed phenotype, inspiratory intercostal muscle electromygraphic activity (I-EMG) was recorded as an index of respiratory motor activity along with breathing monitored by plethysmography in unsedated HO-2 null mice. In a given mouse, during six hours of recording, there are incidences of apnea that were associated with increased I-EMG activity indicative of obstructive apnea (FIG. 2A), whereas others were accompanied with complete absence of I-EMG activity, suggestive of central apnea (FIG. 2B). Average data showed that a greater proportion of apnea are of obstructive than of central phenotype (FIG. 2C). These findings show that HO-2 null mice exhibit mixed phenotype of both obstructive and central apnea, and the incidence of the former was greater than the later type.

Example 3

Apnea in HO-2 Null Mice Occur During Sleep

To determine whether the occurrence of apnea depends on wake-sleep state, electroencephalogram (EEG), electromyogram (EMG) of neck muscles and breathing were simultaneously recorded in unsedated wild-type and HO-2-null mice. The following criterion was used for identifying wake state, Rapid eye movement (REM) and non REM (NREM) sleep. Wake state was characterized by EEG activity of mixed frequency with low amplitude and muscle tone as evidenced by EMG activity. Rapid eye movement (REM) sleep was identified by frequency of theta waves (6-9 Hz) and muscle atonia, and non REM (NREM) was characterized by high amplitude slow waves in the delta frequency range (1-4 Hz) and low muscle tone (FIGS. 3C-3D and FIG. 6).

During the wake state, the number of apneas and hypoapnea index were comparable between wild-type and HO-2 null mice (FIGS. 3C-3D). The number of apneas and hypoapnea index were unaltered during NREM and REM sleep in wild-type mice (FIG. 3A and FIGS. 3C-3D). By contrast, occurrence of apnea and hypoapnea index were markedly increased in NREM and REM in HO-2 null mice, with greater incidence of apnea in REM than in NREM sleep (FIG. 3 C-D). These results demonstrate that HO-2 null mice exhibit sleep apnea.

Example 4

Carotid Body Chemoreflex Contributes to Apnea in HO-2 Null Mice

The potential mechanisms that contribute to the genesis of apnea in HO-2 null mice were investigated. Cardiomyopathy can lead to irregular breathing with apnea. To determine whether the apnea in HO-2 null mice is due to cardiomyopathy, cardiac function was determined by echocardiography (FIG. 7A). Fractional shortening, left ventricular diameter, and ventricular wall thickness were all comparable between HO-2 null and wild-type mice (FIGS. 7B-7D). These findings suggest that normal cardiac function is preserved in HO-2 null mice and the increased incidence of apnea is unlikely due to cardiomyopathy.

An exaggerated carotid body chemoreflex has been implicated in causing irregular breathing with apnea. Because HO-2 null mice exhibit augmented carotid body response to hypoxia, the contribution of heightened carotid chemoreflex to apnea was determined. Bilateral ablation of the carotid bodies resulted in mortality in four HO-2 null mice tested.

The effects of hyperoxia (90% O2 for 15 min), which is known to inhibit the carotid body activity on breathing in HO-2 null mice were examined. Hyperoxia decreased the incidence of apnea by 80% as compared with room air breathing (FIGS. 4A-4B). The reduced incidence of apnea by hyperoxia was due to reduction in both obstructive and central apnea. Challenging HO-2 null mice with mild hypoxia (15% $O_2$), which stimulates the carotid body activity, markedly increased the number of apnea, with a 3 and 2 fold increase in obstructive and central apnea events, respectively (FIGS. 4A-4B). Although apnea can occur due to reduced sensitivity of central chemoreceptors to $CO_2$, challenging HO-2 null mice with 2% $CO_2$ resulted in only 25% reduction in the number of apneas, which was primarily due to reduced central apnea (FIG. 8). Together, these observations suggest that the carotid body chemoreflex is a major contributor to the increased incidence of apnea in HO-2 null mice.

Example 5

Blockade of CSE-Derived H2S Generation Normalizes Breathing in HO-2 Null Mice

The enhanced carotid body activity in HO-2 null mice is mediated by CSE-derived $H_2S$. Blockade of $H_2S$ signaling with genetic knock down of CSE should therefore normalize carotid body function and restore stable breathing in HO-2 null mice. This possibility was examined in HO-2-CSE double knockout mice. The carotid body response to hypoxia in wild-type, HO-2 null and HO-2-CSE double knock out mice was recorded. HO-2 null mice showed an augmented carotid body response to hypoxia as compared with wild-type mice, and this effect was absent in HO-2-CSE double knockout mice (FIG. 9). Unlike HO-2 null mice, HO-2-CSE double knockout mice exhibited stable breathing like the wild-type mice (FIGS. 4C-4G). These findings establish that CSE-derived $H_2S$ generation contributes to irregular breathing with apnea in HO-2 null mice through activation of carotid body chemo reflex.

The effect of pharmacological CSE blockade on restoration of stable breathing in HO-2 null mice was examined. L-propargylglycine (L-PAG) is an inhibitor of CSE. An in vitro assay showed that L-PAG inhibited CSE-derived $H_2S$ (FIG. 10A). The inhibitory effects of L-PAG were selective to CSE because $H_2S$ synthesis by cystathionine-β-synthase was unaffected (FIG. 10 B).

HO-2 null mice were treated with increasing doses of L-PAG via the intraperitoneal route, and breathing was monitored continuously for 6 hours. L-PAG reduced the number of apneas and restored stable breathing in a dose-dependent manner with an $ED_{50}$ value of 30 mg/kg (FIGS. 5A-5E). The anti-apneic effects of L-PAG were further analyzed at 30 mg/kg. The effects of L-PAG were seen after ~2 hours after the administration, and apnea returned to pre-injection values after 24 hours (FIG. 5F). L-PAG markedly reduced the occurrence of both obstructive and central apnea (FIG. 5G). Hypoapnea index was also reduced by L-PAG and this effect persisted even after 24 hours (FIG. 5H). Oral administration of L-PAG (30 mg/kg) was equally effective in reducing the number of apneas and the hypoapnea index (FIG. 5I). The anti-apneic effects of L-PAG (30 mg/kg) were associated with markedly reduced carotid body sensitivity to hypoxia in HO-2 null mice (FIG. 9B). There was no mortality with any of the doses of L-PAG tested.

Example 6

Pharmacokinetic Analysis of L-PAG

The finding that L-PAG was equally effective in normalizing breathing by the intraperitoneal and oral routes prompted the assessment of its pharmacokinetic (PK) properties. L-PAG showed 100% bioavailability given by either intraperitoneal or oral route. Plasma clearance profiles for oral and i.p. administration of L-PAG across the entire pharmacologically active range (10 mg/kg to 150 mg/kg) were essentially identical. Comparisons of L-PAG plasma levels with (a) dose-response parameters for L-PAG pharmacologic activity and (b) the kinetics of reversal of this pharmacologic activity, support the conclusion that a threshold plasma drug level of approximately 12 to 15 µg/ml is necessary to sustain anti-apnea action. This threshold plasma drug level is consistent with both (a) the minimal anti-apnea activity of the 10 mg/kg dose of L-PAG and (b) the kinetics of the reversal of anti-apnea activity with time seen at L-PAG doses of 30 mg/kg or higher.

Example 7

Design and Synthesize Novel L-PAG Analogs Using a Mechanism-Based Approach

Synthesis of new molecular entities (NME) based on "hits" identified by HTS failed to generate agents that were more active than L-PAG. For this reason, a mechanism-based approach was implemented to design L-PAG analogs based on the molecular mechanism of its inhibition of CSE. NME design was based on binding of the L-PAG amine to an internal CSE/pyridoxal phosphate (PLP) aldimine conjugate to form an external L-PAG/PLP aldimine conjugate. Deprotonation of L-PAG α- and β-protons gives way to an L-PAG/PLP allene intermediate. Binding of CSE to the L-PAG/PLP allene intermediate results in inhibition of CSE activity. Using this approach, a series of agents were designed and synthesized. Two agents (designated TRI-101 and TRI-102) were identified to be 3-fold and 10-fold more potent than L-PAG in inhibiting SDB in the HO2-KO mice (FIG. 11). Comparative dose-response data for systemic administration of L-PAG and the two current lead compounds are presented in FIG. 11. The $ED_{50}$ for L-PAG is ~30 mg/kg, while the $ED_{50}$ for TRI-101 is ~10 mg/kg (3-fold more potent than L-PAG) and the $ED_{50}$ for TRI-102 is ~3 mg/kg (10-fold more potent than L-PAG).

REFERENCES

1. Cowie, M. R. (2015). *New England Journal of Medicine*, 1095-1105.
McEvoy, D. (2016). *New England Journal of Medicine*.
Peppard, P. e. (2013). *American Journal of Epidemiology*, 1006-1014.

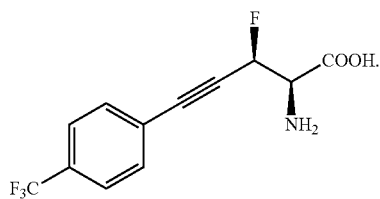
25. The method of claim 22, wherein the individual is administered an effective amount of
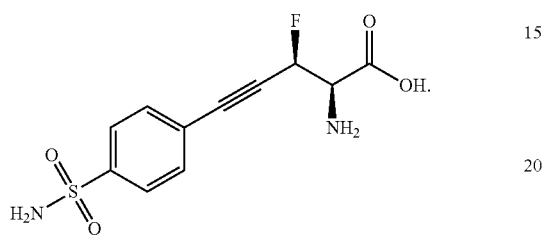

The invention claimed is:

1. A method of treating or reducing a sleep-related breathing disorder in an individual in need thereof comprising administering to the individual a therapeutically effective amount of a cystathionine-γ-lyase (CSE) antagonist, wherein the CSE antagonist is a propargylglycine analog compound of the formula

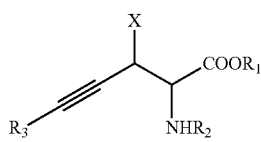

wherein:

$R_1$ and $R_3$ are independently hydrogen, substituted or unsubstituted alkyl, substituted or unsubstituted aryl, substituted or unsubstituted heteroaryl, or substituted or unsubstituted heterocycle;

$R_2$ is hydrogen, acyl, substituted or unsubstituted alkyl, substituted or unsubstituted aryl, substituted or unsubstituted heteroaryl, or substituted or unsubstituted heterocycle; and X is hydrogen, halide, CN, substituted or unsubstituted alkyl, substituted or unsubstituted aryl, substituted or unsubstituted heteroaryl, or substituted or unsubstituted heterocycle;

or a pharmaceutically acceptable salt, enantiomer, diastereomer, or prodrug thereof, wherein R1, R2, R3, and X are not all hydrogen, and wherein the individual is suffering from or having symptoms of a sleep-related breathing disorder selected from central sleep apnea (CSA), Cheyne-Stokes breathing-central sleep apnea (CSB-CSA), obesity hypoventilation syndrome (OHS), congenital central hypoventilation syndrome (CCHS), obstructive sleep apnea (OSA), idiopathic central sleep apnea (ICSA), narcotic-induced CSA, high altitude periodic breathing, chronic mountain sickness, impaired respiratory motor control associated with stroke, upper airway resistance syndrome (UARS), or impaired respiratory motor control associated with a neurologic disorder.

2. The method of claim 1, wherein the CSE antagonist reduces CSE-catalyzed synthesis of hydrogen sulfide ($H_2S$).

3. The method of claim 2, wherein reduced synthesis of $H_2S$ results in attenuation of carotid body activity.

4. The method of claim 1, wherein the CSE antagonist reduces chemosensitivity of the carotid body.

5. The method of claim 4, wherein reduced carotid body chemosensitivity is reduction of arterial blood oxygen sensitivity.

6. The method of claim 4, wherein reduced carotid body chemosensitivity is reduction of arterial blood carbon dioxide sensitivity.

7. The method of claim 4, wherein the reduced carotid body chemosensitivity reduces loop gain of the ventilator drive control system, blunts hypoventilation, lowers blood pressure, and/or dampens carotid sinus nerve activity.

8. The method of claim 1, wherein the CSE antagonist bolsters the carotid body's response to hypoxia.

9. The method of claim 1, further comprising administering a second therapeutic selected from carbonic anhydrase inhibitors, cholinesterase inhibitors, adenosine inhibitors, progestational agents, opioid antagonists, central nervous system stimulants, selective serotonin reuptake inhibitors (SSRis), antidepressants, antihypertensives, calcium channel antagonists, ACE inhibitors, respiratory stimulants, alpha-2 adrenergic agonists, gamma aminobutyric acid agonists, and glutamate antagonists.

10. The method of claim 1, further comprising administering an additional therapeutic selected from acetazolamide, theophylline, progesterone, donepezil, naloxone, nicotine, paroxetine, protriptyline, metoprolol, cilazapril, propranolol, atenolol, hydrochlorothiazide, isradipine, spirapril, doxapram, clonidine, baclofen, and sabeluzole.

11. The method of claim 1, wherein the CSE antagonist is administered orally, subcutaneously, topically, intramuscularly, or intravenously.

12. The method of claim 1, wherein the individual has been diagnosed with a sleep-related breathing disorder.

13. The method of claim 1, wherein the CSE antagonist is at least one of:
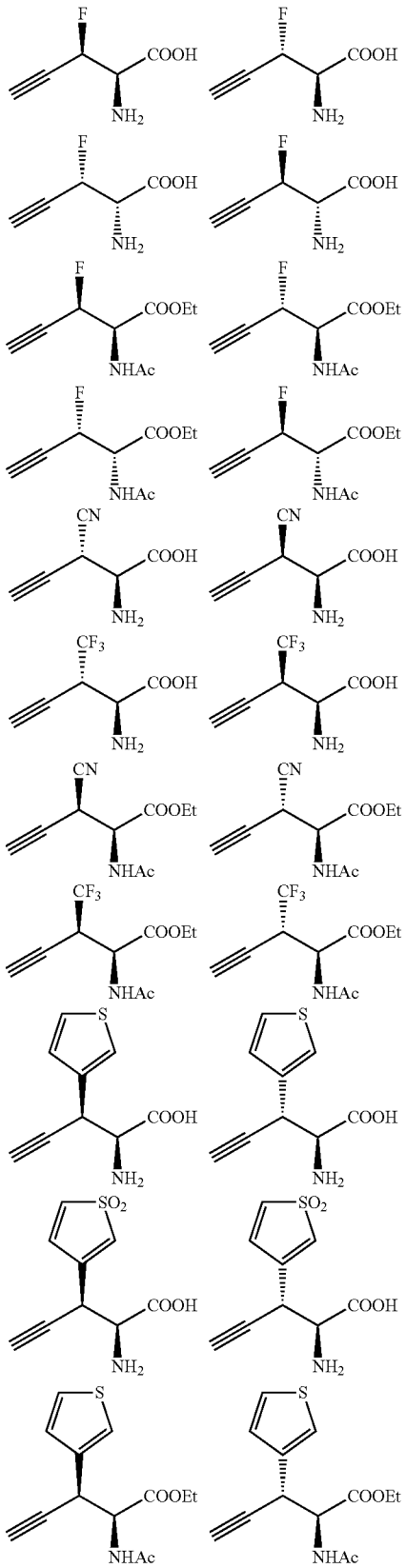
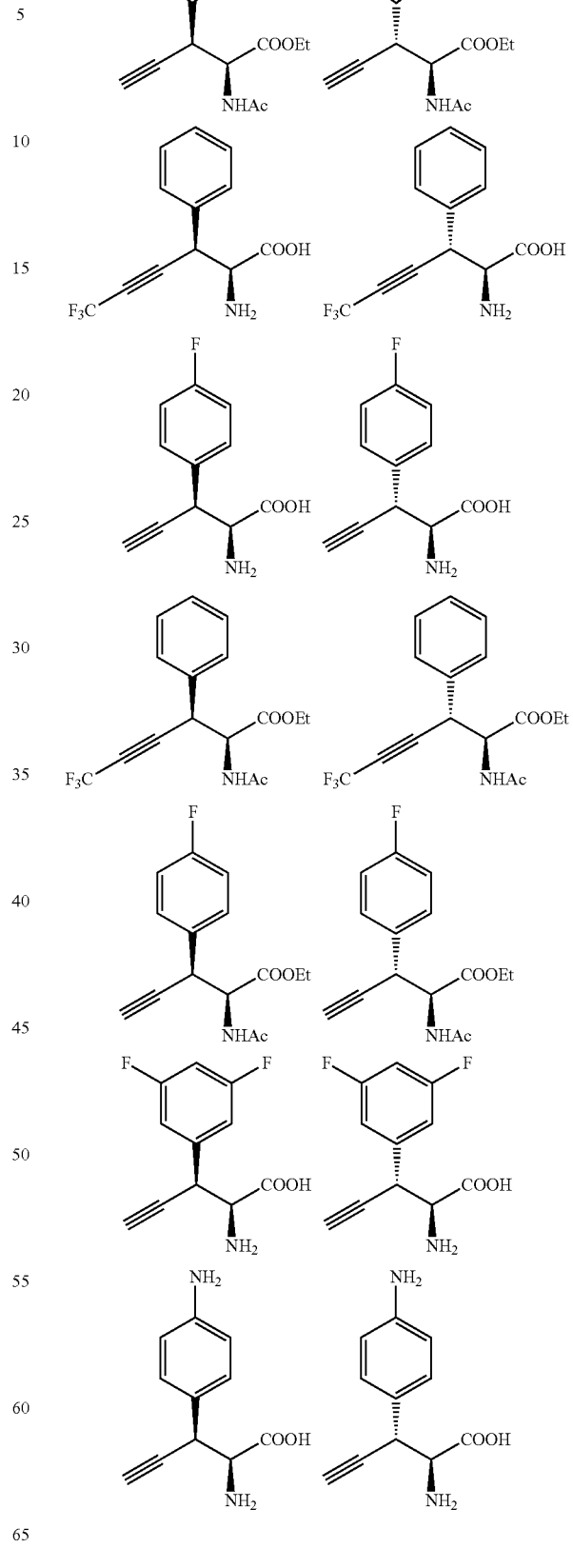

-continued
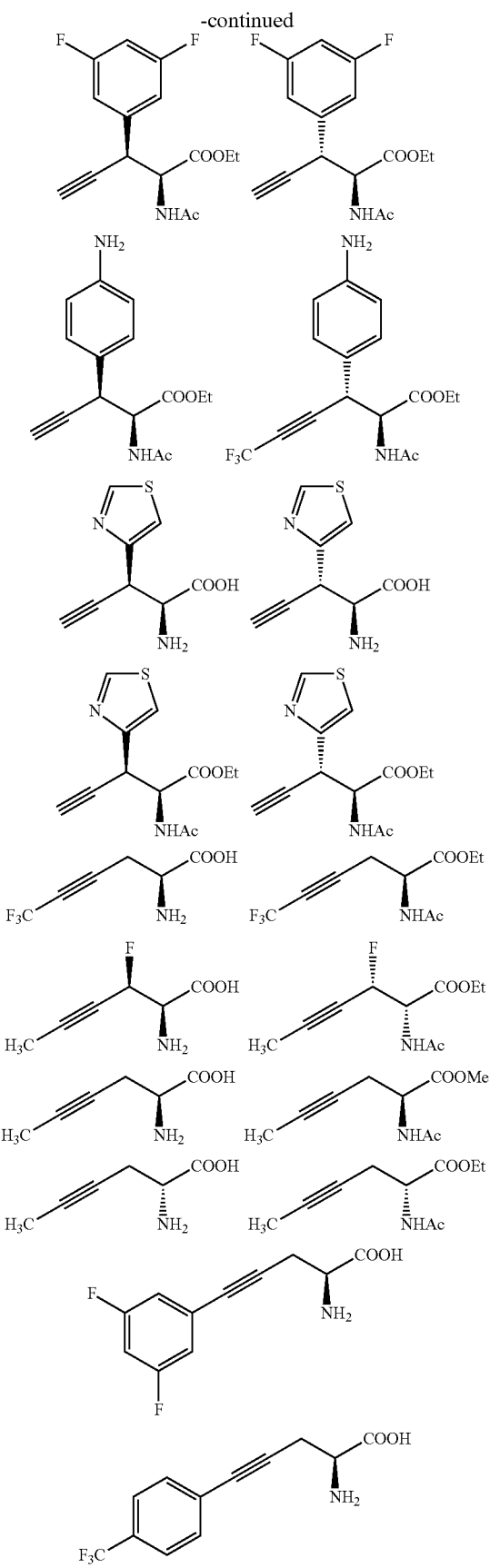
-continued
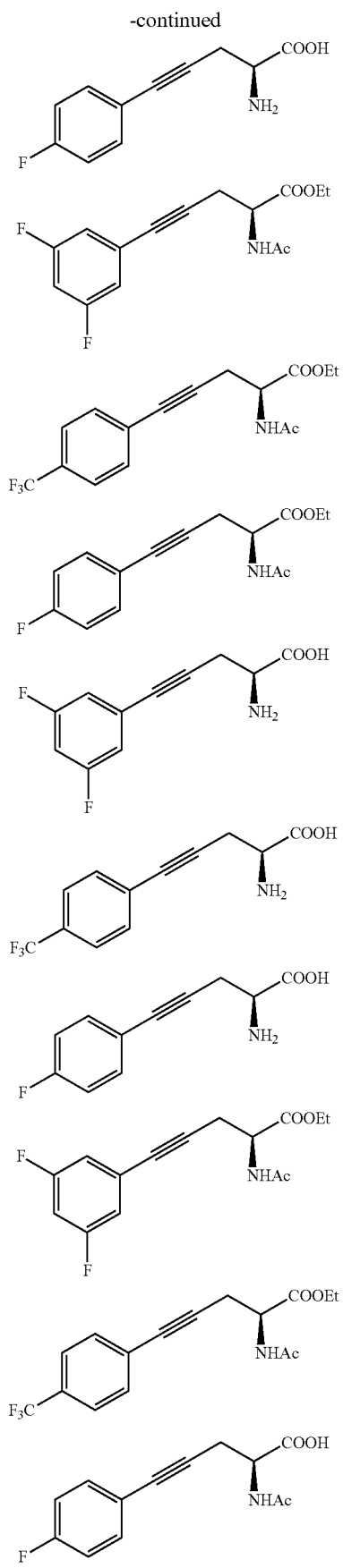

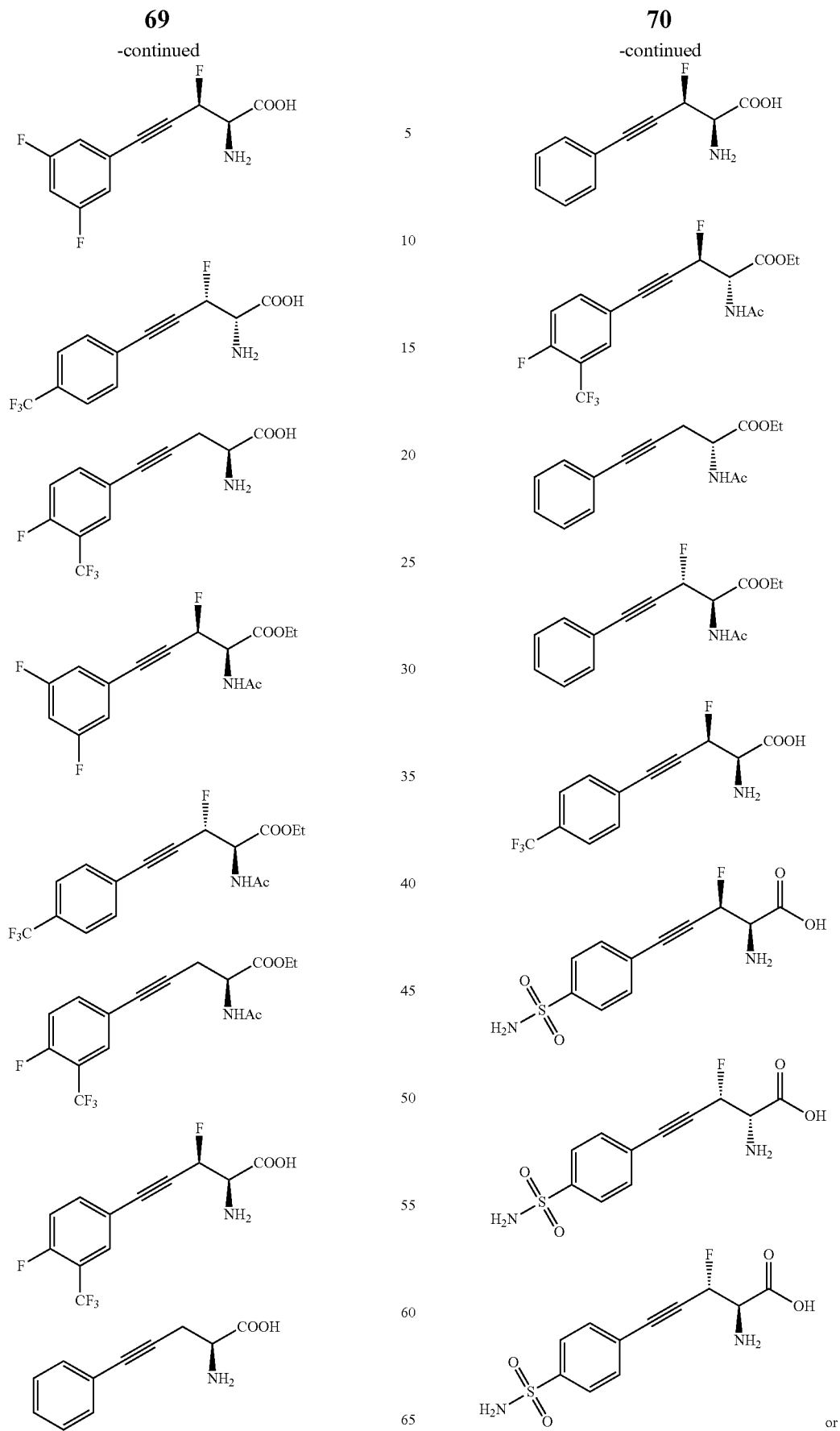

-continued

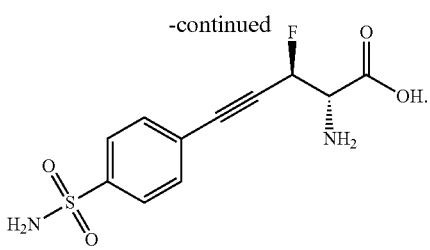

14. The method of claim 1, wherein the CSE antagonist is further defined as a compound of the formula

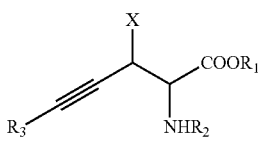

wherein:
R₁ is hydrogen;
R₂ is hydrogen;
R₃ is substituted aryl; and
X is hydrogen or halide;
or a pharmaceutically acceptable salt, enantiomer, diastereomer, or prodrug thereof.

15. The method of claim 14, wherein the CSE antagonist is

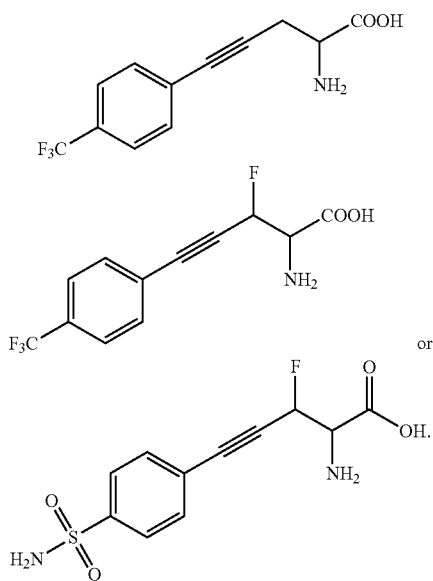

16. The method of claim 15, wherein the CSE antagonist is

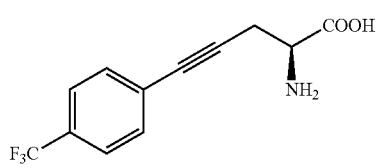 [SMILES: N[C@@H](CC#Cc1ccc(C(F)(F)F)cc1)C(=O)O]

-continued

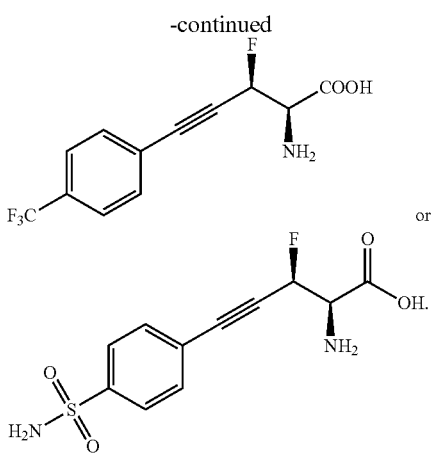

17. A propargylglycine analog compound of the formula:

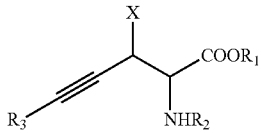

wherein:
R₁ and R₃ are independently hydrogen, substituted or unsubstituted alkyl, substituted or unsubstituted aryl, substituted or unsubstituted heteroaryl, or substituted or unsubstituted heterocycle;
R₂ is hydrogen, acyl, substituted or unsubstituted alkyl, substituted or unsubstituted aryl, substituted or unsubstituted heteroaryl, or substituted or unsubstituted heterocycle; and
X is hydrogen, halide, CN, substituted or unsubstituted alkyl, substituted or unsubstituted aryl, substituted or unsubstituted heteroaryl, or substituted or unsubstituted heterocycle;
or a salt, enantiomer, or diastereomer thereof, wherein R1, R2, R3, and X are not all hydrogen.

18. The compound of claim 17, further defined as:

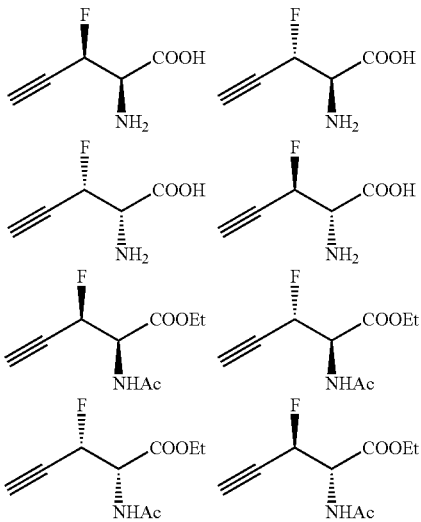

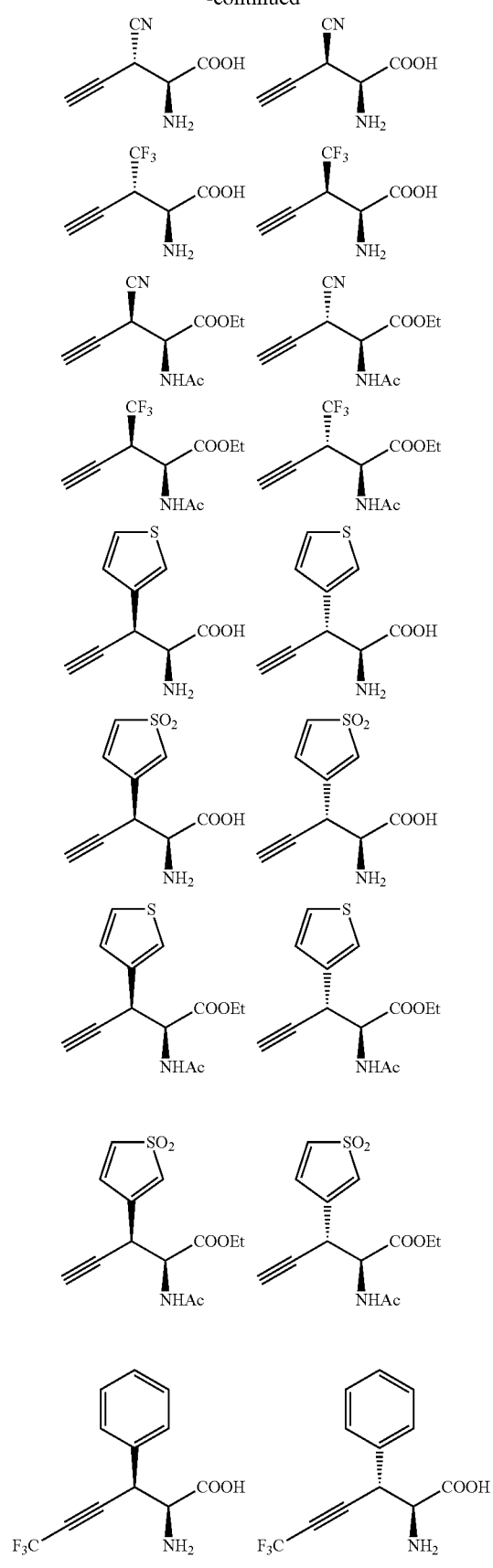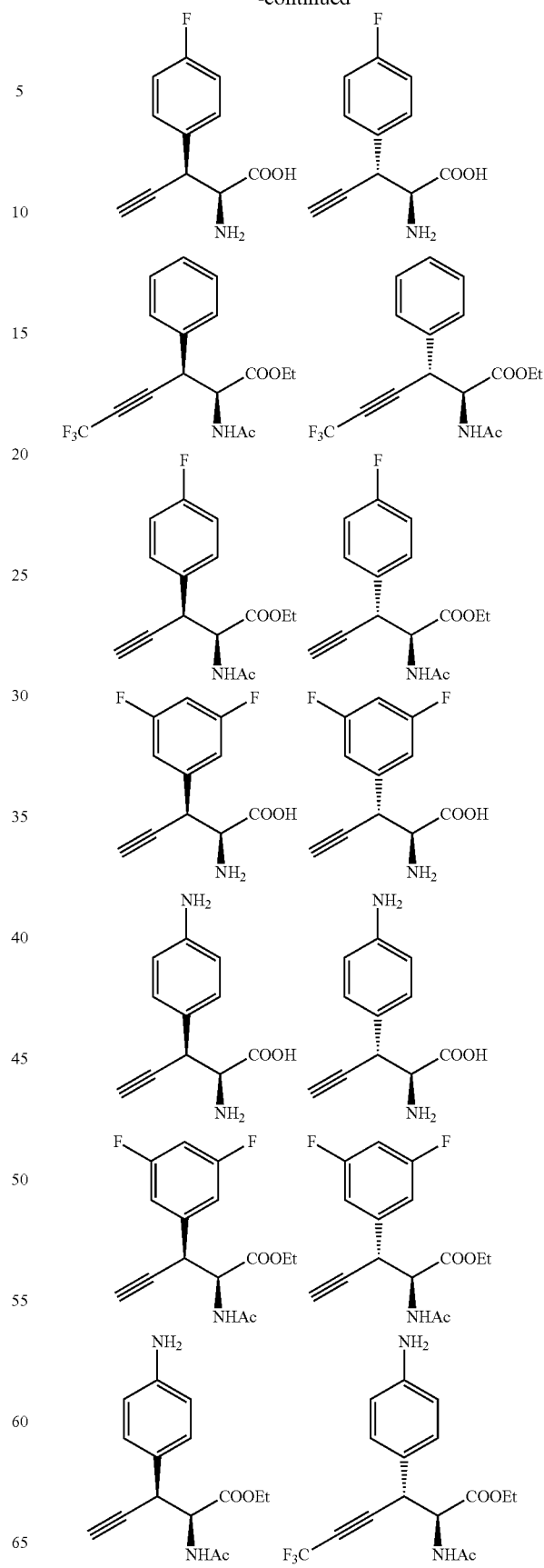

75
-continued
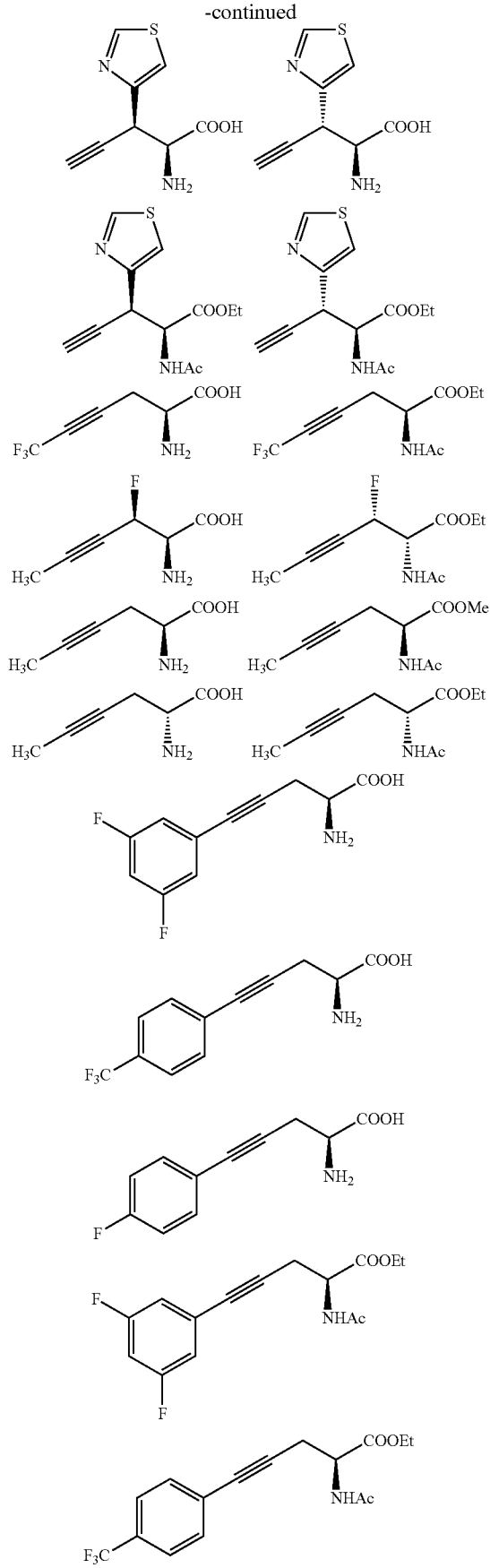
76
-continued
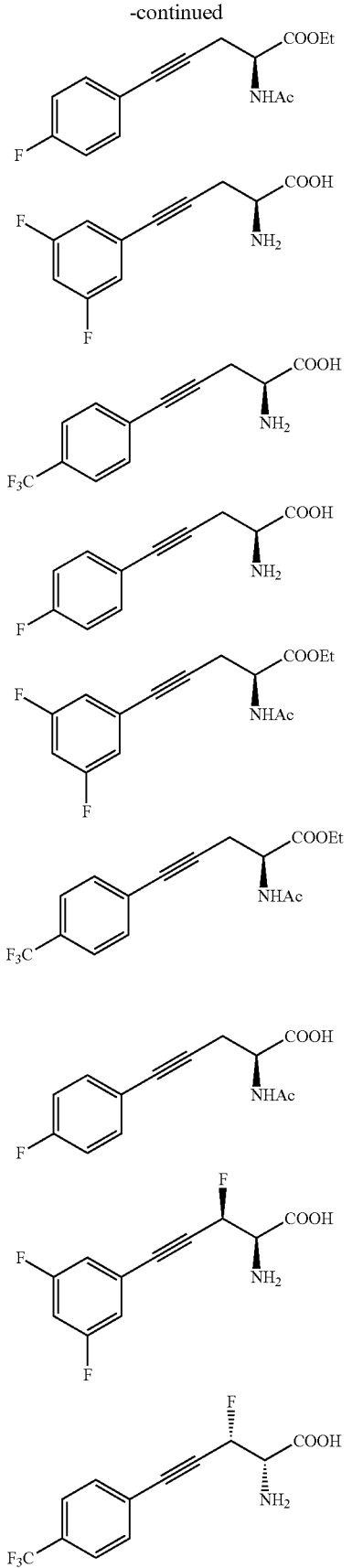

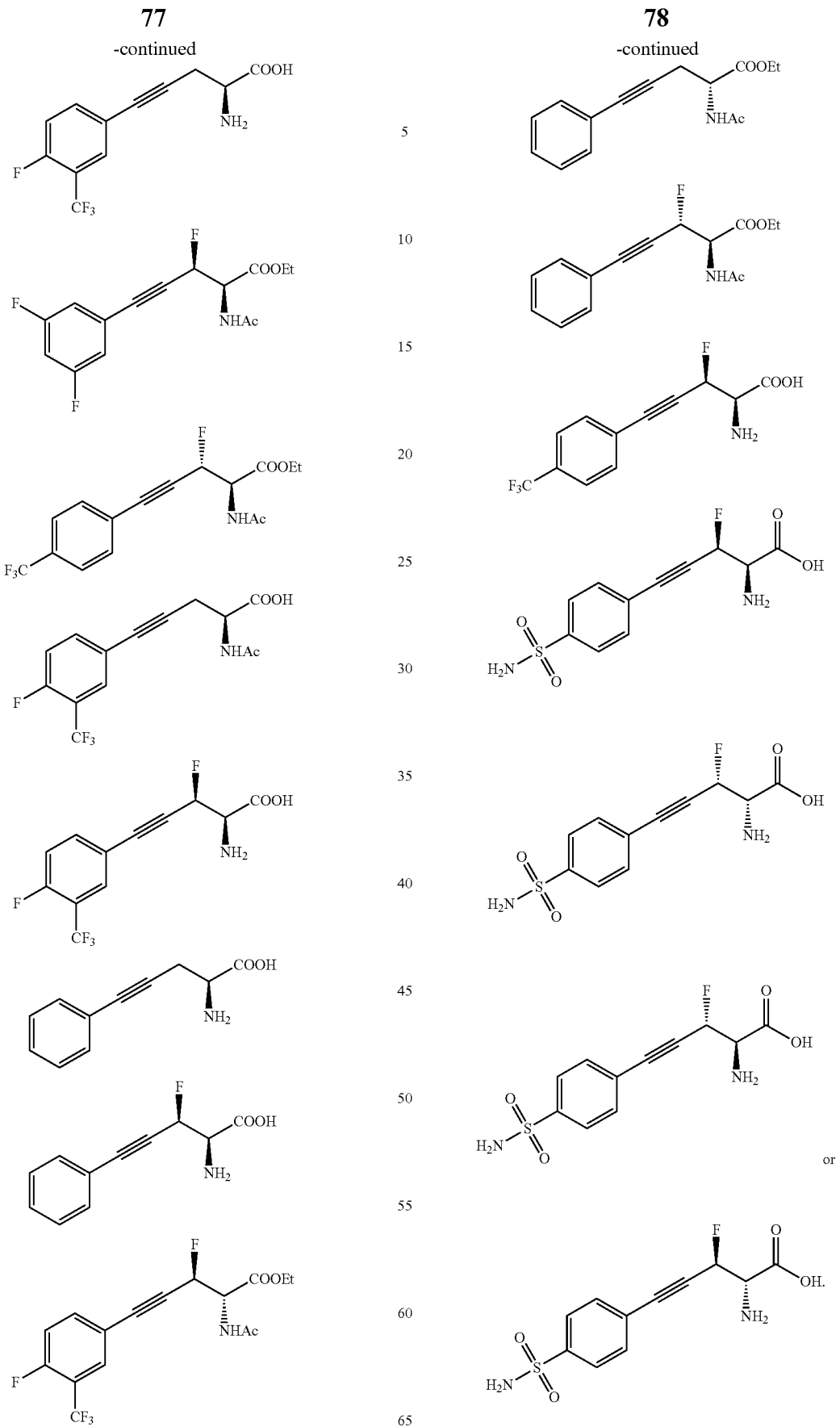

19. The compound of claim 17, wherein the compound is further defined as a compound of the formula

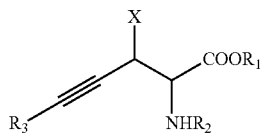

wherein:
R₁ is hydrogen;
R₂ is hydrogen;
R₃ is substituted aryl; and
X is hydrogen or halide;
or a salt, enantiomer, or diastereomer thereof.

20. The compound of claim 19, wherein the compound is

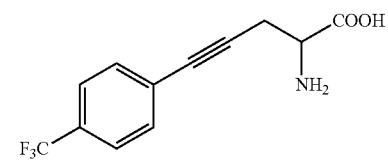

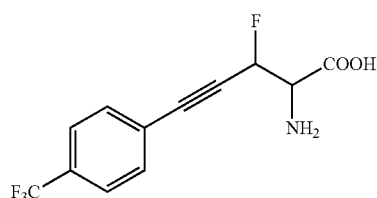

or

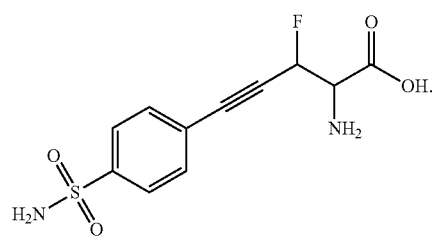

21. The compound of claim 20, wherein the compound is

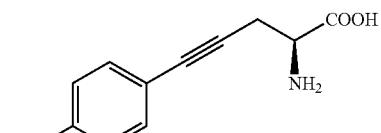

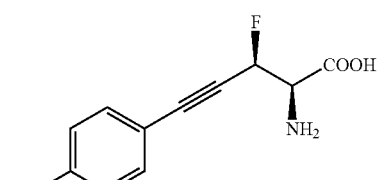

or

-continued

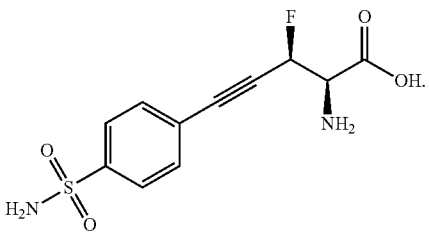 [SMILES: N[C@H](C(=O)O)[C@H](F)C#Cc1ccc(S(N)(=O)=O)cc1]

22. A method of treating or reducing a sleep-related breathing disorder selected from central sleep apnea (CSA), Cheyne-Stokes breathing-central sleep apnea (CSB-CSA), obesity hypoventilation syndrome (OHS), congenital central hypoventilation syndrome (CCHS), obstructive sleep apnea (OSA), idiopathic central sleep apnea (ICSA), narcotic-induced CSA, high altitude periodic breathing, chronic mountain sickness, impaired respiratory motor control associated with stroke, upper airway resistance syndrome (UARS), or impaired respiratory motor control associated with a neurologic disorder in an individual having or suffering from symptoms thereof comprising administering to the individual a therapeutically effective amount of:

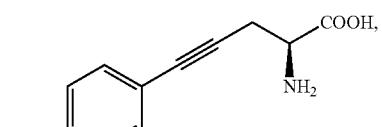

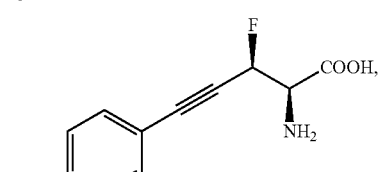

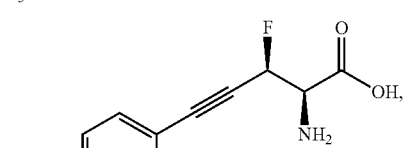

or a combination thereof.

23. The method of claim 22, wherein the individual is administered an effective amount of

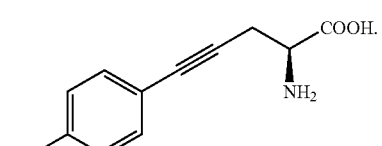

24. The method of claim 22, wherein the individual is administered an effective amount of